(12) United States Patent
Chen et al.

(10) Patent No.: US 9,441,008 B2
(45) Date of Patent: Sep. 13, 2016

(54) 3-SUBSTITUTED 5-AMINO-6H-THIAZOLO[4,5-D]PYRIMIDINE-2,7-DIONE COMPOUNDS FOR THE TREATMENT AND PROPHYLAXIS OF VIRUS INFECTION

(71) Applicant: Hoffmann-La Roche Inc., Little Falls, NJ (US)

(72) Inventors: Dongdong Chen, Shanghai (CN); Song Feng, Shanghai (CN); Lu Gao, Shanghai (CN); Chao Li, Shanghai (CN); Baoxia Wang, Shanghai (CN); Lisha Wang, Riehen (CH); Hongying Yun, Shanghai (CN); Xiufang Zheng, Shanghai (CN)

(73) Assignee: Hoffmann-LA Roche Inc., Little Falls, NJ (US)

( * ) Notice: Subject to any disclaimer, the term of this patent is extended or adjusted under 35 U.S.C. 154(b) by 0 days.

(21) Appl. No.: 14/958,619

(22) Filed: Dec. 3, 2015

(65) Prior Publication Data
US 2016/0194350 A1    Jul. 7, 2016

(30) Foreign Application Priority Data

Dec. 8, 2014   (WO) ................ PCT/CN2014/093224
Aug. 14, 2015  (WO) ................ PCT/CN2015/086987

(51) Int. Cl.
*C07H 19/24* (2006.01)
*C07D 513/04* (2006.01)

(52) U.S. Cl.
CPC ............ *C07H 19/24* (2013.01); *C07D 513/04* (2013.01)

(58) Field of Classification Search
None
See application file for complete search history.

(56) References Cited

U.S. PATENT DOCUMENTS

| 5,476,659 | A  |   | 12/1995 | Goodman et al. |
| 7,560,544 | B2 | * | 7/2009  | Webber .............. C07D 513/04 536/27.2 |
| 7,709,448 | B2 | * | 5/2010  | Haley ................ C07D 513/04 514/42 |
| 2005/0004144 | A1 |   | 1/2005 | Carson et al. |

FOREIGN PATENT DOCUMENTS

| EP | 0343945 | 11/1989 |
| EP | 1072607 | 1/2001 |
| WO | 89/05649 | 6/1989 |
| WO | 98/16184 | 4/1998 |
| WO | 2005/016235 | 2/2005 |
| WO | 2005/025583 | 3/2005 |
| WO | 2007/135134 | 11/2007 |
| WO | 2008/011406 | 1/2008 |
| WO | 2008/140549 | 11/2008 |
| WO | 2009/026292 A1 | 2/2009 |

OTHER PUBLICATIONS

Asselah et al., "Interferon therapy for chronic hepatitis B" Clin Liver Dis 11:839-849 (2007).
Connolly et al., "New developments in Tool-like receptor targeted therapeutics" Current Opinion in Pharmacology 12:510-518 (2012).
Gane et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 (Nov. 2013).
Hemmi et al., "Small anti-viral compounds activate immune cells via the TLR7 MyD88-dependent signalling pathway" Nature Immunology 3(2):196 (2002).
Kaisho et al., "Turning NF-kB and IRFs on and off in DC" Trends in Immunology 29(7):329-336 (2008).
Roethle et al., "Identification and Optimization of Pteridinone Toll-like Receptor 7 (TLR7) Agonist for the Oral Treatment of Viral Hepatitis" Journal of Medicinal Chemistry 56(18):7324-7333 (Sep. 26, 2013).

\* cited by examiner

*Primary Examiner* — Traviss C McIntosh, III
(74) *Attorney, Agent, or Firm* — Jonathan Duffield

(57) ABSTRACT

The present invention relates to compounds of formula (I),

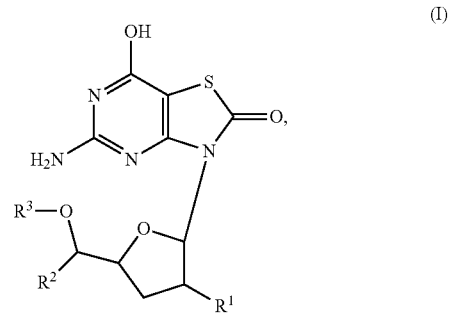

wherein $R^1$, $R^2$ and $R^3$ are as described herein, and their prodrugs or pharmaceutically acceptable salt, enantiomer or diastereomer thereof, and compositions including the compounds and methods of using the compounds.

54 Claims, 3 Drawing Sheets

3-SUBSTITUTED 5-AMINO-6H-THIAZOLO[4,5-D]PYRIMIDINE-2,7-DIONE COMPOUNDS FOR THE TREATMENT AND PROPHYLAXIS OF VIRUS INFECTION

CROSS REFERENCE TO RELATED APPLICATIONS

This application claims the benefit under 35 U.S.C. §119(a) to International Application PCT/CN2015/086987, filed Aug. 14, 2015, and claims the benefit under 35 U.S.C. §119(a) to International Application PCT/CN2014/093224, filed Dec. 8, 2014.

FIELD OF THE INVENTION

The present invention relates to novel 3-substituted 5-amino-6H-thiazolo[4,5-d]pyrimidine-2,7-dione compounds, that have Toll-like receptor agonism activity and their prodrugs thereof, as well as their manufacture, pharmaceutical compositions containing them and their potential use as medicaments.

The present invention relates to compounds of formula (I) and (Ia),

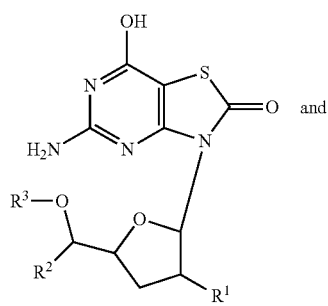

(I)

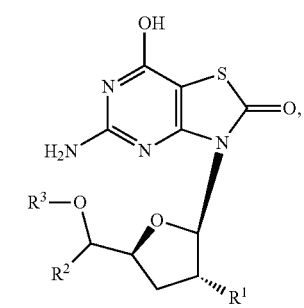

(Ia)

and their prodrugs, formula (II) and (IIa),

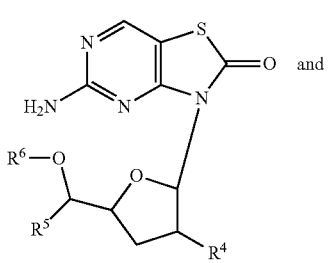

(II)

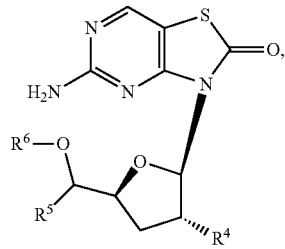

(IIa)

wherein $R^1$ to $R^6$ are described below, or pharmaceutically acceptable salt, enantiomer or diastereomer thereof.

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7 TLR8, and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. A J O'Neill, Current Opinion in Pharmacology 2012, 12:510-518, P. A. Roethle et al, J. Med. Chem. 2013, 56, 7324-7333).

The current therapy of chronic HBV infection is based on two different types of drugs: the traditional antiviral nucleos(t)ide analogues and the more recent Pegylated IFN-α (PEG-IFN-α). The oral nucleos(t)ide analogues act by suppressing the HBV replication. This is a life-long course of treatment during which drug resistance often occurs. As an alternative option, Pegylated IFN-α (PEG-IFN-α) has been used to treat some chronic infected HBV patients within finite therapy duration. Although it has achieved seroconversion in HBeAg at least in a small percentage of HBV patients, the adverse effect makes it poorly tolerable. Notably, functional cure defined as HBsAg seroconversion is very rare with both current therapies. A new generation therapeutic option to treat HBV patients for a functional cure is therefore of urgent need. Treatment with an oral TLR7 agonist represents a promising solution to provide greater efficacy with better tolerability. Pegylated IFN-α (PEG-IFN-α) is currently used to treat chronic HBV and is an alternative to potentially life-long treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleos(t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

In fact, several identified TLR7 agonists have been considered for therapeutic purposes. So far Imiquimod (AL-DARA™) is a U.S. FDA approved TLR7 agonist drug for topical use to treat skin lesions by human papillomavirus. The TLR7/8 dual agonist resiquimod (R-848) and the TLR7 agonist 852A have been evaluated for treating human genital herpes and chemotherapy-refractory metastatic melanoma, respectively. ANA773 is an oral pro-drug TLR7 agonist, developed for the treatment of patients with chronic hepatitis C virus (HCV) infection and chronic hepatitis B infection. GS-9620 is an orally available TLR7 agonist. A phase Ib study demonstrated that treatment with GS-9620 was safe, well tolerated and resulted in dose-dependent ISG15 mRNA induction in patients with chronic hepatitis B (E. J. Gane et al, Annu Meet Am Assoc Study Liver Dis (November 1-5, Washington, D.C.) 2013, Abst 946). Therefore there is high unmet clinical need for developing potent and safe TLR7 agonists as new HBV treatment to offer more therapeutic solutions or replace existing partly effective treatment.

SUMMARY OF THE INVENTION

The present invention provides a series of novel 3-substituted 5-amino-6H-thiazolo[4,5-d]pyrimidine-2,7-dione compounds, that have Toll-like receptor agonism activity and their prodrugs. The invention also provides the bioactivity of such compounds to induce SEAP level increase by activating Toll-like receptors, such as TLR7 receptor, the metabolic conversion of prodrugs to parent compounds in the presence of human hepatocytes, and the therapeutic or prophylactic use of such compounds and their pharmaceutical compositions comprising these compounds and their prodrugs to treat or prevent infectious disease like HBV or HCV. The present invention also provides compounds with superior activity. In addition, the compounds of formula (I) and (Ia) also showed good solubility and PK profiles.

The present invention relates to novel compounds of formula (I) and (Ia),

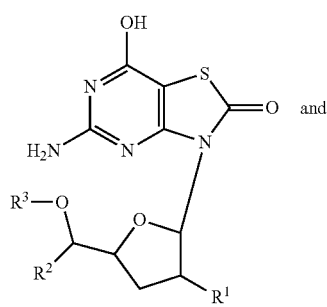

(I)

and

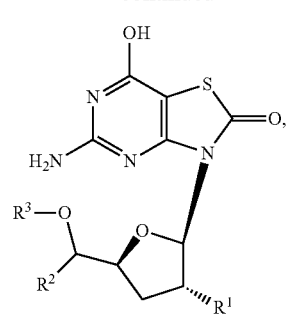

(Ia)

wherein
$R^1$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}$alkyl$)_2$N—, $C_{1-6}$alkylcarbonyl-NH— or heterocyclic amino;
$R^2$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^3$ is hydrogen or $C_{1-6}$alkylcarbonyl;
or pharmaceutically acceptable salt, enantiomer or diastereomer thereof; with the proviso that 5-amino-7-hydroxy-3-[3-hydroxy-5-(hydroxymethyl)tetrahydrofuran-2-yl]thiazolo[4,5-d]pyrimidin-2-one; [2-(5-amino-7-hydroxy-2-oxo-thiazolo[4,5-d]pyrimidin-3-yl)-5-(hydroxymethyl)tetrahydrofuran-3-yl]acetate; [4-acetoxy-5-(5-amino-7-hydroxy-2-oxo-thiazolo[4,5-d]pyrimidin-3-yl)tetrahydrofuran-2-yl]methyl acetate and their diastereomers are excluded.

The present invention also relates to the prodrugs of formula (II) and (IIa),

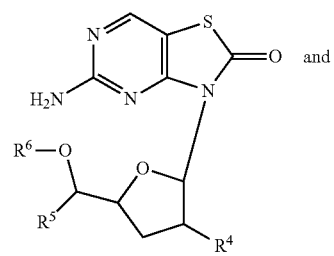

(II)

and

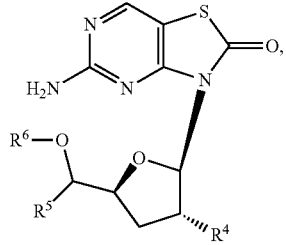

(IIa)

wherein
$R^4$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}$alkyl$)_2$N—, $C_{1-6}$alkylcarbonyl-NH— or heterocyclic amino;
$R^5$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^6$ is hydrogen or $C_{1-6}$alkylcarbonyl;
or pharmaceutically acceptable salt, enantiomer or diastereomer thereof; with the proviso that 5-amino-3-[3-hydroxy- 5-(hydroxymethyl)tetrahydrofuran-2-yl]thiazolo[4,5-d]pyrimidin-2-one; [2-(5-amino-2-oxo-thiazolo[4,5-d]pyrimidin-3-yl)-5-(hydroxymethyl)tetrahydrofuran-3-yl] acetate; [4-acetoxy-5-(5-amino-2-oxo-thiazolo[4,5-d]pyrimidin-3-yl)tetrahydrofuran-2-yl]methyl acetate and their diastereomers are excluded.

The invention also relates to their manufacture, medicaments based on a compound in accordance with the invention and their production as well as the use of compounds of formula (I) or (Ia) or their prodrugs, formula (II) or (IIa), thereof as TLR7 agonist. Accordingly, the compounds of formula (I) and (Ia) or their prodrugs of formula (II) and (IIa) are useful for the treatment or prophylaxis of HBV and/or HCV infection with Toll-like receptors agonism.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

As used herein, the term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "halogen" and "halo" are used interchangeably herein and denote fluoro, chloro, bromo, or iodo.

The term "halo$C_{1-6}$alkyl" refers to an alkyl group wherein at least one of the hydrogen atoms of the alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl and trifluoromethyl.

The term "heterocyclic" ring denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclic ring is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclic ring are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocyclic ring are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocyclic ring are dihydrofuryl, imidazolinyl, dihydro-oxazolyl, tetrahydro-pyridinyl, and dihydropyranyl.

The term "heterocyclic amino" denotes an amino group with the nitrogen atom on the heterocyclic ring.

The term "$C_{2-6}$alkenyl" denotes an unsaturated, linear or branched chain alkenyl group containing 2 to 6, particularly 2 to 4 carbon atoms, for example vinyl, propenyl, allyl, butenyl and the like. Particular "$C_{2-6}$alkenyl" groups are allyl and vinyl.

The term "$C_{2-6}$alkynyl" denotes an unsaturated, linear or branched chain alkynyl group containing 2 to 6, particularly 2 to 4 carbon atoms, for example ethynyl, 1-propynyl, propargyl, butynyl and the like. Particular "$C_{2-6}$alkynyl" groups are ethynyl and 1-propynyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" group is cyclopropyl.

The term "carbonyl" alone or in combination refers to the group —C(O)—.

The term "$C_{1-6}$alkylcarbonyl" refers to a group $C_{1-6}$alkyl-C(O)—, wherein the "$C_{1-6}$alkyl" is as defined above. Particular "$C_{1-6}$alkylcarbonyl" group is acetyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) or (Ia) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds of the invention may exhibit the phenomenon of tautomerism. While the formula drawings cannot expressly depict all possible tautomeric forms, it is to be understood they are intended to represent any tautomeric form of the depicted compound and are not to be limited merely to a specific compound form depicted by the formula drawings. For example, it is understood for formula (III) that regardless of whether or not the substituents are shown in their enol or their keto form, they represent the same compound (as shown in the example below).

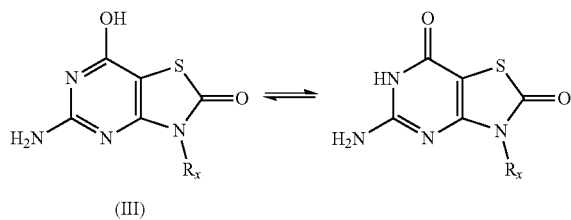

(III)

$R_x$ refers to any feasible substituent.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form. As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.). Additionally, compounds of formula (I) and (Ia) and their prodrugs, formula (II) and (IIa), and other compounds of the invention are intended to cover solvated as well as unsolvated forms of the identified structures. For example, formula (I) or (Ia) includes compounds of the indicated structure in both hydrated and non-hydrated forms. Other examples of solvates include the structures in combination with isopropanol, ethanol, methanol, DMSO, ethyl acetate, acetic acid, or ethanolamine.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 Agonist and Prodrug

The present invention relates to a compound of formula (I),

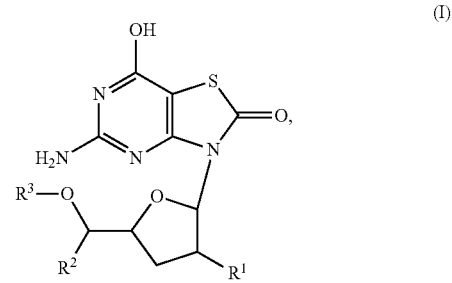

wherein
$R^1$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}alkyl)_2N$—, $C_{1-6}$alkylcarbonyl-NH— or heterocyclic amino;
$R^2$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^3$ is hydrogen or $C_{1-6}$alkylcarbonyl;
or pharmaceutically acceptable salt, enantiomer or diastereomer thereof;
with the proviso that 5-amino-7-hydroxy-3-[3-hydroxy-5-(hydroxymethyl)tetrahydrofuran-2-yl]thiazolo[4,5-d]pyrimidin-2-one; [2-(5-amino-7-hydroxy-2-oxo-thiazolo[4,5-d]pyrimidin-3-yl)-5-(hydroxymethyl)tetrahydrofuran-3-yl] acetate; [4-acetoxy-5-(5-amino-7-hydroxy-2-oxo-thiazolo[4,5-d]pyrimidin-3-yl)tetrahydrofuran-2-yl]methyl acetate and their diastereomers are excluded.

Further embodiment of present invention is (ii) a compound of formula (I), wherein
$R^1$ is hydroxy, methyl, propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;

R² is hydrogen, methyl, ethyl, propyl, butyl, cyclopropyl, cyclopentyl, vinyl, allyl, benzyl, ethynyl, 1-propynyl, methoxymethyl or thiophenyl;

R³ is hydrogen, acetyl or isobutyryl;

or pharmaceutically acceptable salt, enantiomer or diastereomer thereof.

Another embodiment of present invention is (iii) a compound of formula (Ia),

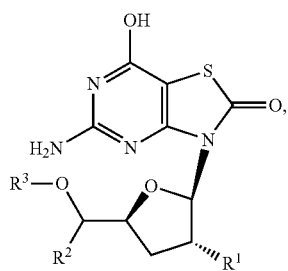

(Ia)

wherein

R¹ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, ($C_{1-6}$alkyl)₂N—, $C_{1-6}$alkylcarbonyl-NH— or heterocyclic amino; R² is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl or thiophenyl;

R³ is hydrogen or $C_{1-6}$alkylcarbonyl;

or pharmaceutically acceptable salt, enantiomer or diastereomer thereof;

with the proviso that 5-amino-7-hydroxy-3-[3-hydroxy-5-(hydroxymethyl)tetrahydrofuran-2-yl]thiazolo[4,5-d]pyrimidin-2-one; [2-(5-amino-7-hydroxy-2-oxo-thiazolo[4,5-d]pyrimidin-3-yl)-5-(hydroxymethyl)tetrahydrofuran-3-yl] acetate; [4-acetoxy-5-(5-amino-7-hydroxy-2-oxo-thiazolo[4,5-d]pyrimidin-3-yl)tetrahydrofuran-2-yl]methyl acetate and their diastereomers are excluded.

Further embodiment of present invention is (iv) a compound of formula (Ia), wherein R¹ is hydroxy, methyl, propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;

R² is hydrogen, methyl, ethyl, propyl, butyl, cyclopropyl, cyclopentyl, vinyl, allyl, benzyl, ethynyl, 1-propynyl, methoxymethyl or thiophenyl;

R³ is hydrogen, acetyl or isobutyryl;

or pharmaceutically acceptable salt, enantiomer or diastereomer thereof.

Another embodiment of present invention is (v) a compound of formula (I) or (Ia), wherein R¹ is hydroxy, $C_{1-6}$alkyl, $C_{1-6}$alkylcarbonyl-O—, $C_{1-6}$alkyl-S—, azido or $C_{2-6}$alkenyl;

R² is $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;

R³ is hydrogen or $C_{1-6}$alkylcarbonyl;

or pharmaceutically acceptable salt, enantiomer or diastereomer thereof.

A further embodiment of present invention is (vi) a compound of formula (I) or (Ia), wherein R¹ is hydroxy, methyl, propyl, acetyloxy, methylsulfanyl, azido or allyl;

R² is methyl, ethyl, propyl, butyl, cyclopropyl, cyclopentyl, vinyl, allyl, benzyl, ethynyl, 1-propynyl, methoxymethyl or thiophenyl;

R³ is hydrogen, acetyl or isobutyryl;

or pharmaceutically acceptable salt, enantiomer or diastereomer thereof.

A further embodiment of present invention is (vii) a compound of formula (I) or (Ia), wherein R¹ is hydroxy, $C_{1-6}$alkyl, $C_{1-6}$alkyl-S—, azido or $C_{2-6}$alkenyl.

A further embodiment of present invention is (viii) a compound of formula (I) or (Ia), wherein R¹ is hydroxy, methyl, n-propyl, methylsulfanyl, azido or allyl.

A further embodiment of present invention is (ix) a compound of formula (I) or (Ia), wherein R² is $C_{1-6}$alkyl, $C_{3-7}$cycloalkyl, $C_{2-6}$alkynyl or $C_{2-6}$alkenyl.

A further embodiment of present invention is (x) a compound of formula (I) or (Ia), wherein R² is methyl, ethyl, n-propyl, cyclopropyl, vinyl, ethynyl or 1-propynyl.

A further embodiment of present invention is (xi) a compound of formula (I) or (Ia), wherein R³ is hydrogen or $C_{1-6}$alkylcarbonyl.

A further embodiment of present invention is (xii) a compound of formula (I) or (Ia), wherein R³ is hydrogen or isobutyryl.

Another embodiment of present invention is (xiii) a compound of formula (I) or (Ia), wherein R¹ is hydroxy, $C_{1-6}$alkyl, $C_{1-6}$alkyl-S—, azido or $C_{2-6}$alkenyl;

R² is $C_{1-6}$alkyl, $C_{3-7}$cycloalkyl, $C_{2-6}$alkynyl or $C_{2-6}$alkenyl;

R³ is hydrogen or $C_{1-6}$alkylcarbonyl;

or pharmaceutically acceptable salt, enantiomer or diastereomer thereof.

A further embodiment of present invention is (xiv) a compound of formula (I) or (Ia), wherein R¹ is hydroxy, methyl, propyl, methylsulfanyl, azido or allyl;

R² is methyl, ethyl, propyl, cyclopropyl, vinyl, ethynyl or 1-propynyl;

R³ is hydrogen or isobutyryl;

or pharmaceutically acceptable salt, enantiomer or diastereomer thereof.

Another embodiment of present invention is (xv) a compound of formula (I) or (Ia), wherein R¹ is halo$C_{1-6}$alkyl, $C_{1-6}$alkyl-S—, cyano, $C_{2-6}$alkenyl, $C_{1-6}$alkylsulfonyl-NH—, ($C_{1-6}$alkyl)₂N—, $C_{1-6}$alkylcarbonyl-NH— or heterocyclic amino;

R² is hydrogen;

R³ is hydrogen;

or pharmaceutically acceptable salt, enantiomer or diastereomer thereof.

A further embodiment of present invention is (xvi) a compound of formula (I) or (Ia), wherein R¹ is fluoroisopropyl, methylsulfanyl, cyano, 2-methylallyl, methylsulfonylamino, dimethylamino, acetylamino, pyrrolidinyl, morpholinyl or piperidinyl;

R² is hydrogen;

R³ is hydrogen;

or pharmaceutically acceptable salt, enantiomer or diastereomer thereof

A further embodiment of present invention is (xvii) a compound of formula (I) or (Ia), wherein R¹ is $C_{1-6}$alkyl-S— or heterocyclic amino.

A further embodiment of present invention is (xviii) a compound of formula (I) or (Ia), wherein R¹ is methylsulfanyl or pyrrolidinyl.

Another embodiment of present invention is that (xix) particular compounds of formula (I) or (Ia) are the following:

5-Amino-3-[(2R,3R,5S)-3-hydroxy-5-(1-hydroxypropyl) tetrahydrofuran-2-yl]-6H-thiazolo[4,5-c]pyrimidine-2,7-dione;

[(2R,3R,5S)-2-(5-amino-2,7-dioxo-6H-thiazolo[4,5-c]pyrimidin-3-yl)-5-(1-hydroxypropyl)tetrahydrofuran-3-yl] acetate;

[(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl]acetate;

5-Amino-3-[(2R,3R,5S)-3-hydroxy-5-(1-hydroxyethyl)tetrahydrofuran-2-yl]-6H-thiazolo[4,5-c]pyrimidine-2,7-dione;

5-Amino-3-[(2R,3R,5S)-3-hydroxy-5-(1-hydroxybut-3-enyl)tetrahydrofuran-2-yl]-6H-thiazolo[4,5-d]pyrimidine-2,7-dione;

5-Amino-3-[(2R,3R,5S)-3-hydroxy-5-(1-hydroxypentyl)tetrahydrofuran-2-yl]-6H-thiazolo[4,5-c]pyrimidine-2,7-dione;

5-Amino-3-[(2R,3R,5S)-3-hydroxy-5-(1-hydroxybutyl)tetrahydrofuran-2-yl]-6H-thiazolo[4,5-c]pyrimidine-2,7-dione;

5-Amino-3-[(2R,3R,5S)-5-[cyclopentyl(hydroxy)methyl]-3-hydroxy-tetrahydrofuran-2-yl]-6H-thiazolo[4,5-c]pyrimidine-2,7-dione;

5-Amino-3-[(2R,3R,5S)-3-hydroxy-5-(1-hydroxy-2-phenyl-ethyl)tetrahydrofuran-2-yl]-6H-thiazolo[4,5-c]pyrimidine-2,7-dione;

5-Amino-3-[(2R,3R,5S)-3-hydroxy-5-(1-hydroxy-3-methyl-butyl)tetrahydrofuran-2-yl]-6H-thiazolo[4,5-c]pyrimidine-2,7-dione;

5-Amino-3-[(2R,3R,5S)-5-[cyclopropyl(hydroxy)methyl]-3-hydroxy-tetrahydrofuran-2-yl]-6H-thiazolo[4,5-c]pyrimidine-2,7-dione;

[[(2S,4R,5R)-5-(5-amino-2,7-dioxo-6H-thiazolo[4,5-d]pyrimidin-3-yl)-4-hydroxy-tetrahydrofuran-2-yl]-cyclopropyl-methyl]acetate;

5-Amino-3-[(2R,3R,5S)-3-hydroxy-5-(1-hydroxyprop-2-ynyl)tetrahydrofuran-2-yl]-6H-thiazolo[4,5-d]pyrimidine-2,7-dione;

5-Amino-3-[(2R,3R,5S)-3-hydroxy-5-(1-hydroxybut-2-ynyl)tetrahydrofuran-2-yl]-6H-thiazolo[4,5-d]pyrimidine-2,7-dione;

5-Amino-3-[(2R,3R,5S)-3-hydroxy-5-[hydroxy(2-thienyl)methyl]tetrahydrofuran-2-yl]-6H-thiazolo[4,5-d]pyrimidine-2,7-dione;

5-Amino-3-[(2R,3R,5S)-3-hydroxy-5-(1-hydroxy-2-methoxy-ethyl)tetrahydrofuran-2-yl]-6H-thiazolo[4,5-d]pyrimidine-2,7-dione;

5-Amino-3-[(2R,3R,5S)-5-(1-hydroxypropyl)-3-methylsulfanyl-tetrahydrofuran-2-yl]-6H-thiazolo[4,5-d]pyrimidine-2,7-dione;

5-Amino-3-[(2R,3R,5S)-3-azido-5-(1-hydroxypropyl)tetrahydrofuran-2-yl]-6H-thiazolo[4,5-d]pyrimidine-2,7-dione;

5-Amino-3-[(2R,3R,5S)-3-hydroxy-5-(1-hydroxyallyl)tetrahydrofuran-2-yl]-6H-thiazolo[4,5-d]pyrimidine-2,7-dione;

5-Amino-3-((2R,3R,5S)-3-azido-5-((S)-1-hydroxyethyl)tetrahydrofuran-2-yl)thiazolo[4,5-d]pyrimidine-2,7(3H,6H)-dione;

3-[(2R,3R,5S)-3-allyl-5-(1-hydroxypropyl)tetrahydrofuran-2-yl]-5-amino-6H-thiazolo[4,5-d]pyrimidine-2,7-dione;

5-amino-3-[(2R,3R,5S)-5-[(1S)-1-hydroxypropyl]-3-propyl-tetrahydrofuran-2-yl]-6H-thiazolo[4,5-d]pyrimidine-2,7-dione;

5-amino-3-[(2R,3R,5S)-5-[(1R)-1-hydroxypropyl]-3-propyl-tetrahydrofuran-2-yl]-6H-thiazolo[4,5-d]pyrimidine-2,7-dione;

5-amino-3-[(2R,3R,5S)-5-[(1S)-1-hydroxypropyl]-3-methyl-tetrahydrofuran-2-yl]-6H-thiazolo[4,5-d]pyrimidine-2,7-dione;

5-Amino-3-[(2R,3R,5S)-5-[(1S)-1-hydroxybut-2-yl]-3-methyl-tetrahydrofuran-2-yl]-6H-thiazolo[4,5-d]pyrimidine-2,7-dione;

5-Amino-3-[(2R,3R,5S)-5-[(S)-cyclopropyl(hydroxy)methyl]-3-methyl-tetrahydrofuran-2-yl]-6H-thiazolo[4,5-d]pyrimidine-2,7-dione;

5-Amino-3-[(2R,3R,5S)-5-[(1S)-1-hydroxyethyl]-3-methyl-tetrahydrofuran-2-yl]-6H-thiazolo[4,5-d]pyrimidine-2,7-dione;

5-Amino-3-[(2R,3R,5S)-5-(hydroxymethyl)-3-pyrrolidin-1-yl-tetrahydrofuran-2-yl]-6H-thiazolo[4,5-d]pyrimidine-2,7-dione;

N-[(2R,3R,5S)-2-(5-amino-2,7-dioxo-6H-thiazolo[4,5-d]pyrimidin-3-yl)-5-(hydroxymethyl)tetrahydrofuran-3-yl] methanesulfonamide;

N-[(2R,3R,5S)-2-(5-amino-2,7-dioxo-6H-thiazolo[4,5-d]pyrimidin-3-yl)-5-(hydroxymethyl)tetrahydrofuran-3-yl] acetamide;

5-Amino-3-[(2R,3R,5S)-5-(hydroxymethyl)-3-morpholino-tetrahydrofuran-2-yl]-6H-thiazolo[4,5-d]pyrimidine-2,7-dione;

5-Amino-3-[(2R,3R,5S)-5-(hydroxymethyl)-3-(1-piperidyl)tetrahydrofuran-2-yl]-6H-thiazolo[4,5-d]pyrimidine-2,7-dione;

5-Amino-3-[(2R,3R,5S)-3-(dimethylamino)-5-(hydroxymethyl)tetrahydrofuran-2-yl]-6H-thiazolo[4,5-d]pyrimidine-2,7-dione;

(2R,3S,5S)-2-(5-amino-2,7-dioxo-6H-thiazolo[4,5-d]pyrimidin-3-yl)-5-(hydroxymethyl)tetrahydrofuran-3-carbonitrile;

5-Amino-3-[(2R,3R,5S)-5-(hydroxymethyl)-3-methylsulfanyl-tetrahydrofuran-2-yl]-6H-thiazolo[4,5-d]pyrimidine-2,7-dione;

5-Amino-3-[(2R,3R,5S)-3-(1-fluoro-1-methyl-ethyl)-5-(hydroxymethyl)tetrahydrofuran-2-yl]-6H-thiazolo[4,5-d]pyrimidine-2,7-dione;

5-Amino-3-[(2R,3R,5S)-5-(hydroxymethyl)-3-(2-methylallyl)tetrahydrofuran-2-yl]-6H-thiazolo[4,5-d]pyrimidine-2,7-dione and [(1S)-1-[(2S,4R,5R)-5-(5-Amino-2,7-dioxo-6H-thiazolo[4,5-d]pyrimidin-3-yl)-4-hydroxy-tetrahydrofuran-2-yl]propyl] 2-methylpropanoate;

or pharmaceutically acceptable salt, enantiomer or diastereomer thereof.

Another embodiment of present invention is that (xx) more particular compounds of formula (I) or (Ia) are the following:

5-Amino-3-[(2R,3R,5S)-3-hydroxy-5-(1-hydroxypropyl) tetrahydrofuran-2-yl]-6H-thiazolo[4,5-d]pyrimidine-2,7-dione;

5-Amino-3-[(2R,3R,5S)-3-hydroxy-5-(1-hydroxybutyl)tetrahydrofuran-2-yl]-6H-thiazolo[4,5-d]pyrimidine-2,7-dione;

5-Amino-3-[(2R,3R,5S)-5-[cyclopropyl(hydroxy)methyl]-3-hydroxy-tetrahydrofuran-2-yl]-6H-thiazolo[4,5-d]pyrimidine-2,7-dione;

5-Amino-3-[(2R,3R,5S)-3-hydroxy-5-(1-hydroxyprop-2-ynyl)tetrahydrofuran-2-yl]-6H-thiazolo[4,5-d]pyrimidine-2,7-dione;
5-Amino-3-[(2R,3R,5S)-3-hydroxy-5-(1-hydroxybut-2-ynyl)tetrahydrofuran-2-yl]-6H-thiazolo[4,5-d]pyrimidine-2,7-dione;
5-Amino-3-[(2R,3R,5S)-5-(1-hydroxypropyl)-3-methylsulfanyl-tetrahydrofuran-2-yl]-6H-thiazolo[4,5-d]pyrimidine-2,7-dione;
5-Amino-3-[(2R,3R,5S)-3-azido-5-(1-hydroxypropyl)tetrahydrofuran-2-yl]-6H-thiazolo[4,5-d]pyrimidine-2,7-dione;
5-Amino-3-[(2R,3R,5S)-3-hydroxy-5-(1-hydroxyallyl)tetrahydrofuran-2-yl]-6H-thiazolo[4,5-d]pyrimidine-2,7-dione;
3-[(2R,3R,5S)-3-allyl-5-(1-hydroxypropyl)tetrahydrofuran-2-yl]-5-amino-6H-thiazolo[4,5-d]pyrimidine-2,7-dione;
5-amino-3-[(2R,3R,5S)-5-[(1S)-1-hydroxypropyl]-3-propyl-tetrahydrofuran-2-yl]-6H-thiazolo[4,5-d]pyrimidine-2,7-dione;
5-amino-3-[(2R,3R,5S)-5-[(1R)-1-hydroxypropyl]-3-propyl-tetrahydrofuran-2-yl]-6H-thiazolo[4,5-d]pyrimidine-2,7-dione;
5-amino-3-[(2R,3R,5S)-5-[(1S)-1-hydroxypropyl]-3-methyl-tetrahydrofuran-2-yl]-6H-thiazolo[4,5-d]pyrimidine-2,7-dione;
5-Amino-3-[(2R,3R,5S)-5-[(1S)-1-hydroxybut-2-yl]-3-methyl-tetrahydrofuran-2-yl]-6H-thiazolo[4,5-d]pyrimidine-2,7-dione;
5-Amino-3-[(2R,3R,5S)-5-[(S)-cyclopropyl(hydroxy)methyl]-3-methyl-tetrahydrofuran-2-yl]-6H-thiazolo[4,5-d]pyrimidine-2,7-dione;
5-Amino-3-[(2R,3R,5S)-5-[(1S)-1-hydroxyethyl]-3-methyl-tetrahydrofuran-2-yl]-6H-thiazolo[4,5-d]pyrimidine-2,7-dione;
5-Amino-3-[(2R,3R,5S)-5-(hydroxymethyl)-3-pyrrolidin-1-yl-tetrahydrofuran-2-yl]-6H-thiazolo[4,5-d]pyrimidine-2,7-dione;
5-Amino-3-[(2R,3R,5S)-5-(hydroxymethyl)-3-methylsulfanyl-tetrahydrofuran-2-yl]-6H-thiazolo[4,5-d]pyrimidine-2,7-dione;
and [(1S)-1-[(2S,4R,5R)-5-(5-Amino-2,7-dioxo-6H-thiazolo[4,5-d]pyrimidin-3-yl)-4-hydroxy-tetrahydrofuran-2-yl]propyl] 2-methylpropanoate;
or pharmaceutically acceptable salt, enantiomer or diastereomer thereof.

Another embodiment of present invention is (xxi) a compound of formula (II),

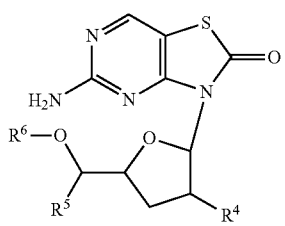

(II)

wherein
$R^4$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, ($C_{1-6}$alkyl)$_2$N—, $C_{1-6}$alkylcarbonyl-NH— or heterocyclic amino;
$R^5$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^6$ is hydrogen or $C_{1-6}$alkylcarbonyl;
or pharmaceutically acceptable salt, enantiomer or diastereomer thereof;
with the proviso that 5-amino-3-[3-hydroxy-5-(hydroxymethyl)tetrahydrofuran-2-yl]thiazolo[4,5-d]pyrimidin-2-one; [2-(5-amino-2-oxo-thiazolo[4,5-d]pyrimidin-3-yl)-5-(hydroxymethyl)tetrahydrofuran-3-yl]acetate; [4-acetoxy-5-(5-amino-2-oxo-thiazolo[4,5-d]pyrimidin-3-yl)tetrahydrofuran-2-yl]methyl acetate and their diastereomers are excluded.

A further embodiment of present invention is (xxii) a compound of formula (II), wherein
$R^4$ is hydroxy, methyl, n-propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;
$R^5$ is hydrogen, methyl, ethyl, propyl, butyl, cyclopropyl, cyclopentyl, vinyl, allyl, benzyl, ethynyl, 1-propynyl, methoxymethyl or thiophenyl;
$R^6$ is hydrogen, acetyl or isobutyryl;
or pharmaceutically acceptable salt, enantiomer or diastereomer thereof.

Another embodiment of present invention is (xxiii) a compound of formula (IIa),

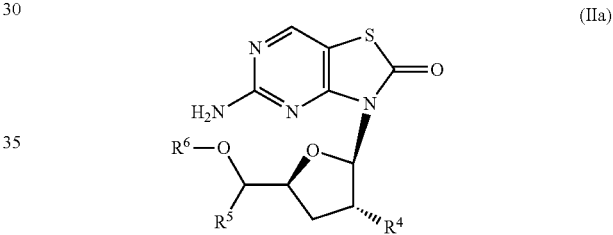

(IIa)

wherein
$R^4$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, ($C_{1-6}$alkyl)$_2$N—, $C_{1-6}$alkylcarbonyl-NH— or heterocyclic amino;
$R^5$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^6$ is hydrogen or $C_{1-6}$alkylcarbonyl;
or pharmaceutically acceptable salt, enantiomer or diastereomer thereof;
with the proviso that 5-amino-3-[3-hydroxy-5-(hydroxymethyl)tetrahydrofuran-2-yl]thiazolo[4,5-d]pyrimidin-2-one; [2-(5-amino-2-oxo-thiazolo[4,5-d]pyrimidin-3-yl)-5-(hydroxymethyl)tetrahydrofuran-3-yl]acetate; [4-acetoxy-5-(5-amino-2-oxo-thiazolo[4,5-d]pyrimidin-3-yl)tetrahydrofuran-2-yl]methyl acetate and their diastereomers are excluded.

A further embodiment of present invention is (xiv) a compound of formula (IIa), wherein
$R^4$ is hydroxy, methyl, n-propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;
$R^5$ is hydrogen, methyl, ethyl, propyl, butyl, cyclopropyl, cyclopentyl, vinyl, allyl, benzyl, ethynyl, 1-propynyl, methoxymethyl or thiophenyl;
$R^6$ is hydrogen, acetyl or isobutyryl;

or pharmaceutically acceptable salt, enantiomer or diastereomer thereof.

Another embodiment of present invention is (xxv) a compound of formula (II) or (IIa), wherein $R^4$ is hydroxy, $C_{1-6}$alkyl, $C_{1-6}$alkyl-S—, azido or $C_{2-6}$alkenyl;

$R^5$ is $C_{1-6}$alkyl, $C_{3-7}$cycloalkyl, $C_{2-6}$alkynyl or $C_{2-6}$alkenyl;

$R^6$ is hydrogen or $C_{1-6}$alkylcarbonyl;

or pharmaceutically acceptable salt, enantiomer or diastereomer thereof.

A further embodiment of present invention is (xxvi) a compound of formula (II) or (IIa), wherein $R^4$ is hydroxy, methyl, propyl, methylsulfanyl, azido or allyl;

$R^5$ is methyl, ethyl, propyl, cyclopropyl, vinyl, ethynyl or 1-propynyl;

$R^6$ is hydrogen or isobutyryl;

or pharmaceutically acceptable salt, enantiomer or diastereomer thereof.

A further embodiment of present invention is (xxvii) a compound of formula (II) or (IIa), wherein $R^4$ is hydroxy or $C_{1-6}$alkylcarbonyl-O—;

$R^5$ is $C_{1-6}$alkyl or $C_{3-7}$cycloalkyl;

$R^6$ is hydrogen or $C_{1-6}$alkylcarbonyl;

or pharmaceutically acceptable salt, enantiomer or diastereomer thereof

A further embodiment of present invention is (xxviii) a compound of formula (II) or (IIa), wherein $R^4$ is hydroxy or acetyloxy;

$R^5$ is ethyl or cyclopropyl;

$R^6$ is hydrogen or acetyl;

or pharmaceutically acceptable salt, enantiomer or diastereomer thereof.

Another embodiment of present invention is that (xxix) particular compounds of formula (II) or (IIa) are the following:

5-Amino-3-[(2R,3R,5S)-3-hydroxy-5-(1-hydroxypropyl) tetrahydrofuran-2-yl]thiazolo[4,5-d]pyrimidin-2-one;

[(2R,3R,5S)-2-(5-amino-2-oxo-thiazolo[4,5-d]pyrimidin-3-yl)-5-(1-hydroxypropyl)tetrahydrofuran-3-yl]acetate;

1-[(2S,4R,5R)-5-(5-amino-2-oxo-thiazolo[4,5-d]pyrimidin-3-yl)-4-hydroxy-tetrahydrofuran-2-yl]propyl acetate;

[(S)-[(2S,4R,5R)-5-(5-amino-2-oxo-thiazolo[4,5-d]pyrimidin-3-yl)-4-hydroxy-tetrahydrofuran-2-yl]-cyclopropyl-methyl]acetate;

and 5-Amino-3-[(2R,3R,5S)-5-[cyclopropyl(hydroxy)methyl]-3-hydroxy-tetrahydrofuran-2-yl]thiazolo[4,5-d]pyrimidin-2-one;

or pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^{11}$ are as defined above unless otherwise indicated. Furthermore, and unless explicitly otherwise stated, all reactions, reaction conditions, abbreviations and symbols have the meanings well known to a person of ordinary skill in organic chemistry.

Scheme 1

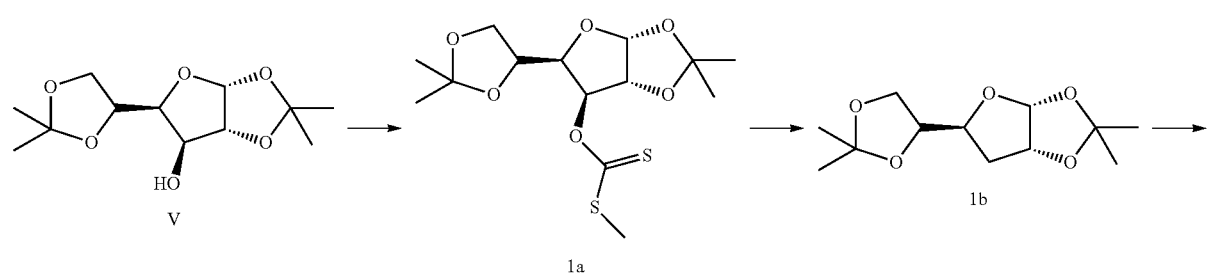

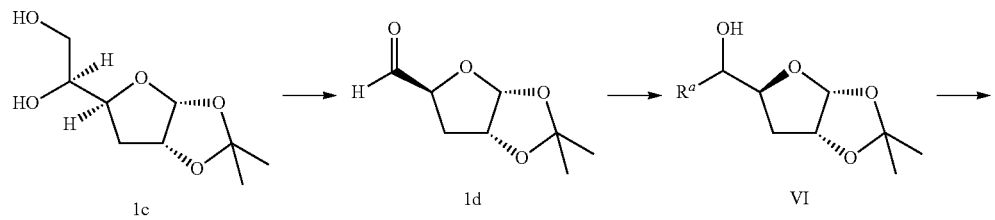

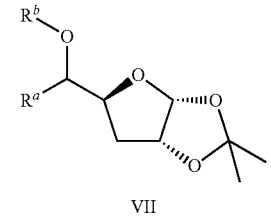

VII

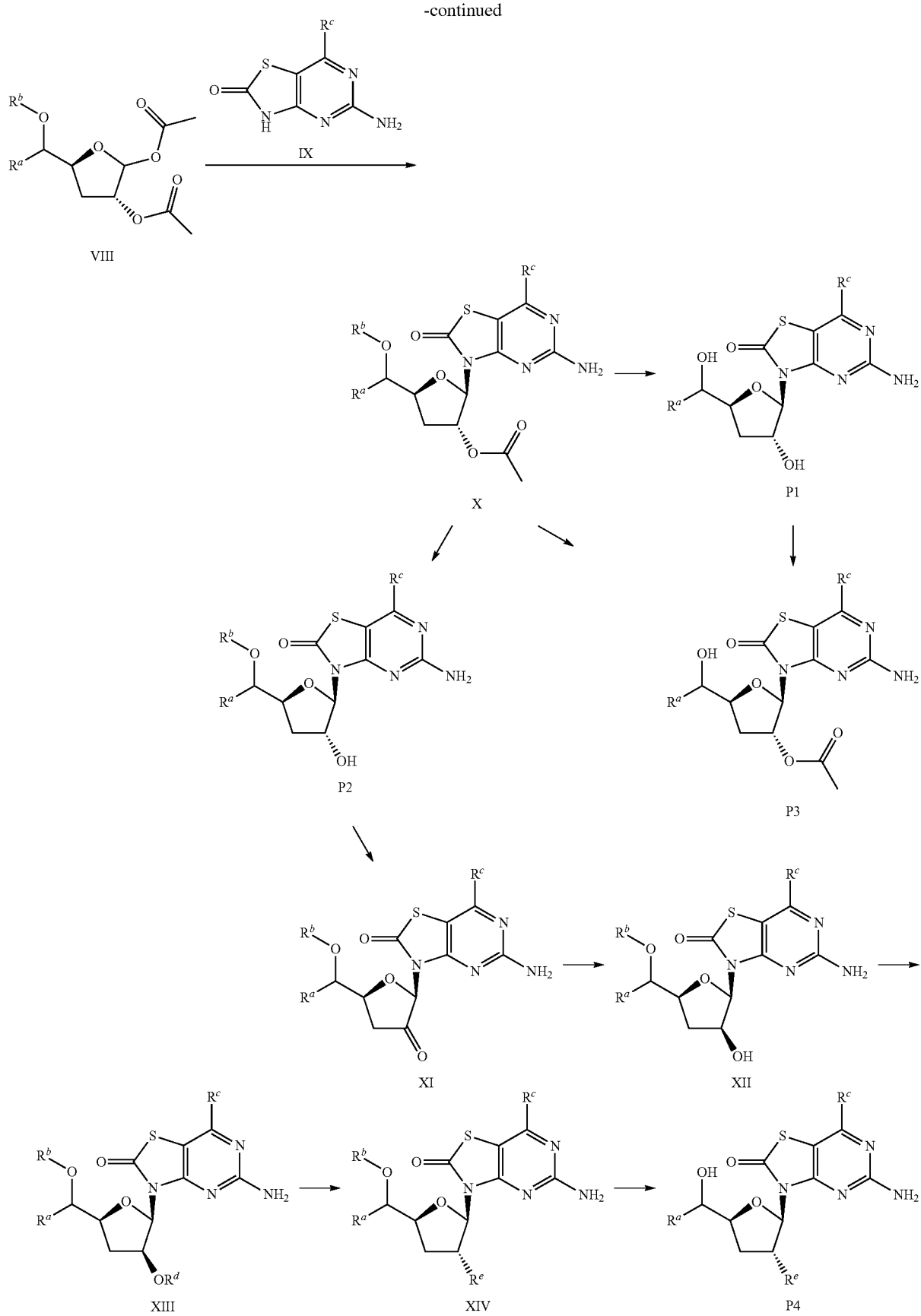

$R^a$ is $R^2$ or $R^5$; $R^b$ is acyl, benzoyl, tert-butyl(dimethyl)silyl or tert-butyl(diphenyl)silyl; $R^c$ is hydrogen or hydroxy; $R^d$ is trifluoromethylsulfonyl or p-tolylsulfonyl; $R^e$ is $R^1$ or $R^4$.

Treatment of compound V with carbon disulfide and iodomethane in the presence of an appropriate base, such as NaH, affords methylsulfanyl methanethioate 1a. Deoxylation of methylsulfanylmethanethioate 1a with an appropriate reagent, such as tri-n-butyltin hydride affords 1b. Deprotection of 1b with an appropriate acid, such as acetic acid, affords diol 1c. Oxidation of 1c with oxidant, such as sodium metaperiodate, gives aldehyde 1d. Treatment of aldehyde 1d with an appropriate nucleophile reagent, such as Grignard reagent, gives alcohol VI. Protection of alcohol VI with an appropriate acid anhydride or acid chloride, such as acetic chloride or benzoyl anhydride, affords ester VII. Treatment of ester VII with acetic acid and acetic anhydride in the presence of an appropriate acid, such as condensed sulfuric acid, affords ester VIII. Coupling of ester VIII and IX in the presence of an appropriate silicon etherification agent, such as N,O-bis(trimethylsilyl)acetamide, and Lewis acid, such as TMSOTf, gives the intermediate X. Deprotection of intermediate X with appropriate reagent, such as $K_2CO_3$ or TBAF, and purification by preparative HPLC affords desired compounds P1, P2 or P3. Protection of compound P1 with an appropriate acid anhydride or acid chloride, such as acetic chloride or acetic anhydride, affords compound P3. Oxidation of P2 with an appropriate oxidant, such as Dess-Martin periodinane, affords ketone XI. Reduction of ketone XI with an appropriate reductant, such as tert-butoxyaluminum hydride, affords alcohol XII. Treatment of alcohol XII with sulfonic anhydride or sulfonyl chloride affords intermediate XIII. Treatment of intermediate XIII with an appropriate nucleophile reagent, such as sodium azide, affords compound XIV. Deprotection of XIV with an appropriate base, such as $K_2CO_3$, or an appropriate fluoride reagent, such as TBAF, and purification by preparative HPLC affords compound P4.

Scheme 2:

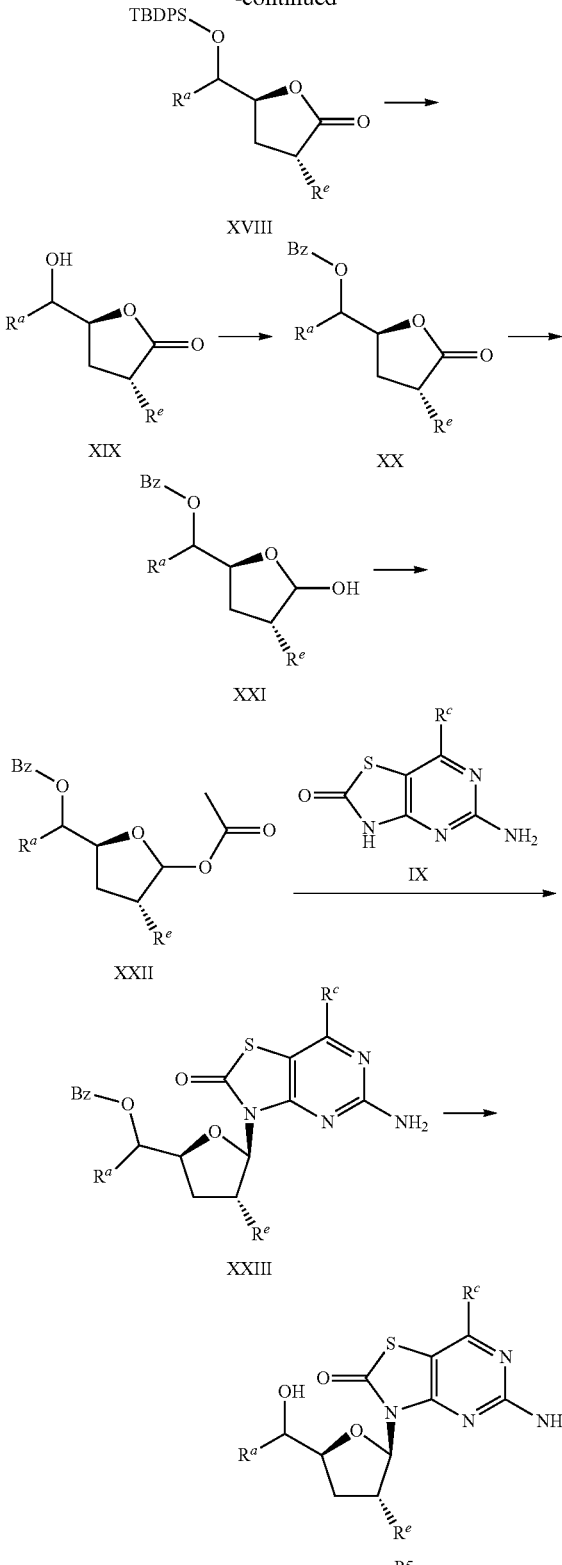

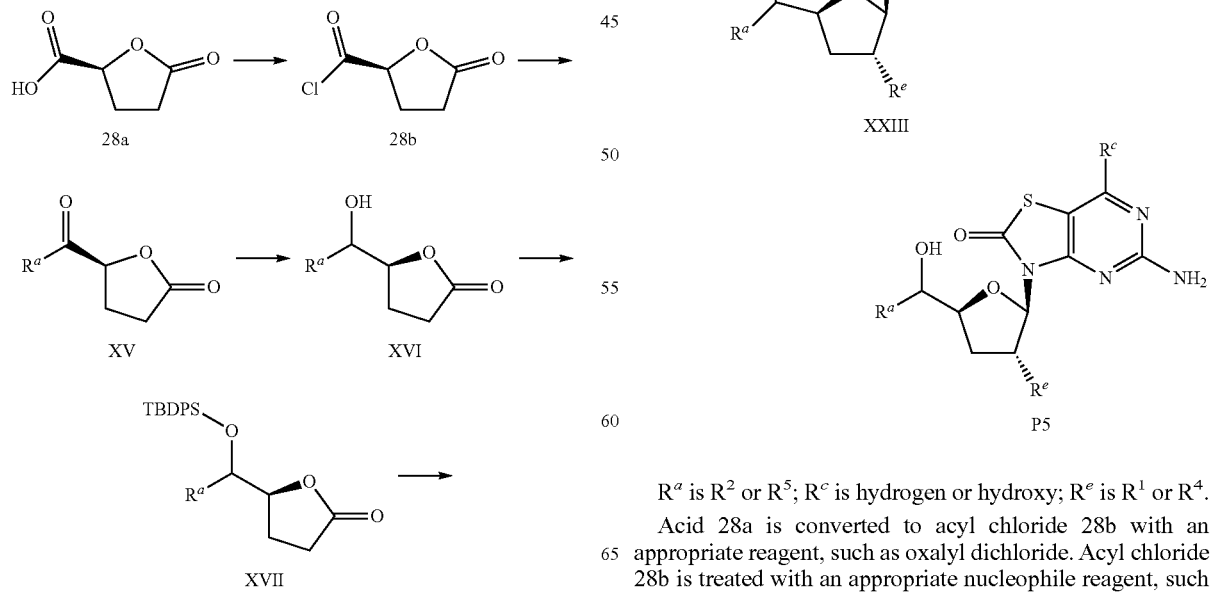

$R^a$ is $R^2$ or $R^5$; $R^c$ is hydrogen or hydroxy; $R^e$ is $R^1$ or $R^4$.

Acid 28a is converted to acyl chloride 28b with an appropriate reagent, such as oxalyl dichloride. Acyl chloride 28b is treated with an appropriate nucleophile reagent, such as Grignard reagent, to afford ketone XV. Reduction of ketone XV with an appropriate reductant, such as L-selectride, affords alcohol XVI. Protection of XVI with tert-butylchlorodiphenylsilane gives intermediate XVII. Alkylation of XVII with an alkylating reagent, such as iodomethane, in the presence of an appropriate base, such as lithium diisopropylamide, affords intermediate XVIII. Deprotection of XVIII with an appropriate reagent, such as TBAF, affords alcohol XIX. Protection of alcohol XIX with benzoyl chloride affords ester XX. Reduction of ester XX with an appropriate reductant, such as diisobutyl aluminium hydride, affords alcohol XXI. Esterification of alcohol XXI with acetic chloride or acetic anhydride affords XXII. Coupling of XXII and IX in the presence of an appropriate silicon etherification agent such as N, O-bis(trimethylsilyl)acetamide and Lewis acid gives XXIII. Deprotection of XXIII with an appropriate base, such as K$_2$CO$_3$, and purification by preparative HPLC affords compound P5.

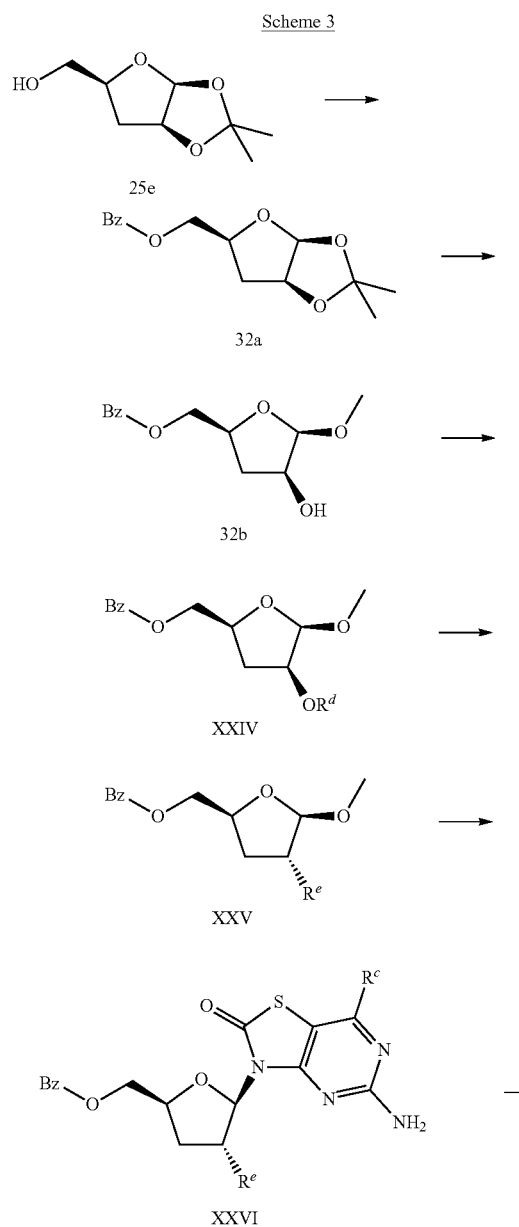

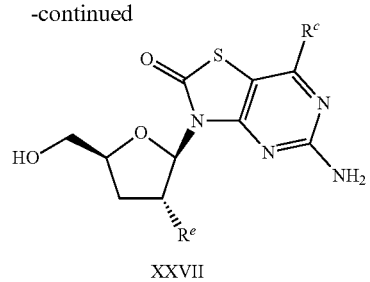

XXVII

R$^c$ is hydrogen or hydroxy; R$^d$ is trifluoromethylsulfonyl or p-tolylsulfonyl; R$^e$ is R$^1$ or R$^4$.

Protection of alcohol 25e with benzoyl chloride affords intermediate 32a. Deprotection of 32a with an appropriate acid, such as hydrochloride, in the presence of an appropriate solvent, such as methanol, affords intermediate 32b. Treatment of 32b with with sulfonic anhydride or sulfonyl chloride affords intermediate XXIV. Treatment of XXIV with a nucleophile reagent, such as sodium azide and amines, affords intermediate XXV. Coupling of XXV and IX in the presence of an appropriate silicon etherification agent such as N, O-bis(trimethylsilyl)acetamide and Lewis acid gives XXVI. Deprotection of XXVI with an appropriate base, such as K$_2$CO$_3$, and purification by preparative HPLC affords compound XXVII.

Scheme 4:

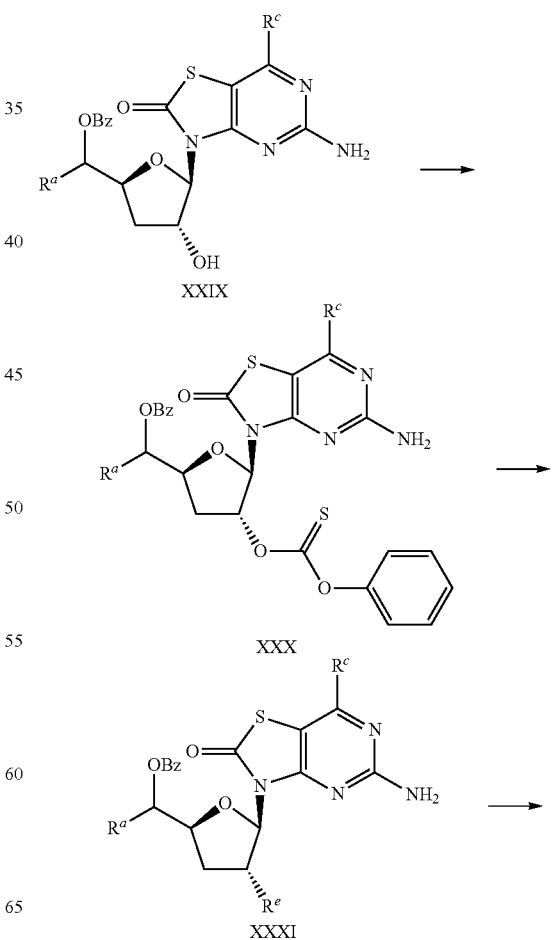

-continued

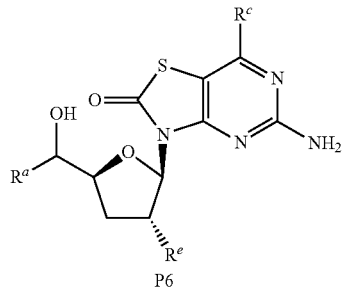
(P6)

$R^a$ is $R^2$ or $R^5$; $R^c$ is hydrogen or hydroxy; $R^e$ is $R^1$ or $R^4$.

Treatment of XXIX with an appropriate reagent, such as 0-phenyl chloromethanethioate, in the presence of an appropriate base, such as DMAP, affords intermediate XXX. Treatment of intermediate XXX with organostannane reagent, such as allyl(tri-n-butyl)stannane, affords intermediate XXXI. Deprotection of XXXI with an appropriate base, such as $K_2CO_3$, and purification by preparative HPLC affords compound P6.

This invention also relates to a process for the preparation of a compound of formula (I), (Ia), (II) or (IIa) comprising the reaction of:

(a) the reaction of a compound of formula (X),

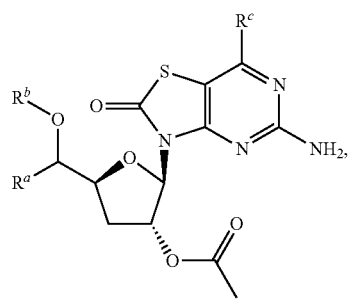
(X)

with a base or fluoride reagent, wherein $R^a$ is $R^2$ or $R^5$; $R^b$ is acyl, benzoyl, tert-butyl(dimethyl)silyl or tert-butyhdiphenyl)silyl; $R^c$ is hydrogen or hydroxy;

(b) the reaction of a compound of formula (P1),

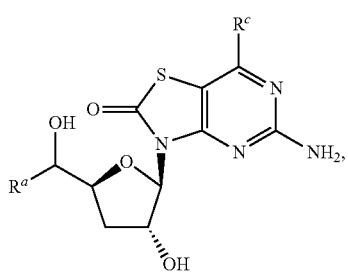
(P1)

with an acid anhydride or acid chloride, wherein $R^a$ is $R^2$ or $R^5$; $R^c$ is hydrogen or hydroxy;

(c) the reaction of a compound of formula (XIV),

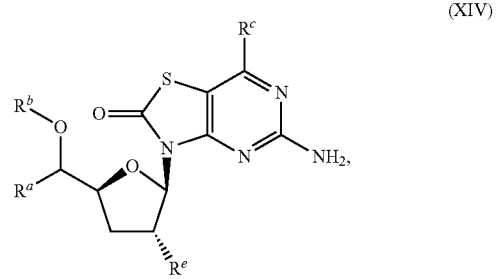
(XIV)

with a base or a fluoride reagent, wherein $R^a$ is $R^2$ or $R^5$; $R^b$ is acyl, benzoyl, tert-butyl(diphenyl)silyl; $R^c$ is hydrogen or hydroxy; $R^d$ is trifluoromethylsulfonyl or p-tolylsulfonyl; $R^e$ is $R^1$ or $R^4$;

(d) the reaction of a compound of formula (XXIII),

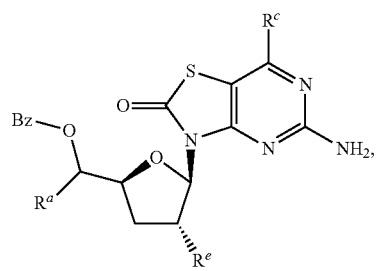
(XXIII)

with a base, wherein $R^a$ is $R^2$ or $R^5$; $R^c$ is hydrogen or hydroxy; $R^e$ is $R^1$ or $R^4$;

(e) the reaction of a compound of formula (XXVI),

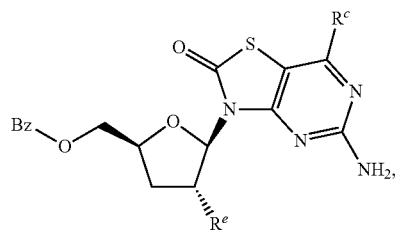
(XXVI)

with a base, wherein $R^c$ is hydrogen or hydroxy; $R^e$ is $R^1$ or $R^4$;

(f) the reaction of a compound of formula (XXXI),

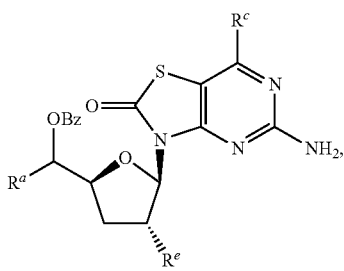
(XXXI)

with a base, wherein $R^a$ is $R^2$ or $R^5$; $R^c$ is hydrogen or hydroxy; $R^e$ is $R^1$ or $R^4$; or wherein $R^a$, $R^b$, $R^c$, $R^d$, $R^e$, $R^1$, $R^2$, $R^3$, $R^4$, $R^5$ and $R^6$ are defined above.

In step (a), the base can be for example $K_2CO_3$, the fluoride reagent can be for example TBAF.

In step (b), the acid anhydride or acid chloride can be for example acetic chloride or acetic anhydride.

In step (c), (d), (e) and (f), the base can be for example $K_2CO_3$, the fluoride reagent can be for example TBAF.

A compound of formula (I), (Ia), (II) and (IIa) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) or (Ia) or their prodrugs may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or (Ia) or their prodrugs are formulated in an acetate buffer, at pH 5. In another embodiment, the compounds of formula (I) or (Ia) or their prodrugs are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 receptor and lead to produce INF-α and other cytokines, which can be used, but not limited, for the treatment or prevention of hepatitis B and/or C viral infected patients.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or (Ia) or their prodrugs, formula (II) or (IIa), or pharmaceutically acceptable salts or enantiomers or diastereomers thereof.

In a further embodiment includes a pharmaceutical composition comprising a compound of formula (I) or (Ia) or their prodrugs, formula (II) or (IIa), or pharmaceutically acceptable salts or enantiomers or diastereomers thereof, together with a pharmaceutically acceptable carrier or excipient.

Another embodiment includes a pharmaceutical composition comprising a compound of formula (I) or (Ia) or their prodrugs, formula (II) or (IIa), or pharmaceutically acceptable salts or enantiomers or diastereomers thereof for use in the treatment of hepatitis B virus infection.

Indications and Methods of Treatment

The present invention provides methods for treating or preventing a hepatitis B viral infection and/or hepatitis C viral infection in a patient in need thereof.

The present invention further provides methods for introducing a therapeutically effective amount of a formula (I) or (Ia) compounds or their prodrugs, or other compounds of the invention into the blood stream of a patient in the treatment and/or prevention of hepatitis B and/or C viral infection.

The methods of the present invention are particularly well suited for human patients. In particular, the methods and doses of the present invention can be useful for, but not limited to, HBV and/or HCV infected patients. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing hepatitis B viral infection and/or hepatitis C viral infection in a mammal in need of such treatment, wherein the method comprises administering to said mammal a therapeutically effective amount of a compound of formula (I) or (Ia), or enantiomers, diastereomers, prodrugs or pharmaceutically acceptable salts thereof.

EXAMPLES

Figure 1:
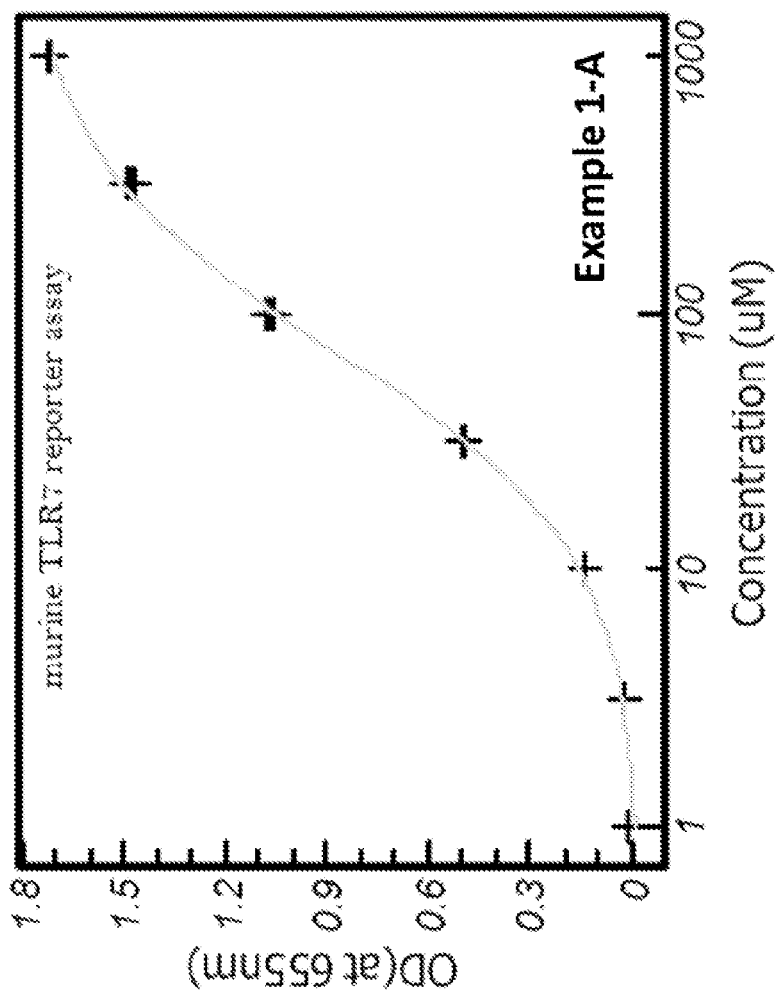
FIG. 1: Example 1-A activates murine TLR7 in a HEK-Blue-mTLR assay. The cells were incubated with Example 1-A and a positive control GS-9620 at indicated concentrations for 20 hours. The activation of murine TLR7 was measured using a Quanti-Blue assay.

The invention will be more fully understood by reference to the following examples. They should not, however, be construed as limiting the scope of the invention.

ABBREVIATIONS

ACN: acetonitrile
DMAP: 4-dimethylaminopyridine
$CDCl_3$: deuterated chloroform
DCM: dichloromethane
DMF: dimethyl formamide
EtOAc: ethyl acetate
FBS: fetal bovine serum
HPLC: high performance liquid chromatography
MS (ESI): mass spectroscopy (electron spray ionization)
BSA: N,O-bis(trimethylsilyl)acetamide
NMR: nuclear magnetic resonance
obsd. observed
$NaBH_4$: sodium borohydride TBAF: tetrabutylammonium fluoride
$EC_{50}$: The molar concentration of an agonist, which produces 50% of the maximum possible response for that agonist.
TEA: triethylamine
TMSOTf: trimethylsilyl trifluoromethanesulfonate

GENERAL EXPERIMENTAL CONDITIONS

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in $H_2O$; B: 0.1% formic acid in acetonitrile;

Basic condition: A: 0.05% $NH_3.H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Example 1

5-Amino-3-[(2R,3R,5S)-3-hydroxy-5-(1-hydroxypropyl)tetrahydrofuran-2-yl]-6H-thiazolo[4,5-d]pyrimidine-2,7-dione

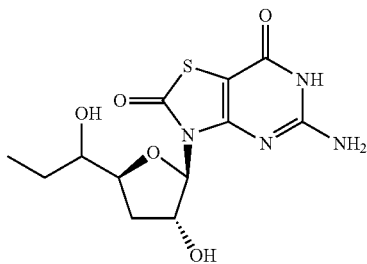

Preparation of O-[(3aR,5R,6S,6aR)-5-(2,2-dimethyl-1,3-dioxolan-4-yl)-2,2-dimethyl-3a,5,6,6a-tetrahydrofuro[2,3-d][1,3]dioxol-6-yl] methylsulfanylmethanethioate

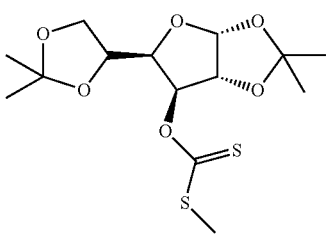

1a

To a suspension of NaH (60% in mineral oil, 4 g, 100 mmol) in THF (80 mL) was added a solution of diacetone-α-D-glucose (10.5 g, 40 mmol) and imidazole (136 mg, 2 mmol) in THF (20 mL) dropwise while keeping inner temperature below 15° C. The formed mixture was stirred at 10° C. for 15 minutes. To the previous mixture was added carbon disulfide (14.8 g, 200 mmol) and the reaction mixture was stirred at room temperature for 1 hour. The reaction mixture was added iodomethane (24.6 g, 200 mmol) and stirred at room temperature for another 2 hours, then quenched by saturated NH$_4$Cl solution (70 mL) and extracted with EtOAc (100 mL) twice. The combined organic layers were dried over Na$_2$SO$_4$ and concentrated in vacuo. The residue was purified by column chromatography on silica gel (eluting with 1:10 EtOAc in petroleum ether) to afford 14.6 g of O-[(3aR,5R,6S,6aR)-5-(2,2-dimethyl-1,3-dioxolan-4-yl)-2,2-dimethyl-3a,5,6,6a-tetrahydrofuro[2,3-d][1,3]dioxol-6-yl] methylsulfanylmethanethioate (compound 1a) as a colorless oil.

Compound 1a: $^1$H NMR (400 MHz, CDCl$_3$) δ ppm: 5.89-5.97 (m, 2H), 4.65-4.73 (m, 1H), 4.29-4.39 (m, 2H), 4.04-4.17 (m, 2H), 2.61 (s, 3H), 1.56 (s, 3H), 1.44 (s, 3H), 1.35 (d, J=4.02 Hz, 6H).

Preparation of (3aR,5S,6aR)-5-(2,2-dimethyl-1,3-dioxolan-4-yl)-2,2-dimethyl-3a,5,6,6a-tetrahydrofuro[2,3-d][1,3]dioxole

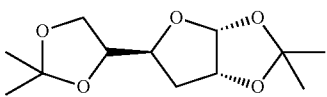

1b

To a solution of O-[(3aR,5R,6S,6aR)-5-(2,2-dimethyl-1,3-dioxolan-4-yl)-2,2-dimethyl-3a,5,6,6a-tetrahydrofuro[2,3-d][1,3]dioxol-6-yl] methylsulfanylmethanethioate (compound 1a, 14 g, 40 mmol) in toluene was added tri-n-butyltin hydride(23.2 g, 80 mmol) and azodiisobutyronitrile (82 mg, 0.5 mmol), the formed mixture was heated at 130° C. under nitrogen for 3 hours. After the reaction was completed, the reaction mixture was concentrated in vacuo and the residue was purified by column chromatography on silica gel (eluting with 1:10 EtOAc in petroleum ether) to afford 8.2 g of (3aR,5S,6aR)-5-(2,2-dimethyl-1,3-dioxolan-4-yl)-2,2-dimethyl-3a,5,6,6a-tetrahydrofuro[2,3-d][1,3]dioxole (compound 1b) as an oil.

Compound 1b: $^1$H NMR (400 MHz, CDCl$_3$) δ ppm: 5.82 (d, J=3.76 Hz, 1H), 4.73-4.80 (m, 1H), 4.12 (m, 3H), 3.78-3.88 (m, 1H), 2.15-2.24 (m, 1H), 1.73-1.83 (m, 1H), 1.52 (s, 3H), 1.43 (s, 3H), 1.36 (s, 3H), 1.32 (s, 3H). MS obsd. (ESI$^+$) [(M+NH$_4$)$^+$]: 262.

Preparation of (1S)-1-[(3aR,5S,6aR)-2,2-dimethyl-3a,5,6,6a-tetrahydrofuro[2,3-d][1,3]dioxol-5-yl]ethane-1,2-diol

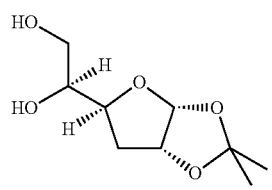

1c

A solution of (3aR,5S,6aR)-5-(2,2-dimethyl-1,3-dioxolan-4-yl)-2,2-dimethyl-3a,5,6,6a-tetrahydrofuro[2,3-d][1,3]dioxole (compound 1b, 10.0 g, 40.9 mmol) in 60% HOAc in water (20 mL) was stirred at 40° C. for 16 hours. The reaction mixture was adjusted to pH 8~8.5 by saturated NaHCO$_3$ solution and extracted with EtOAc. The organic layer was combined and concentrated, the residue was purified by column chromatography on silica gel (eluting with 1:2 EtOAc in petroleum ether) to afford 5.2 g of (1S)-1-[(3aR,5S,6aR)-2,2-dimethyl-3a,5,6,6a-tetrahydrofuro[2,3-d][1,3]dioxol-5-yl]ethane-1,2-diol (compound 1c). MS obsd. (ESI$^+$) [(M+NH$_4$)$^+$]: 222.

Preparation of (3aR,5S,6aR)-2,2-dimethyl-3a,5,6,6a-tetrahydrofuro[2,3-d][1,3]dioxole-5-carbaldehyde

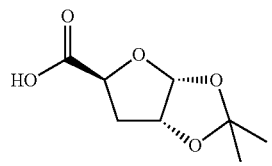

1d

To a solution of (1S)-1-[(3aR,5S,6aR)-2,2-dimethyl-3a,5,6,6a-tetrahydrofuro[2,3-d][1,3]dioxol-5-yl]ethane-1,2-diol (compound 1c, 18 g, 90 mmol) in the MeOH (250 mL) cooled in ice bath was added sodium metaperiodate (23.1 g, 108 mmol). After being stirred at room temperature for 12 hours, the resulting suspension was filtered. The filtrate was concentrated in vacuo. The residue was purified by column chromatography on silica gel (eluting with 1:2 EtOAc in petroleum ether) to afford 14 g of (3aR,5S,6aR)-2,2-dimethyl-3a,5,6,6a-tetrahydrofuro[2,3-d][1,3]dioxole-5-carbaldehyde (compound 1d). MS obsd. (ESI$^+$) [(M+NH$_4$)$^+$]: 190.

Preparation of 1-[(3aR,5S,6aR)-2,2-dimethyl-3a,5,6, 6a-tetrahydrofuro[2,3-d][1,3]dioxol-5-yl]propan-1-ol

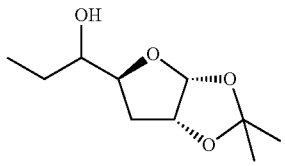

1e

To a solution of (3aR,5S,6aR)-2,2-dimethyl-3a,5,6,6a-tetrahydrofuro[2,3-d][1,3]dioxole-5-carbaldehyde (compound 1d, 296 mg, 2 mmol) in THF (20 mL) was added ethyl magnesium bromide (2M in THF, 2 mL, 2 mmol) at −20° C. under argon. After being stirred at −20° C. for 20 hours, the reaction was quenched by saturated NH₄Cl solution and extracted with EtOAc (30 mL) three times. The combined organic layers were concentrated in vacuo to afford the crude product of 1-[(3aR,5S,6aR)-2,2-dimethyl-3a,5,6,6a-tetrahydrofuro[2,3-d][1,3]dioxol-5-yl]propan-1-ol (compound 1e), which was used in next step without further purification. MS obsd. (ESI⁺) [(M+NH₄)⁺]: 316.

Preparation of [(3R,5S)-2-acetoxy-5-(1-acetoxypropyl)tetrahydrofuran-3-yl]acetate

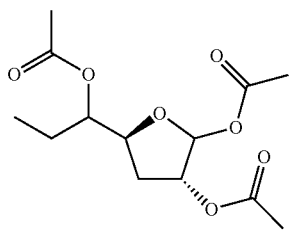

1f

To a solution of 1-[(3aR,5S,6aR)-2,2-dimethyl-3a,5,6,6a-tetrahydrofuro[2,3-d][1,3]dioxol-5-yl]propan-1-ol (compound 1e, crude as prepared above) in the mixture of acetic acid (2 mL) and acetic acid anhydride (2 mL) was added H₂SO₄ (0.2 mmol). After being stirred at room temperature for 24 hours, the solution was diluted by EtOAc (40 mL) and adjusted to pH 5.0 by saturated NaHCO₃ solution. The separated organic layer was washed with brine, dried over Na₂SO₄ and concentrated in vacuo. The residue was purified by column chromatography on silica gel (eluting with 1:3 EtOAc in petroleum ether) to afford 510 mg of [(3R,5S)-2-acetoxy-5-(1-acetoxypropyl)tetrahydrofuran-3-yl]acetate (compound 1f). MS obsd. (ESI⁺) [(M+NH₄)⁺]: 316.

Preparation of [(2R,3R,5S)-5-(1-acetoxypropyl)-2-(5-amino-2,7-dioxo-6H-thiazolo[4,5-d]pyrimidin-3-yl)tetrahydrofuran-3-yl]acetate

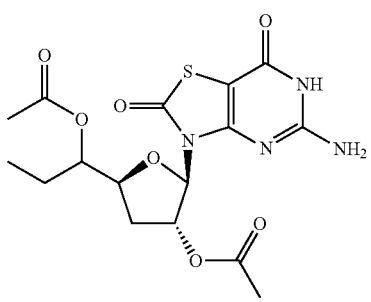

1g

To a suspension of 5-amino-3,6-dihydrothiazolo[4,5-d]pyrimidine-2,7-dione (CAS #: 30161-97-8, Cat.#: as J92-094790, commercially available from J&K Scientific, 276 mg, 1.5 mmol) in ACN (20 mL) was added BSA (913.5 mg, 4.5 mmol). The reaction mixture was stirred at 70° C. for 0.5 hour under argon to form a clear solution. After the solution was cooled to room temperature, [(3R,5S)-2-acetoxy-5-(1-acetoxypropyl)tetrahydrofuran-3-yl]acetate (compound 1f, 450 mg, 1.6 mmol) and TMSOTf (510 mg, 2.3 mmol) were added in sequence. After being heated at 70° C. for 14 hours, the solvent was evaporated in vacuo. The residue was partitioned between EtOAc and saturated NaHCO₃ solution (30 mL). The organic layer was collected and the aqueous phase was extracted with EtOAc (30 mL) twice. The combined organic layers were washed with brine, dried over Na₂SO₄ and concentrated in vacuo to afford 412 mg crude product of [(2R,3R,5S)-5-(1-acetoxypropyl)-2-(5-amino-2,7-dioxo-6H-thiazolo[4,5-d]pyrimidin-3-yl)tetrahydrofuran-3-yl] acetate (compound 1g), which was used in next step without purification. MS obsd. (ESI⁻) [(M−H)⁻]: 411.

Preparation of 5-amino-3-[(2R,3R,5S)-3-hydroxy-5-(1-hydroxypropyl)tetrahydrofuran-2-yl]-6H-thiazolo[4,5-d]pyrimidine-2,7-dione

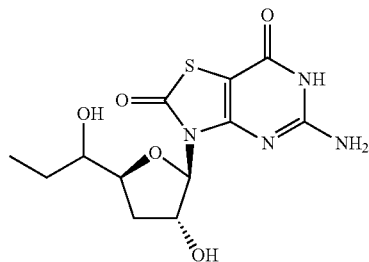

1

To a solution of [(2R,3R,5S)-5-(1-acetoxypropyl)-2-(5-amino-2,7-dioxo-6H-thiazolo[4,5-d]pyrimidin-3-yl)tetrahydrofuran-3-yl]acetate (compound 1g, crude, 412 mg) in methanol (25 mL) was added K₂CO₃ (272 mg, 2 mmol). After being stirred at room temperature for 12 hours, the reaction mixture was adjusted to pH 8.2 by addition of HOAc (120 mg, 2 mmol) and concentrated in vacuo. The residue was purified and separated by preparative HPLC to afford 133.1 mg of Example 1-A and 118.2 mg of Example 1-B as white solid.

Example 1-A: ¹H NMR (400 MHz, CD₃OD) δ ppm: 5.93-6.00 (m, 1H), 4.91-4.94 (m, 1H), 4.15-4.25 (m, 1H), 3.44-3.53 (m, 1H), 2.49-2.61 (m, 1H), 1.89-1.96 (m, 1H), 1.41-1.61 (m, 2H), 1.01 (t, J=7.40 Hz, 3H). MS obsd. (ESI⁻) [(M−H)⁻]: 327.

Example 1-B: ¹H NMR (400 MHz, CD₃OD) δ ppm: 5.89-5.96 (m, 1H), 4.90-4.97 (m, 1H), 4.09-4.20 (m, 1H), 3.61-3.69 (m, 1H), 2.57-2.68 (m, 1H), 1.91-1.96 (m, 1H), 1.55-1.65 (m, 1H), 1.35-1.46 (m, 1H), 1.00 (t, J=7.40 Hz, 3H). MS obsd. (ESI⁻) [(M−H)⁻]: 327.

Example 2

5-Amino-3-[(2R,3R,5S)-3-hydroxy-5-(1-hydroxypropyl)tetrahydrofuran-2-yl]thiazolo[4,5-d]pyrimidin-2-one

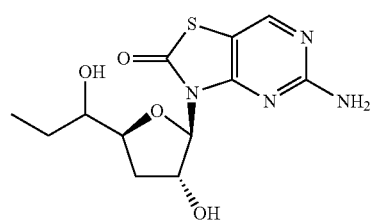

2

Preparation of [(2R,3R,5S)-5-(1-acetoxypropyl)-2-(5-amino-2-oxo-thiazolo[4,5-d]pyrimidin-3-yl)tetrahydrofuran-3-yl]acetate

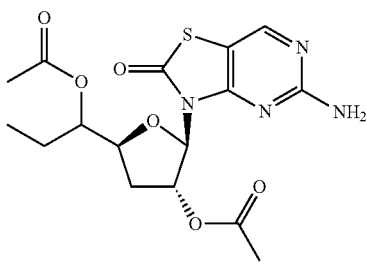

2a

To a suspension of 5-amino-3H-thiazolo[4,5-d]pyrimidin-2-one (CAS #: 848691-22-5, Cat.#: as SY028954, commercially available from Shanghai Shaoyuan Co. Ltd., 326 mg, 2 mmol) in ACN (40 mL) was added BSA (1.2 g, 6 mmol). The resulting reaction mixture was then stirred at 70° C. for 1 hour under argon to form a clear solution. After the solution was cooled to room temperature, [(3R,5S)-2-acetoxy-5-(1-acetoxypropyl)tetrahydrofuran-3-yl]acetate (compound 1f, 432 mg, 1.5 mmol) and TMSOTf (666 mg, 3 mmol) were added in sequence. After being heated with stirring at 70° C. for 14 hours, the solvent was evaporated in vacuo. The residue was partitioned between EtOAc and saturated NaHCO$_3$ solution (30 mL). The organic layer was separated and the aqueous phase was extracted with EtOAc (30 mL) twice. The combined organic layers were washed with brine, dried over Na$_2$SO$_4$ and concentrated in vacuo to afford crude [(2R,3R,5S)-5-(1-acetoxypropyl)-2-(5-amino-2-oxo-thiazolo[4,5-d]pyrimidin-3-yl)tetrahydrofuran-3-yl]acetate. The crude product was purified by column chromatography on silica gel (eluting with 1:1 EtOAc in petroleum ether) to afford 310 mg of [(2R,3R,5S)-5-(1-acetoxypropyl)-2-(5-amino-2-oxo-thiazolo[4,5-c]pyrimidin-3-yl)tetrahydrofuran-3-yl]acetate (compound 2a).

Preparation of 5-amino-3-[(2R,3R,5S)-3-hydroxy-5-(1-hydroxypropyl)tetrahydrofuran-2-yl]thiazolo[4,5-d]pyrimidin-2-one

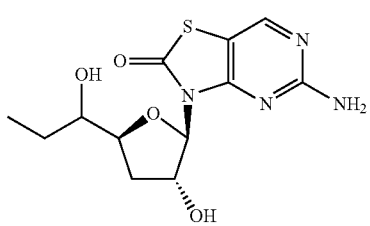

2

To a solution of [(2R,3R,5S)-5-(1-acetoxypropyl)-2-(5-amino-2-oxo-thiazolo[4,5-d]pyrimidin-3-yl)tetrahydrofuran-3-yl]acetate (compound 2a, 180 mg, 0.5 mmol) in methanol (25 mL) was added K$_2$CO$_3$ (136 mg, 1 mmol). After being stirred at room temperature for 2 hours, the reaction mixture was adjusted to pH 7.0 by addition of HOAc (120 mg, 2 mmol) and concentrated in vacuo. The residue was purified and separated by preparative HPLC to afford 9.5 mg of Example 2-A and 2.8 mg of Example 2-B as white solid.

Example 2-A: $^1$H NMR (400 MHz, d$_6$-DMSO) δ ppm: 8.35 (s, 1H), 6.85 (s, 2H), 5.81-5.87 (m, 1H), 5.43-5.52 (m, 1H), 4.73-4.81 (m, 1H), 4.48-4.59 (m, 1H), 3.95-4.05 (m, 1H), 3.27-3.32 (m, 1H), 2.31-2.41 (m, 1H), 1.69-1.78 (m, 1H), 1.36-1.48 (m, 1H), 1.18-1.33 (m, 1H), 0.88 (t, J=7.40 Hz, 3H). MS obsd. (ESI$^+$) [(M+H)$^+$]: 313.

Example 2-B: $^1$H NMR (400 MHz, d$_6$-DMSO) δ ppm: 8.35 (s, 1H), 6.84 (s, 2H), 5.79-5.88 (m, 1H), 5.37-5.54 (m, 1H), 4.77-4.86 (m, 1H), 4.52-4.62 (m, 1H), 3.87-4.01 (m, 1H), 3.30-3.34 (m, 1H), 2.39-2.49 (m, 1H), 1.86 (ddd, J=2.76, 6.21, 12.61 Hz, 1H), 1.49 (ddd, J=3.26, 7.47, 13.61 Hz, 1H), 1.14-1.28 (m, 1H), 0.86 (t, J=7.40 Hz, 3H). MS obsd. (ESI$^+$) [(M+H)$^+$]: 313.

Example 3

[(2R,3R,5S)-2-(5-amino-2-oxo-thiazolo[4,5-d]pyrimidin-3-yl)-5-(1-hydroxypropyl)tetrahydrofuran-3-yl]acetate

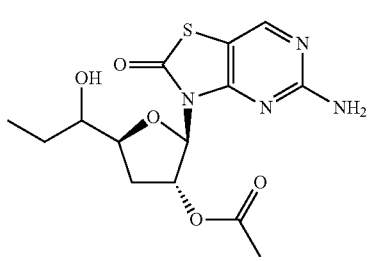

3

The title compound was prepared according to the following scheme:

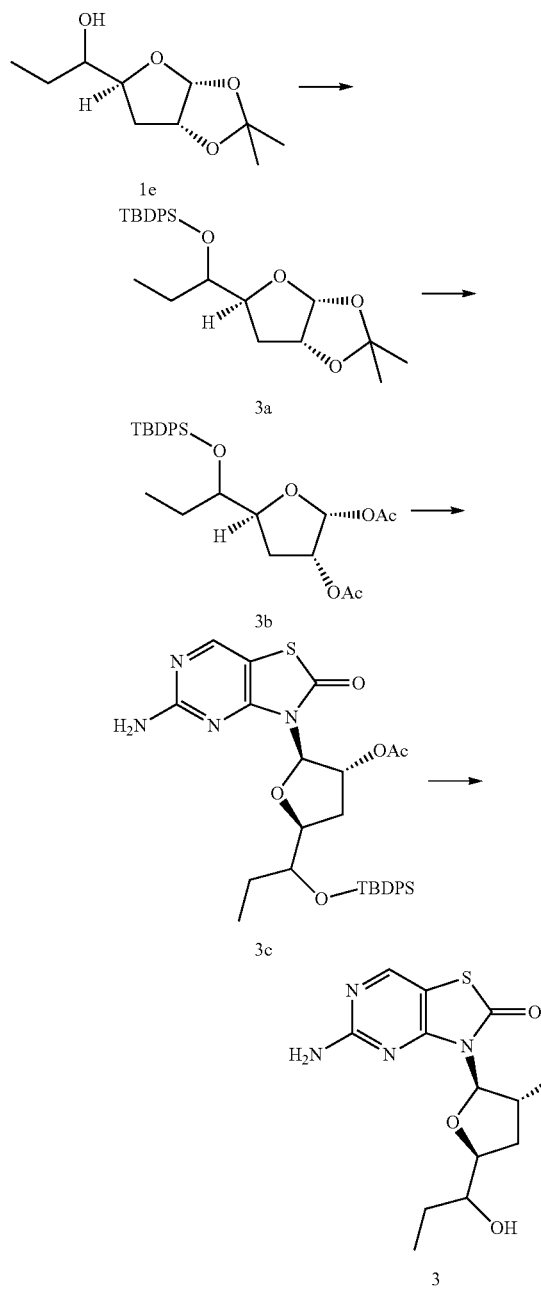

Preparation of 1-[(3aR,5S,6aR)-2,2-dimethyl-3a,5,6,6a-tetrahydrofuro[2,3-d][1,3]dioxol-5-yl]propoxy-tert-butyl-diphenyl-silane

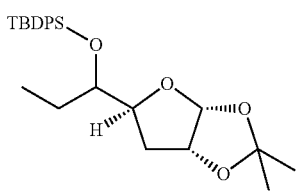

To a solution of 1-[(3aR,5S,6aR)-2,2-dimethyl-3a,5,6,6a-tetrahydrofuro[2,3-d][1,3]dioxol-5-yl]propan-1-ol (compound 1e, 2.02 g, 10 mmol) in DMF (30 mL) was added imidazole (6.5 g, 100 mmol) and tert-butylchlorodiphenyl-silane (8.22 g, 30 mmol) with stirring. After being stirred at room temperature for 2 hours, the resulting solution was diluted by EtOAc (200 mL), washed with water, brine and dried over $Na_2SO_4$. The organic layer was concentrated in vacuo. The residue was purified by column chromatography on silica gel (eluting with 1:10 EtOAc in petroleum ether) to afford 3.6 g of 1-[(3aR,5S,6aR)-2,2-dimethyl-3a,5,6,6a-tetrahydrofuro[2,3-d][1,3]dioxol-5-yl]propoxy-tert-butyl-diphenyl-silane (compound 3a).

Compound 3a: $^1$H NMR (400 MHz, $CDCl_3$) δ ppm: 7.65-7.79 (m, 4H), 7.33-7.49 (m, 6H), 5.52-5.81 (m, 1H), 4.64-4.72 (m, 1H), 4.19-4.32 (m, 1H), 3.67-4.01 (m, 1H), 1.98-2.05 (m, 1H), 1.74-1.94 (m, 1H), 1.61 (s, 6H), 1.34-1.44 (m, 2H), 1.07 (d, J=1.25 Hz, 9H), 0.72-0.83 (m, 3H). MS obsd. (ESI$^+$) [(M+$NH_4$)$^+$]: 458.

Preparation of [(2R,3R,5S)-2-acetoxy-5-[1-[tert-butyl(diphenyl)silyl]oxypropyl]tetrahydrofuran-3-yl]acetate

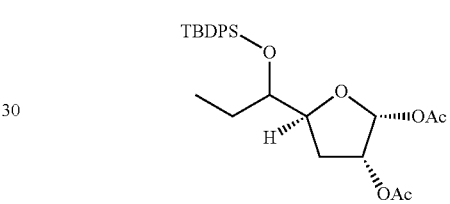

To a solution of 1-[(3aR,5S,6aR)-2,2-dimethyl-3a,5,6,6a-tetrahydrofuro[2,3-d][1,3]dioxol-5-yl]propoxy-tert-butyl-diphenyl-silane (compound 3a, 3.6 g, 8.2 mmol) in the DCM (30 mL) was added acetic acid (15 mL), acetic acid anhydride (15 mL) and $H_2SO_4$ (0.8 mmol). After being stirred at room temperature for 24 hours, TEA (5 mL) was added to the reaction mixture. The resulted solution was diluted with DCM (30 mL). The separated organic layer was washed with saturated $NaHCO_3$ solution, brine and dried over $MgSO_4$. The organic layer was concentrated in vacuo. The residue was purified by column chromatography on silica gel (eluting with 1:30 EtOAc in petroleum ether) to afford 3.7 g of [(2R,3R,5S)-2-acetoxy-5-[1-[tert-butyl(diphenyl)silyl]oxypropyl]tetrahydrofuran-3-yl]acetate (compound 3b). MS obsd. (ESI$^+$) [(M+$NH_4$)$^+$]: 502.

Preparation of [(2R,3R,5S)-2-(5-amino-2-oxo-thiazolo[4,5-d]pyrimidin-3-yl)-5-[1-[tert-butyl(diphenyl)silyl]oxypropyl]tetrahydrofuran-3-yl]acetate

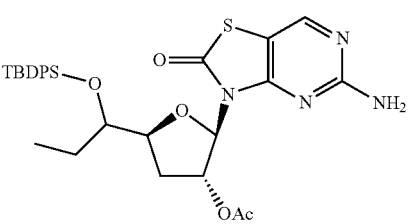

To a suspension of 5-amino-3H-thiazolo[4,5-d]pyrimidin-2-one (1.08 g, 6 mmol) in ACN (100 mL) was added BSA (3.6 g, 18 mmol). The reaction mixture was stirred at 70° C. for 1 hour under argon to form a clear solution. After the solution was cooled to room temperature, [(2R,3R,5S)-2-acetoxy-5-[1-[tert-butyl(diphenyl)silyl]oxypropyl]tetrahydrofuran-3-yl]acetate (compound 3b, 1.45 g, 3 mmol) and TMSOTf (2.0 g, 9 mmol) were added in sequence. After being heated with stirring at 70° C. for 14 hours, the solvent was removed in vacuo. The residue was partitioned between EtOAc (50 mL) and saturated NaHCO$_3$ solution (30 mL). The organic layer was separated and the aqueous phase was extracted with EtOAc (50 mL) twice. The combined organic layers were washed with brine, dried over Na$_2$SO$_4$ and concentrated in vacuo. The residue was purified by column chromatography on silica gel (eluting with 1:1 EtOAc in petroleum ether) to afford 1.04 g of [(2R,3R,5S)-2-(5-amino-2-oxo-thiazolo[4,5-c]pyrimidin-3-yl)-5-[1-[tert-butyl(diphenyl)silyl]oxypropyl]tetrahydrofuran-3-yl]acetate (compound 3c). MS obsd. (ESI$^+$) [(M+H)$^+$]: 593.

Preparation of [(2R,3R,5S)-2-(5-amino-2-oxo-thiazolo[4,5-d]pyrimidin-3-yl)-5-(1-hydroxypropyl)tetrahydrofuran-3-yl]acetate

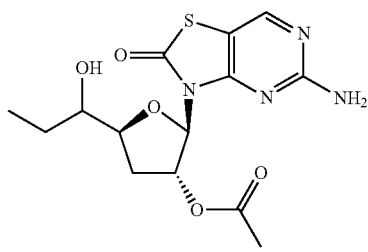

3

To a solution of [(2R,3R,5S)-2-(5-amino-2-oxo-thiazolo[4,5-d]pyrimidin-3-yl)-5-[1-[tert-butyl(diphenyl)silyl]oxypropyl]tetrahydrofuran-3-yl] (compound 3c, 1.04 g, 1.8 mmol) in THF (20 mL) was added TBAF solution (1M in THF, 6 mL, 6 mmol) with stirring. After being stirred at room temperature for 4 hours, the reaction mixture was washed with saturated NH$_4$Cl solution, dried over Na$_2$SO$_4$ and concentrated in vacuo. The residue was purified by column chromatography on silica gel (eluting with 1:2 EtOAc in petroleum ether) to afford 620 mg of [(2R,3R,5S)-2-(5-amino-2-oxo-thiazolo[4,5-d]pyrimidin-3-yl)-5-(1-hydroxypropyl)tetrahydrofuran-3-yl]acetate (Example 3), which was further purified and separated by preparative HPLC to afford 112.8 mg of Example 3-A and 99.8 mg of Example 3-B as white solid.

Example 3-A: $^1$H NMR (400 MHz, CD$_3$OD) δ ppm: 8.22 (s, 1H), 6.04-6.07 (m, 1H), 5.74-5.80 (m, 1H), 4.12-4.19 (m, 1H), 3.50-3.57 (m, 1H), 2.76 (ddd, J=7.40, 10.23, 13.49 Hz, 1H), 2.10 (s, 3H), 2.04-2.10 (m, 1H), 1.54-1.63 (m, 1H), 1.42-1.52 (m, 1H), 1.02 (t, J=7.40 Hz, 3H). MS obsd. (ESI$^+$) [(M+H)$^+$]: 355.

Example 3-B: $^1$H NMR (400 MHz, CD$_3$OD) δ ppm: 8.22 (s, 1H), 5.99-6.07 (m, 1H), 5.70-5.81 (m, 1H), 4.06-4.18 (m, 1H), 3.61-3.71 (m, 1H), 2.77-2.90 (m, 1H), 2.11-2.16 (m, 1H), 2.09 (s, 3H), 1.57-1.68 (m, 1H), 1.34-1.46 (m, 1H), 1.01 (t, J=7.40 Hz, 3H). MS obsd. (ESI$^+$) [(M+H)$^+$]: 355.

Example 4

1-[(2S,4R,5R)-5-(5-amino-2-oxo-thiazolo[4,5-d]pyrimidin-3-yl)-4-hydroxy-tetrahydrofuran-2-yl]propyl acetate

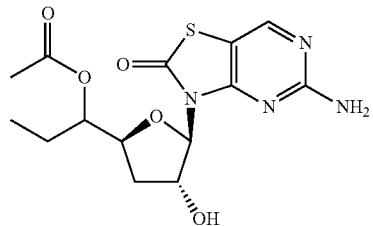

4

To a solution of [(2R,3R,5S)-5-(1-acetoxypropyl)-2-(5-amino-2-oxo-thiazolo[4,5-d]pyrimidin-3-yl)tetrahydrofuran-3-yl]acetate (compound 2a, 150 mg, 0.4 mmol) in methanol (25 mL) was added K$_2$CO$_3$ (14 mg, 0.1 mmol). After being stirred at room temperature for 0.5 hour, the reaction was adjusted to pH 7.0 by addition of HOAc (12.6 mg, 0.2 mmol) and concentrated in vacuo. The residue was purified and separated by preparative HPLC to afford 17.5 mg of Example 4-A and 8.5 mg of Example 4-B as white solid.

Example 4-A: $^1$H NMR (400 MHz, CD$_3$OD) δ ppm: 8.20 (s, 1H), 5.98-6.08 (m, 1H), 4.93-5.01 (m, 2H), 4.31-4.42 (m, 1H), 2.56-2.70 (m, 1H), 2.03 (s, 3H), 1.87-1.95 (m, 1H), 1.54-1.78 (m, 2H), 0.93 (t, J=7.53 Hz, 3H). MS obsd. (ESI$^+$) [(M+H)$^+$]: 355.

Example 4-B: $^1$H NMR (400 MHz, d$_6$-DMSO) δ ppm: 8.28-8.39 (m, 1H), 6.81-6.92 (br. s., 2H), 5.76-5.86 (m, 1H), 5.46-5.58 (br. s, 1H), 4.92-5.02 (m, 1H), 4.79-4.89 (m, 1H), 4.14-4.23 (m, 1H), 2.42-2.48 (m, 1H), 1.98 (s, 3H), 1.78-1.88 (m, 1H), 1.55-1.70 (m, 1H), 1.34-1.49 (m, 1H), 0.82 (t, J=7.40 Hz, 3H). MS obsd. (ESI$^+$) [(M+H)$^+$]: 355.

Example 5

[(2R,3R,5S)-2-(5-amino-2,7-dioxo-6H-thiazolo[4,5-d]pyrimidin-3-yl)-5-(1-hydroxypropyl)tetrahydrofuran-3-yl]acetate

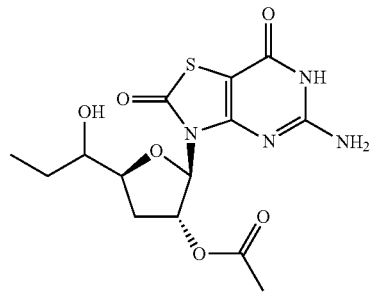

5

To a solution of 5-amino-3-[(2R,3R,5S)-3-hydroxy-5-(1-hydroxypropyl)tetrahydrofuran-2-yl]-6H-thiazolo[4,5-d]pyrimidine-2,7-dione (Example 1, 328 mg, 1 mmol) in DCM (15 mL) was added TEA (404 mg, 4 mmol) and acetic anhydride (48 mg, 1 mmol) with stirring. After being stirred at room temperature for 2 hours, the resulting solution was quenched by acetic acid (240 mg, 4 mmol), washed with brine, dried over MgSO$_4$ and concentrated in vacuo. The residue was purified and separated by preparative HPLC to afford 31.5 mg of Example 5-A and 20.0 mg of Example 5-B as white solid.

Example 5-A: $^1$H NMR (400 MHz, CD$_3$OD) δ ppm: 5.96 (d, J=2.51 Hz, 1H), 5.63-5.77 (m, 1H), 4.05-4.17 (m, 1H), 3.47-3.55 (m, 1H), 2.62-2.79 (m, 1H), 2.09 (s, 3H), 2.00-2.06 (m, 1H), 1.51-1.63 (m, 1H), 1.41-1.51 (m, 1H), 1.02 (t, J=7.53 Hz, 3H). MS obsd. (ESI$^-$) [(M−H)$^+$]: 369.

Example 5-B: $^1$H NMR (400 MHz, CD$_3$OD) δ ppm: 5.95 (d, J=2.51 Hz, 1H), 5.68-5.77 (m, 1H), 4.04-4.14 (m, 1H), 3.60-3.69 (m, 1H), 2.73-2.84 (m, 1H), 2.09 (s, 4H), 1.57-1.67 (m, 1H), 1.35-1.45 (m, 1H), 1.01 (t, J=7.40 Hz, 3H). MS obsd. (ESI$^-$) [(M−H)$^+$]: 369.

Example 6

[(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl]acetate

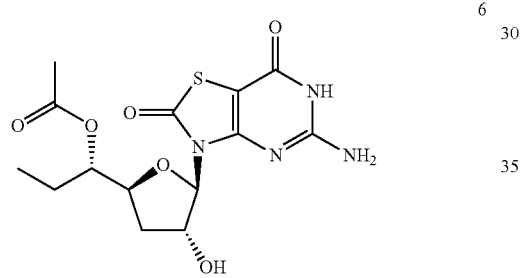

6

The title compound was prepared according to the following scheme:

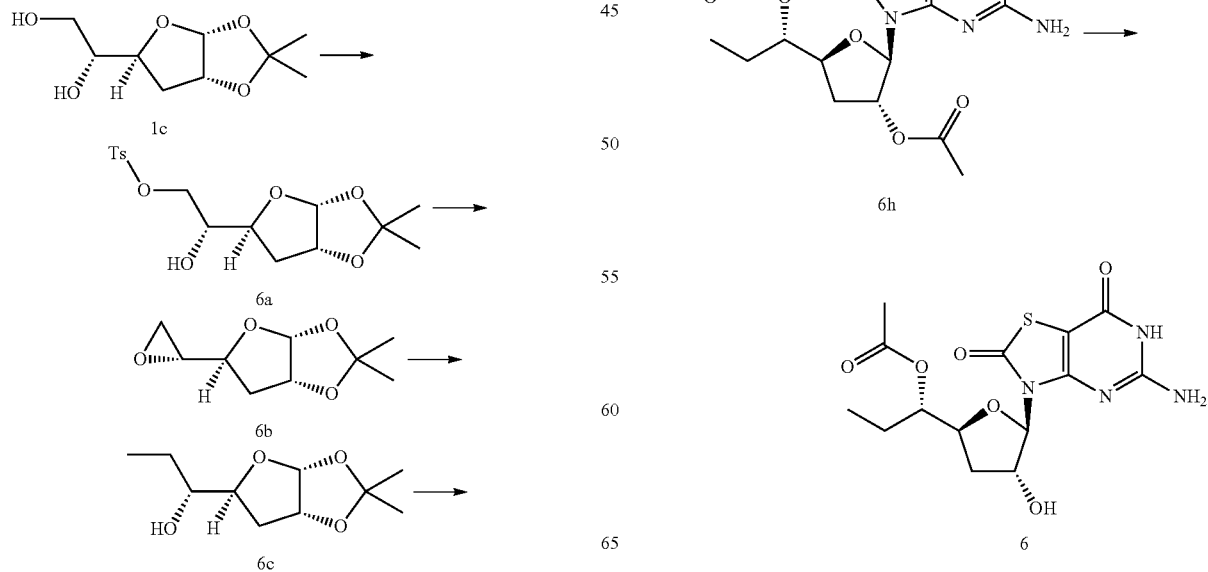

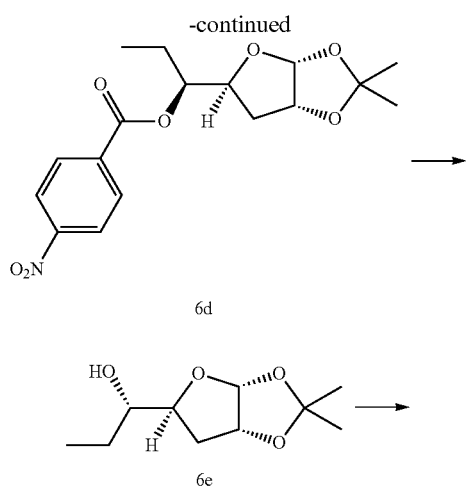

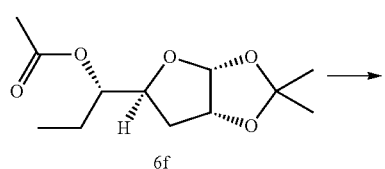

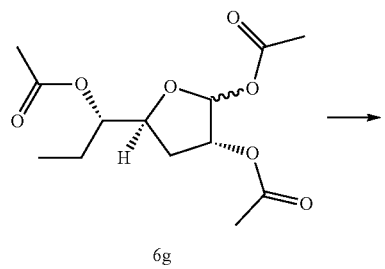

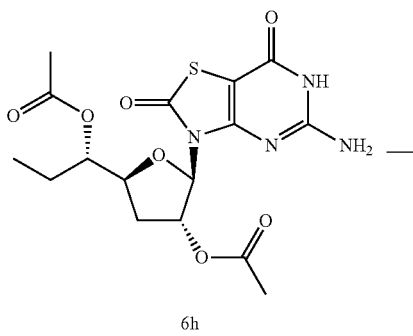

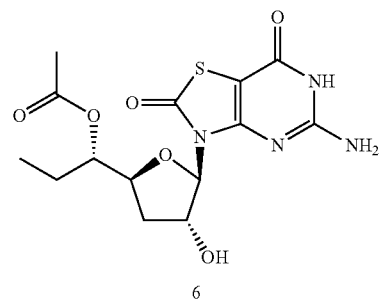 [SMILES: CC[C@H](OC(C)=O)[C@@H]1C[C@@H](O)[C@H](n2c(=O)sc3c(=O)[nH]c(N)nc32)O1]

Preparation of [(2R)-2-[(3aR,5S,6aR)-2,2-dimethyl-3a,5,6,6a-tetrahydrofuro[2,3-d][1,3]dioxol-5-yl]-2-hydroxy-ethyl] 4-methylbenzenesulfonate

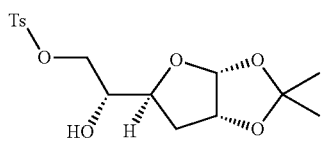

6a

To a solution of (1R)-1-[(3aR,5S,6aR)-2,2-dimethyl-3a,5,6,6a-tetrahydrofuro[2,3-d][1,3]dioxol-5-yl]ethane-1,2-diol (100 g, 490 mmol) in dry pyridine (1000 mL) was added p-toluenesulfonyl chloride (139 g, 735 mmol) at 0° C. After being stirred at room temperature for 12 hours, the resulted solution was quenched by water (100 mL) and concentrated in vacuo. The residue was purified by column chromatography on silica gel (eluting with 1:10 to 1:3 EtOAc in petroleum ether) to afford 130 g of [(2R)-2-[(3aR,5S,6aR)-2,2-dimethyl-3a,5,6,6a-tetrahydrofuro[2,3-d][1,3]dioxol-5-yl]-2-hydroxy-ethyl] 4-methylbenzenesulfonate (compound 6a) as a slight yellow oil.

Compound 6a: $^1$H NMR (400 MHz, CDCl$_3$) δ ppm: 7.82 (d, J=8.00 Hz, 2H), 7.38 (d, J=8.00 Hz, 2H), 5.78 (d, J=3.76 Hz, 1H), 4.75 (t, J=4.00 Hz, 1H), 4.20-4.12 (m, 2H), 4.03-3.97 (m, 2H), 2.48 (s, 3H), 2.39 (d, J=3.51 Hz, 1H), 2.08-2.15 (m, 1H), 1.75-1.80 (m, 1H), 1.51 (s, 3H), 1.33 (s, 3H).

Preparation of (3aR,5S,6aR)-2,2-dimethyl-5-[(2R)-oxiran-2-yl]-3a,5,6,6a-tetrahydrofuro[2,3-d][1,3]dioxole

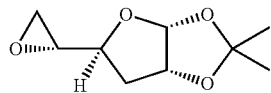

6b

To a solution of [(2R)-2-[(3aR,5S,6aR)-2,2-dimethyl-3a,5,6,6a-tetrahydrofuro[2,3-d][1,3]dioxol-5-yl]-2-hydroxy-ethyl] 4-methylbenzenesulfonate (compound 6a, 100 g, 280 mmol) in anhydrous THF (1500 mL) cooled at –70° C. was added potassium bis(trimethylsilyl)amide (340 mL, 340 mmol, 1 M in THF) under N$_2$ atmosphere. After being stirred at –70° C. for 1 hour, the reaction mixture was poured into saturated NH$_4$Cl solution. The organic layer was separated and the aqueous phase was extracted with EtOAc. The combined organic layers were dried over Na$_2$SO$_4$ and concentrated in vacuo. The residue was purified by column chromatography on silica gel (eluting with 1:3 EtOAc in petroleum ether) to afford 40.5 g of (3aR,5S,6aR)-2,2-dimethyl-5-[(2R)-oxiran-2-yl]-3a,5,6,6a-tetrahydrofuro[2,3-d][1,3]dioxole (compound 6b) as a slight yellow oil.

Compound 6b: $^1$H NMR: (400 MHz, CDCl$_3$) δ ppm: 5.87 (d, J=3.76 Hz, 1H), 4.77 (t, J=4.00 Hz, 1H), 4.20-4.28 (m, 1H), 3.14-3.20 (m, 1H), 2.83-2.88 (m, 1H), 2.63 (dd, J=5.00, 2.80 Hz, 1H), 2.09 (dd, J=12.00, 4.00 Hz, 1H), 1.69-1.79 (m, 1H), 1.52 (s, 3H), 1.34 (s, 3H).

Preparation of (1R)-1-[(3aR,5S,6aR)-2,2-dimethyl-3a,5,6,6a-tetrahydrofuro[2,3-d][1,3]dioxol-5-yl]propan-1-ol

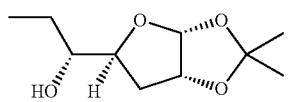

6c

To a suspension of CuI (19.3 g, 107 mmol) in dry THF (2000 mL) under N$_2$ atmosphere was added methyl magnesium bromide (3 M in diethyl ether, 537 mL, 1.61 mol) at –70° C. After being stirred at this temperature for 1 hour, a solution of (3aR,5S,6aR)-2,2-dimethyl-5-[(2R)-oxiran-2-yl]-3a,5,6,6a-tetrahydrofuro[2,3-d][1,3]dioxole (compound 6b, 100 g, 537 mmol, dissolved in anhydrous THF 200 mL) was added to reaction mixture dropwise. After being stirred at –70° C. for additional 2 hours, the reaction mixture was poured into saturated NH$_4$Cl solution. The organic layer was separated and the aqueous phase was extracted with EtOAc twice. The combined organic layers were dried over Na$_2$SO$_4$ and concentrated in vacuo. The residue was purified by column chromatography on silica gel (eluting with 1:3 EtOAc in petroleum ether) to afford 82 g of (1R)-1-[(3aR,5S,6aR)-2,2-dimethyl-3a,5,6,6a-tetrahydrofuro[2,3-d][1,3]dioxol-5-yl]propan-1-ol (compound 6c) as a slight yellow solid.

Compound 6c: $^1$H NMR (400 MHz, CDCl$_3$) δ ppm: 5.83 (d, J=3.76 Hz, 1H), 4.81-4.73 (m, 1H), 4.26-4.19 (m, 1H), 3.91-3.82 (m, 1H), 2.08-2.02 (m, 1H), 1.93-1.89 (m, 1H), 1.54 (s, 3H), 1.49-1.39 (m, 2H), 1.34 (s, 3H), 1.02 (t, J=7.53 Hz, 3H).

Preparation of [(1S)-1-[(3aR,5S,6aR)-2,2-dimethyl-3a,5,6,6a-tetrahydrofuro[2,3-d][1,3]dioxol-5-yl]propyl] 4-nitrobenzoate

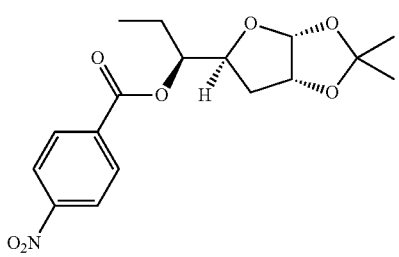

6d

To a stirred solution of (1R)-1-[(3aR,5S,6aR)-2,2-dimethyl-3a,5,6,6a-tetrahydrofuro[2,3-d][1,3]dioxol-5-yl]propan-1-ol (compound 6c, 50 g, 245 mmol), triphenylphosphine (195 g, 743 mmol), 4-nitrobenzoic acid (124 g, 743 mmol) in THF (1200 mL) was added diethyl azodicarboxylate (130 g, 743 mmol) dropwise at 0° C. under N$_2$. After being stirred at 18° C. for 10 hours, the mixture was quenched by addition of saturated NaHCO$_3$ solution and extracted with EtOAc. The organic layers were combined, dried over Na$_2$SO$_4$ and concentrated in vacuo. The residue was purified by column chromatography on silica gel (eluting with 1:3 EtOAc in petroleum ether) to afford 61 g of [(1S)-1-[(3aR,5S,6aR)-2,2-dimethyl-3a,5,6,6a-tetrahydrofuro[2,3-d][1,3]dioxol-5-yl]propyl] 4-nitrobenzoate (compound 6d) as a slight yellow solid.

Compound 6d: ¹H NMR (400 MHz, CDCl₃) δ ppm: 8.34-8.22 (m, 4H), 5.85 (d, J=3.76 Hz, 1H), 5.23-5.17 (m, 1H), 4.76 (t, J=4.27 Hz, 1H), 4.48-4.39 (m, 1H), 2.12 (dd, J=13.30, 4.52 Hz, 1H), 1.88-1.78 (m, 2H), 1.71-1.62 (m, 1H), 1.55 (s, 3H), 1.34 (s, 3H), 1.01 (t, J=7.40 Hz, 3H).

Preparation of (1S)-1-[(3aR,5S,6aR)-2,2-dimethyl-3a,5,6,6a-tetrahydrofuro[2,3-d][1,3]dioxol-5-yl]propan-1-ol

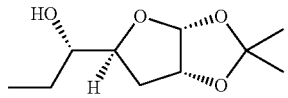

6e

To a solution of [(1S)-1-[(3aR,5S,6aR)-2,2-dimethyl-3a,5,6,6a-tetrahydrofuro[2,3-d][1,3]dioxol-5-yl]propyl] 4-nitrobenzoate (compound 6d, 100 g, 285 mmol) in methanol (1200 mL) was added K₂CO₃ (78.7 g, 570 mmol). After being stirred at room temperature for 10 minutes, the resulted mixture was filtered. The filtrate was concentrated in vacuo. The residue was purified by column chromatography on silica gel (eluting with 1:8 EtOAc in petroleum ether) to afford 54.7 g of (1S)-1-[(3aR,5S,6aR)-2,2-dimethyl-3a,5,6,6a-tetrahydrofuro[2,3-d][1,3]dioxol-5-yl]propan-1-ol (compound 6e) as a slight yellow solid.

Compound 6e: ¹H NMR (400 MHz, CDCl₃) δ ppm: 5.81 (d, J=3.64 Hz, 1H), 4.75 (t, J=4.20 Hz, 1H), 4.18-4.11 (m, 1H), 3.49-3.40 (m, 1H), 2.07-2.00 (m, 2H), 1.84-1.75 (m, 1H), 1.59-1.47 (m, 5H), 1.32 (s, 3H), 1.01 (t, J=7.40 Hz, 3H).

Preparation of [(1S)-1-[(3aR,5S,6aR)-2,2-dimethyl-3a,5,6,6a-tetrahydrofuro[2,3-d][1,3]dioxol-5-yl]propyl]acetate

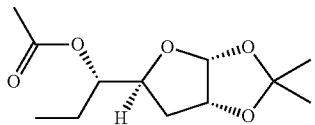

6f

To a stirred solution of (1S)-1-[(3aR,5S,6aR)-2,2-dimethyl-3a,5,6,6a-tetrahydrofuro[2,3-d][1,3]dioxol-5-yl]propan-1-ol (compound 6e, 13.5 g, 67 mmol), TEA (81 g, 804 mmol), DMAP (1.6 g, 13 mmol) in anhydrous DCM (150 mL) was added acetic anhydride (62 g, 603 mmol). After being stirred at 22° C. for 10 hours, the reaction was quenched by the saturated NaHCO₃ solution. The organic layer was separated and the aqueous phase was extracted with EtOAc. The combined organic layers were dried over Na₂SO₄, and concentrated in vacuo. The residue was purified by column chromatography on silica gel (eluting with 1:8 EtOAc in petroleum ether) to afford 13 g of [(1S)-1-[(3aR,5S,6aR)-2,2-dimethyl-3a,5,6,6a-tetrahydrofuro[2,3-d][1,3]dioxol-5-yl]propyl]acetate (compound 6f) as a colourless oil.

Compound 6f: ¹H NMR (400 MHz, CDCl₃) δ ppm: 5.83 (d, J=3.76 Hz, 1H), 4.92 (dt, J=7.97, 5.18 Hz, 1H), 4.74 (t, J=4.00 Hz, 1H), 4.35-4.27 (m, 1H), 2.12 (s, 3H), 2.08-1.99 (m, 1H), 1.74-1.56 (m, 3H), 1.53 (s, 3H), 1.34 (s, 3H), 0.95 (t, J=7.40 Hz, 3H).

Preparation of [(3R,5S)-2-acetoxy-5-[(1S)-1-acetoxypropyl]tetrahydrofuran-3-yl]acetate

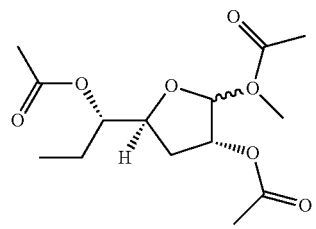

6g

To a solution of [(1S)-1-[(3aR,5S,6aR)-2,2-dimethyl-3a,5,6,6a-tetrahydrofuro[2,3-d][1,3]dioxol-5-yl]propyl]acetate (compound 6f, 4.8 g, 20 mmol), acetic acid (12.2 g, 200 mmol) and acetic anhydride (10.2 g, 100 mmol) in anhydrous DCM (100 mL) was added concentrated H₂SO₄ (0.5 mL) at 0° C. After being stirred at 22° C. for 3 hours, the reaction was quenched by addition of saturated NaHCO₃ solution. The organic layer was separated and the aqueous phase was extracted with EtOAc. The combined organic layers were dried over Na₂SO₄, filtered, and concentrated in vacuo. The residue was purified by column on silica gel (eluting with 1:8 EtOAc in petroleum ether) to afford 2.3 g of [(3R,5S)-2-acetoxy-5-[(1S)-1-acetoxypropyl]tetrahydrofuran-3-yl] acetate (compound 6g) as a colourless oil.

Compound 6g: ¹H NMR (400 MHz, CDCl₃) δ ppm: 6.12 (s, 1H), 5.19 (d, J=4.52 Hz, 1H), 4.83-4.91 (m, 1H), 4.34-4.44 (m, 1H), 2.09-2.19 (m, 9H), 1.51-1.74 (m, 4H), 0.94 (t, J=7.40 Hz, 3H).

Preparation of [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl]acetate

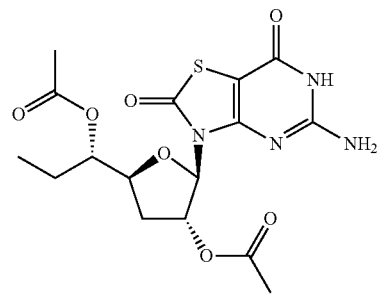

6h

To a suspension of 5-amino-3,6-dihydrothiazolo[4,5-d]pyrimidine-2,7-dione (1.4 g, 7.5 mmol) in ACN (20 mL) was added BSA (7.7 g, 38 mmol). The reaction mixture was stirred at 70° C. for 0.5 hour under argon to form a clear solution. After the solution was cooled to room temperature, [(3R,5S)-2-acetoxy-5-[(1S)-1-acetoxypropyl]tetrahydrofuran-3-yl]acetate (compound 6g, 720 mg, 2.5 mmol) and TMSOTf (8.3 g, 38 mmol) were added in sequence. After being heated with stirring at 70° C. for 14 hours, the solvent was removed in vacuo. The residue was partitioned between EtOAc and saturated NaHCO$_3$ solution (30 mL). The organic layer was separated and the aqueous phase was extracted with EtOAc (30 mL) twice. The combined organic layers were washed with brine, dried over Na$_2$SO$_4$ and concentrated in vacuo. The residue was purified by column chromatography on silica gel to afford 470 mg of [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl]acetate (compound 6h) as slight yellow solid. MS obsd. (ESI⁻) [(M−H)⁺]: 411.

Preparation of [(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl]acetate

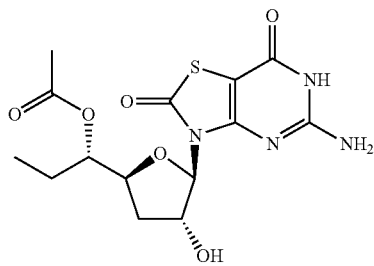

6

To a solution of [(2R,3R,5S)-5-[(1S)-1-acetoxypropyl]-2-(5-amino-2,7-dioxo-6H-thiazolo[4,5-d]pyrimidin-3-yl)tetrahydrofuran-3-yl]acetate (compound 6h, 210 mg, 0.5 mmol) in methanol (25 mL) was added K$_2$CO$_3$ (136 mg, 1 mmol). After being stirred at room temperature for 10 min, the reaction was adjusted to pH 7.0 by addition of HOAc (120 mg, 2 mmol), concentrated in vacuo and the residue was purified by preparative HPLC to afford 66.7 mg of [(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl]acetate (Example 6) as a white solid.

Example 6: ¹H NMR (400 MHz, CD$_3$OD) δ ppm: 5.94 (d, J=1.51 Hz, 1H), 5.00-4.93 (m, 2H), 4.37-4.30 (m, 1H), 2.63-2.54 (m, 1H), 2.05 (s, 3H), 1.91-1.83 (m, 1H), 1.74-1.58 (m, 2H), 0.93 (t, J=7.40 Hz, 3H). MS obsd. (ESI⁻) [(M−H)⁺]: 369.

Example 7

5-Amino-3-[(2R,3R,5S)-3-hydroxy-5-(1-hydroxy-ethyl)tetrahydrofuran-2-yl]-6H-thiazolo[4,5-d]pyrimidine-2,7-dione

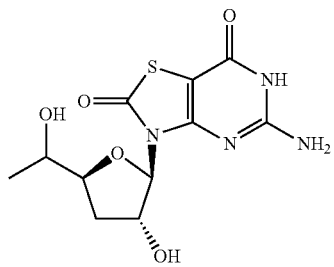

7

The title compound was prepared in analogy to Example 1, by using methyl magnesium bromide instead of ethyl magnesium bromide. Example 7 was purified and separated by preparative HPLC to afford Example 7-A and Example 7-B as white solid.

Example 7-A: ¹H NMR (400 MHz, CD$_3$OD) δ ppm: 5.91-5.97 (m, 1H), 4.91-4.96 (m, 1H), 4.07-4.13 (m, 1H), 3.86-3.95 (m, 1H), 2.58-2.68 (m, 1H), 1.92-2.01 (m, 1H), 1.17 (d, J=6.53 Hz, 3H). MS obsd. (ESI⁻) [(M−H)⁺]: 313.

Example 7-B: ¹H NMR (400 MHz, CD$_3$OD) δ ppm: 5.97 (d, J=2.76 Hz, 1H), 4.90-4.94 (m, 1H), 4.06-4.14 (m, 1H), 3.73-3.82 (m, 1H), 2.46-2.58 (m, 1H), 1.86-1.96 (m, 1H), 1.17 (d, J=6.27 Hz, 3H). MS obsd. (ESI⁻) [(M−H)⁺]: 313.

Example 8

5-Amino-3-[(2R,3R,5S)-3-hydroxy-5-(1-hydroxy-but-3-enyl)tetrahydrofuran-2-yl]-6H-thiazolo[4,5-d]pyrimidine-2,7-dione

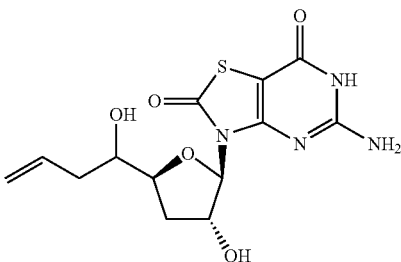

8

The title compound was prepared in analogy to Example 1, by using allyl magnesium bromide instead of ethyl magnesium bromide. Example 8 was purified and separated by preparative HPLC to afford Example 8-A and Example 8-B as white solid.

Example 8-A: ¹H NMR (400 MHz, CD$_3$OD) δ ppm: 5.94-5.99 (m, 1H), 5.86-5.92 (m, 1H), 5.05-5.15 (m, 3H), 4.18-4.26 (m, 1H), 3.64 (m, 1H), 2.51-2.60 (m, 1H), 2.19-2.34 (m, 2H), 1.95 (m, 1H). MS obsd. (ESI⁻) [(M−H)⁺]: 339.

Example 8-B: ¹H NMR (400 MHz, CD$_3$OD) δ ppm: 5.83-5.99 (m, 2H), 4.96-5.21 (m, 3H), 4.17 (d, J=5.02 Hz, 1H), 3.80 (d, J=3.76 Hz, 1H), 2.58-2.73 (m, 1H), 2.27-2.38 (m, 1H), 2.19 (td, J=7.06, 14.24 Hz, 1H), 1.89-2.01 (m, 1H). MS obsd. (ESI⁻) [(M−H)⁺]: 339.

Example 9

5-Amino-3-[(2R,3R,5S)-3-hydroxy-5-(1-hydroxy-pentyl)tetrahydrofuran-2-yl]-6H-thiazolo[4,5-d]pyrimidine-2,7-dione

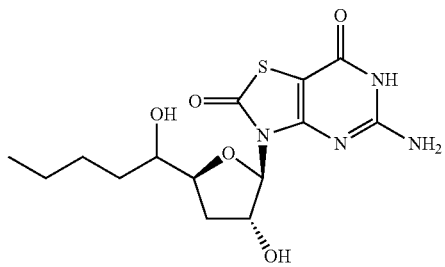

9

The title compound was prepared in analogy to Example 1, by using butyl magnesium bromide instead of ethyl magnesium bromide. Example 9 was purified and separated by preparative HPLC to afford Example 9-A and Example 9-B as white solid.

Example 9-A: $^1$H NMR (400 MHz, CD$_3$OD) δ ppm: 5.95 (d, J=3.26 Hz, 1H), 4.95-5.01 (m, 1H), 4.16-4.22 (m, 1H), 3.51-3.60 (m, 1H), 2.49-2.58 (m, 1H), 1.90-2.00 (m, 1H), 1.44-1.55 (m, 3H), 1.20-1.40 (m, 3H), 0.87-0.98 (m, 3H). MS obsd. (ESI$^-$) [(M−H)$^+$]: 355.

Example 9-B: $^1$H NMR (400 MHz, CD$_3$OD) δ ppm: 5.90-5.95 (m, 1H), 4.93-4.99 (m, 1H), 4.12-4.20 (m, 1H), 3.69-3.77 (m, 1H), 2.59-2.67 (m, 1H), 1.90-1.98 (m, 1H), 1.49-1.60 (m, 2H), 1.29-1.44 (m, 4H), 0.91-0.97 (m, 3H). MS obsd. (ESI$^-$) [(M−H)$^+$]: 355.

Example 10

5-Amino-3-[(2R,3R,5S)-3-hydroxy-5-(1-hydroxybutyl)tetrahydrofuran-2-yl]-6H-thiazolo[4,5-d]pyrimidine-2,7-dione

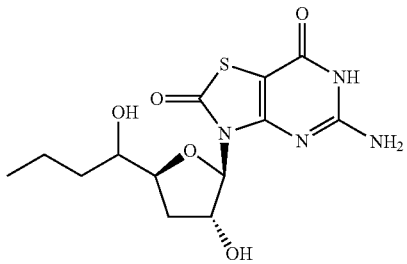

The title compound was prepared in analogy to Example 1, by using propyl magnesium bromide instead of ethyl magnesium bromide. Example 10 was purified and separated by preparative HPLC to afford Example 10-A and Example 10-B as white solid.

Example 10-A: $^1$H NMR (400 MHz, CD$_3$OD) δ ppm: 5.93-5.99 (m, 1H), 4.92-4.95 (m, 1H), 4.13-4.22 (m, 1H), 3.53-3.63 (m, 1H), 2.48-2.60 (m, 1H), 1.87-1.99 (m, 1H), 1.50-1.61 (m, 1H), 1.36-1.50 (m, 3H), 0.91-1.01 (m, 3H). MS obsd. (ESI$^-$) [(M−H)$^+$]: 341.

Example 10-B: $^1$H NMR (400 MHz, CD$_3$OD) δ ppm: 5.90-5.96 (m, 1H), 4.92-4.96 (m, 1H), 4.11-4.19 (m, 1H), 3.71-3.80 (m, 1H), 2.56-2.69 (m, 1H), 1.89-1.99 (m, 1H), 1.46-1.60 (m, 2H), 1.34-1.45 (m, 2H), 0.96 (t, J=6.90 Hz, 3H). MS obsd. (ESI$^-$) [(M−H)$^+$]: 341.

Example 11

5-Amino-3-[(2R,3R,5S)-5-[cyclopentyl(hydroxy)methyl]-3-hydroxy-tetrahydrofuran-2-yl]-6H-thiazolo[4,5-d]pyrimidine-2,7-dione

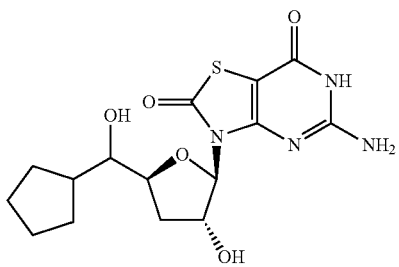

Preparation of [(3aR,5S,6aR)-2,2-dimethyl-3a,5,6,6a-tetrahydrofuro[2,3-d][1,3]dioxol-5-yl]-cyclopentyl-methanol

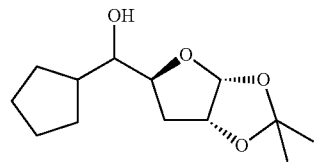

To a solution of (3aR,5S,6aR)-2,2-dimethyl-3a,5,6,6a-tetrahydrofuro[2,3-d][1,3]dioxole-5-carbaldehyde (4.0 g, 23.2 mmol) in THF (20 mL) was added cyclopentylmagnesium bromide (1M in THF, 30 mL, 30 mmol) at −20° C. under argon. After being stirred at −20° C. for 20 hours, the reaction was quenched by saturated NH$_4$Cl solution. The reaction mixture was extracted with EtOAc (30 mL) three times. The organic layers were combined and concentrated in vacuo to afford 1.2 g crude product of [(3aR,5S,6aR)-2,2-dimethyl-3a,5,6,6a-tetrahydrofuro[2,3-d][1,3]dioxol-5-yl]-cyclopentyl-methanol (compound 11a) as a colorless oil, which was used in next step without further purification. MS obsd. (ESI$^+$) [(M+H)$^+$]: 243.

Preparation of [[(3aR,5S,6aR)-2,2-dimethyl-3a,5,6,6a-tetrahydrofuro[2,3-d][1,3]dioxol-5-yl]-cyclopentyl-methyl] benzoate

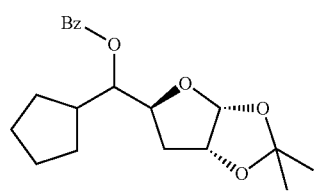

To a solution of [(3aR,5S,6aR)-2,2-dimethyl-3a,5,6,6a-tetrahydrofuro[2,3-d][1,3]dioxol-5-yl]-cyclopentyl-methanol (compound 11a, 1.2 g, 5.0 mmol), TEA (3.2 g, 31.2 mmol) and DMAP (100 mg) in DCM (50 mL) was added benzoyl chloride (1.4 g, 10.0 mmol) slowly at 0° C. The mixture was stirred at 25° C. for 4 hours and then quenched by saturated NaHCO$_3$ solution. The reaction mixture was extracted with EtOAc (100 mL) twice. The organic layers were combined, washed with brine (50 mL), dried over Na$_2$SO$_4$ and concentrated in vacuo. The residue was purified by column chromatography on silica gel (eluting with 1:20 to 1:5 EtOAc in petroleum ether) to afford 1.4 g of [[(3aR,5S,6aR)-2,2-dimethyl-3a,5,6,6a-tetrahydrofuro[2,3-d][1,3]dioxol-5-yl]-cyclopentyl-methyl] benzoate (compound 11b) as a colourless oil.

Preparation of [cyclopentyl-[(2S,4R)-4,5-diacetoxytetrahydrofuran-2-yl]methyl] benzoate

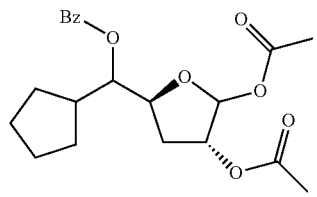

11c

To a solution of [[(3aR,5S,6aR)-2,2-dimethyl-3a,5,6,6a-tetrahydrofuro[2,3-d][1,3]dioxol-5-yl]-cyclopentyl-methyl] benzoate (compound 11b, 800 mg, 2.3 mmol) in the mixture of acetic acid (2 mL) and acetic acid anhydride (2 mL) was added H$_2$SO$_4$ (0.2 mmol). After being stirred at room temperature for 24 hours, the solution was diluted by EtOAc (40 mL) and adjusted to pH 5.0 by addition of saturated NaHCO$_3$ solution. The organic layer was separated, washed with brine, dried over Na$_2$SO$_4$ and concentrated in vacuo. The residue was purified by column chromatography on silica gel (eluting with 1:3 EtOAc in petroleum ether) to afford 480 mg of [cyclopentyl-[(2S,4R)-4,5-diacetoxytetrahydrofuran-2-yl]methyl] benzoate (compound 11c).

Preparation of [[(2S,4R,5R)-4-acetoxy-5-(5-amino-2,7-dioxo-6H-thiazolo[4,5-d]pyrimidin-3-yl)tetrahydrofuran-2-yl]-cyclopentyl-methyl] benzoate

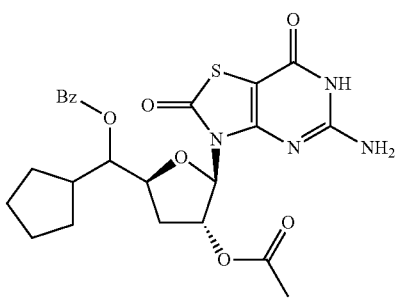

11d

To a suspension of 5-amino-3,6-dihydrothiazolo[4,5-d]pyrimidine-2,7-dione (370 mg, 2.0 mmol) in ACN (20 mL) was added BSA (2.1 g, 10 mmol). The resulting reaction mixture was then stirred at 70° C. for 0.5 hour under argon to form a clear solution. After the solution was cooled to room temperature, [cyclopentyl-[(2S,4R)-4,5-diacetoxytetrahydrofuran-2-yl]methyl] benzoate (compound 11c, 400 mg, 1.0 mmol) and TMSOTf (2.25 g, 10 mmol) were added in sequence. After being heated with stirring at 70° C. for 14 hours, the solvent was evaporated in vacuo. The residue was partitioned between EtOAc and saturated NaHCO$_3$ solution (30 mL). The organic layer was collected and the aqueous phase was extracted with EtOAc (30 mL) twice. The combined organic layers were washed with brine, dried over Na$_2$SO$_4$ and concentrated in vacuo. The residue was purified by column chromatography on silica gel (eluting with 1:1 EtOAc in petroleum ether) to afford 160 mg of [[(2S,4R,5R)-4-acetoxy-5-(5-amino-2,7-dioxo-6H-thiazolo[4,5-d]pyrimidin-3-yl)tetrahydrofuran-2-yl]-cyclopentyl-methyl] benzoate (compound 11d).

Compound 11d: $^1$H NMR (400 MHz, CDCl$_3$) δ ppm: 7.96-7.99 (m, 2H), 7.59-7.61 (m, 1H), 7.44-7.50 (m, 2H), 5.82-5.93 (m, 1H), 5.23-5.26 (m, 1H), 4.45-4.52 (m, 1H), 3.73-3.76 (m, 1H), 2.81-2.85 (m, 1H), 2.41-2.43 (m, 1H), 2.09 (s, 3H), 1.31-1.89 (m, 8H).

Preparation of 5-amino-3-[(2R,3R,5S)-5-[cyclopentyl(hydroxy)methyl]-3-hydroxy-tetrahydrofuran-2-yl]-6H-thiazolo[4,5-d]pyrimidine-2,7-dione

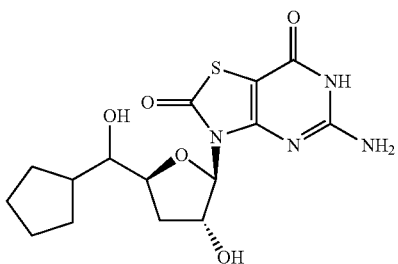

11

To a solution of [[(2S,4R,5R)-4-acetoxy-5-(5-amino-2,7-dioxo-6H-thiazolo[4,5-d]pyrimidin-3-yl)tetrahydrofuran-2-yl]-cyclopentyl-methyl] benzoate (compound 11d, 70 mg, 0.14 mmol) in methanol (10 mL) was added K$_2$CO$_3$ (136 mg, 1 mmol). After being stirred at room temperature for 12 hours, the reaction mixture was adjusted to pH 7.0 by addition of HOAc (120 mg, 2 mmol), concentrated in vacuo and the residue was purified by preparative HPLC to afford 4.7 mg of 5-amino-3-[(2R,3R,5S)-5-[cyclopentyl(hydroxy)methyl]-3-hydroxy-tetrahydrofuran-2-yl]-6H-thiazolo[4,5-d]pyrimidine-2,7-dione (Example 11) as a white solid.

Example 11: $^1$H NMR (400 MHz, CD$_3$OD) δ ppm: 5.91-5.93 (m, 1H), 4.94-4.98 (m, 2H), 4.31-4.36 (m, 1H), 2.56-2.61 (m, 1H), 2.00-2.06 (m, 2H), 1.31-1.72 (m, 8H). MS obsd. (ESI$^+$) [(M+H)$^+$]: 369.

Example 12

5-Amino-3-[(2R,3R,5S)-3-hydroxy-5-(1-hydroxy-2-phenyl-ethyl)tetrahydrofuran-2-yl]-6H-thiazolo[4,5-d]pyrimidine-2,7-dione

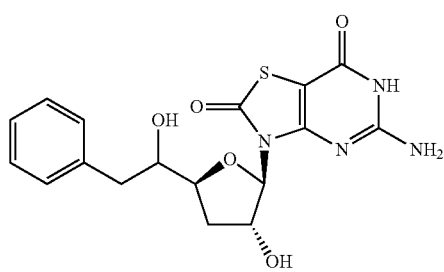

12

The title compound was prepared in analogy to Example 1, by using benzyl magnesium bromide instead of ethyl magnesium bromide. Example 12 was purified and separated by preparative HPLC to afford Example 12-A and Example 12-B as white solid.

Example 12-A: $^1$H NMR (400 MHz, CD$_3$OD) δ ppm: 7.24-7.33 (m, 4H), 7.16-7.24 (m, 1H), 5.93-5.98 (m, 1H), 4.94-4.97 (m, 1H), 4.22 (dt, J=4.02, 7.53 Hz, 1H), 3.76-3.84 (m, 1H), 2.74-2.90 (m, 2H), 2.60 (td, J=7.53, 13.05 Hz, 1H), 1.97 (m, 1H). MS obsd. (ESI⁻) [(M–H)⁺]: 389.

Example 12-B: ¹H NMR (400 MHz, CD₃OD) δ ppm: 7.51-7.57 (m, 1H), 7.09-7.25 (m, 4H), 5.91-5.96 (m, 1H), 5.10-5.15 (m, 1H), 4.93-5.00 (m, 2H), 4.39-4.48 (m, 1H), 2.74-2.87 (m, 1H), 2.28-2.35 (m, 2H), 1.82-1.92 (m, 1H). MS obsd. (ESI⁻) [(M–H)⁺]: 389.

Example 13

5-Amino-3-[(2R,3R,5S)-3-hydroxy-5-(1-hydroxy-3-methyl-butyl)tetrahydrofuran-2-yl]-6H-thiazolo[4,5-d]pyrimidine-2,7-dione

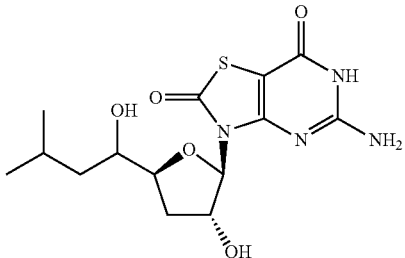

The title compound was prepared in analogy to Example 1, by using iso-butyl magnesium bromide instead of ethyl magnesium bromide. Example 13 was purified and separated by preparative HPLC to afford Example 13-A and Example 13-B as white solid.

Example 13-A: ¹H NMR (400 MHz, CD₃OD) δ ppm: 5.93-5.99 (m, 1H), 4.91-4.95 (m, 1H), 4.10-4.19 (m, 1H), 3.62-3.69 (m, 1H), 2.48-2.59 (m, 1H), 1.81-1.98 (m, 2H), 1.41-1.52 (m, 1H), 1.15-1.25 (m, 1H), 0.95 (t, J=6.78 Hz, 6H). MS obsd. (ESI⁻) [(M–H)⁺]: 355.

Example 13-B: ¹H NMR (400 MHz, CD₃OD) δ ppm: 5.89-5.96 (m, 1H), 4.92-4.98 (m, 1H), 4.08-4.17 (m, 1H), 3.81-3.89 (m, 1H), 2.58-2.69 (m, 1H), 1.89-1.99 (m, 1H), 1.78-1.89 (m, 1H), 1.23-1.40 (m, 2H), 0.94 (dd, J=6.65, 14.18 Hz, 6H). MS obsd. (ESI⁻) [(M–H)⁺]: 355.

Example 14

5-Amino-3-[(2R,3R,5S)-5-[cyclopropyl(hydroxy)methyl]-3-hydroxy-tetrahydrofuran-2-yl]-6H-thiazolo[4,5-d]pyrimidine-2,7-dione

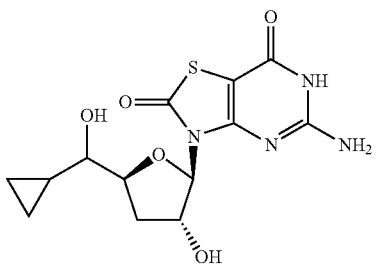

Preparation of [(3R,5S)-2-acetoxy-5-[acetoxy(cyclopropyl)methyl]tetrahydrofuran-3-yl] acetate

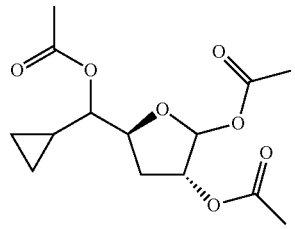

Compound 14a was prepared in analogy to [(3R,5S)-2-acetoxy-5-(1-acetoxypropyl)tetrahydrofuran-3-yl]acetate (compound 1f), by using cyclopropyl magnesium bromide instead of ethyl magnesium bromide.

Preparation of [(2R,3R,5S)-5-[acetoxy(cyclopropyl)methyl]-2-(5-amino-2,7-dioxo-6H-thiazolo[4,5-d]pyrimidin-3-yl)tetrahydrofuran-3-yl]acetate

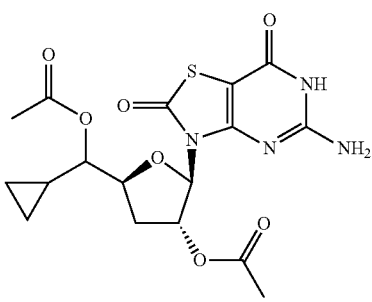

Compound 14b was prepared in analogy to [(2R,3R,5S)-5-(1-acetoxypropyl)-2-(5-amino-2,7-dioxo-6H-thiazolo[4,5-d]pyrimidin-3-yl)tetrahydrofuran-3-yl]acetate (compound 1g), by using [(3R,5S)-2-acetoxy-5-[acetoxy(cyclopropyl)methyl]tetrahydrofuran-3-yl]acetate (compound 14a) instead of [(3R,5S)-2-acetoxy-5-(1-acetoxypropyl)tetrahydrofuran-3-yl]acetate (compound 1f). MS obsd. (ESI⁻) [(M–H)⁻]: 441.

Preparation of 5-amino-3-[(2R,3R,5S)-5-[cyclopropyl(hydroxy)methyl]-3-hydroxy-tetrahydrofuran-2-yl]-6H-thiazolo[4,5-d]pyrimidine-2,7-dione

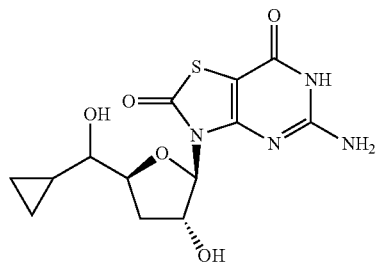

The title compound was prepared in analogy to Example 1, by using [(2R,3R,5S)-5-[acetoxy(cyclopropyl)methyl]-2-(5-amino-2,7-dioxo-6H-thiazolo[4,5-d]pyrimidin-3-yl)tetrahydrofuran-3-yl]acetate (compound 14b) instead of [(2R,3R,5S)-5-(1-acetoxypropyl)-2-(5-amino-2,7-dioxo-6H-thiazolo[4,5-d]pyrimidin-3-yl)tetrahydrofuran-3-yl]acetate (compound 1g). Example 14 was purified and separated by preparative HPLC to afford Example 14-A and Example 14-B as white solid.

Example 14-A: $^1$H NMR (400 MHz, CD$_3$OD) δ ppm: 5.94-6.00 (m, 1H), 4.93-4.96 (m, 1H), 4.27-4.35 (m, 1H), 2.91-2.98 (m, 1H), 2.54-2.66 (m, 1H), 1.98-2.06 (m, 1H), 0.88-0.99 (m, 1H), 0.46-0.56 (m, 2H), 0.26-0.39 (m, 2H). MS obsd. (ESI$^-$) [(M−H)$^-$]: 339.

Example 14-B: $^1$H NMR (400 MHz, CD$_3$OD) δ ppm: 5.93-5.96 (m, 1H), 4.92-5.00 (m, 1H), 4.30-4.38 (m, 1H), 3.09-3.16 (m, 1H), 2.68-2.79 (m, 1H), 1.94-2.05 (m, 1H), 0.81-0.92 (m, 1H), 0.49-0.58 (m, 2H), 0.35-0.43 (m, 1H), 0.25-0.33 (m, 1H). MS obsd. (ESI$^-$) [(M−H)$^-$]: 339.

Example 15

[[(2S,4R,5R)-5-(5-amino-2,7-dioxo-6H-thiazolo[4,5-d]pyrimidin-3-yl)-4-hydroxy-tetrahydrofuran-2-yl]-cyclopropyl-methyl]acetate

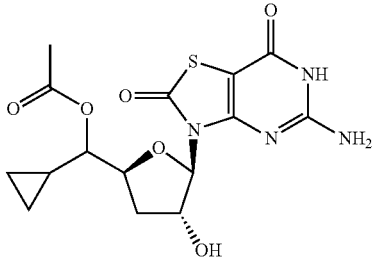

15

To a solution of [(2R,3R,5S)-5-[acetoxy(cyclopropyl)methyl]-2-(5-amino-2,7-dioxo-6H-thiazolo[4,5-d]pyrimidin-3-yl)tetrahydrofuran-3-yl]acetate (compound 14b, crude, 220 mg, 0.5 mmol) in methanol (25 mL) was added K$_2$CO$_3$ (136 mg, 1 mmol). After being stirred at room temperature for 1 hour, the reaction was adjusted to pH 7.0 by addition of HOAc (120 mg, 2 mmol), concentrated in vacuo and the residue was purified and separated by preparative HPLC to afford 7.5 mg of Example 15-A and 7.5 mg of Example 15-B as white solid.

Example 15-A: $^1$H NMR (400 MHz, CD$_3$OD) δ ppm: 5.94-5.98 (m, 1H), 4.83-4.87 (m, 1H), 4.39-4.47 (m, 2H), 2.62-2.70 (m, 1H), 1.92-2.07 (m, 4H), 1.03-1.12 (m, 1H), 0.60-0.66 (m, 1H), 0.38-0.55 (m, 3H). MS obsd. (ESI$^-$) [(M−H)$^+$]: 381.

Example 15-B: $^1$H NMR (400 MHz, CD$_3$OD) δ ppm: 5.89-5.96 (m, 1H), 4.94-4.99 (m, 1H), 4.60-4.67 (m, 1H), 4.37-4.45 (m, 1H), 2.75-2.88 (m, 1H), 2.04 (s, 3H), 1.90-2.00 (m, 1H), 0.98-1.08 (m, 1H), 0.58-0.66 (m, 1H), 0.46-0.53 (m, 1H), 0.36 (m, 2H). MS obsd. (ESI$^-$) [(M−H)$^+$]: 381.

Example 16

[(S)-[(2S,4R,5R)-5-(5-amino-2-oxo-thiazolo[4,5-d]pyrimidin-3-yl)-4-hydroxy-tetrahydrofuran-2-yl]-cyclopropyl-methyl]acetate

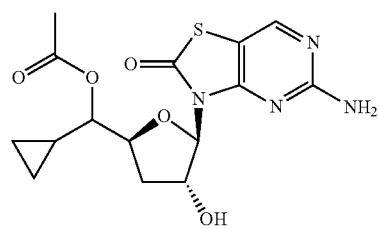

16

Preparation of [(2R,3R,5S)-5-[acetoxy(cyclopropyl)methyl]-2-(5-amino-2-oxo-thiazolo[4,5-d]pyrimidin-3-yl)tetrahydrofuran-3-yl]acetate (16a)

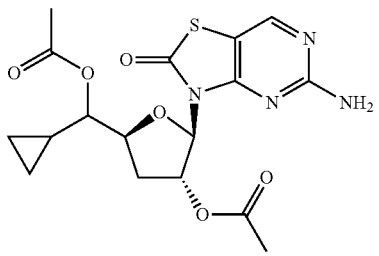

16a

Compound 16a was prepared in analogy to [(2R,3R,5S)-5-(1-acetoxypropyl)-2-(5-amino-2-oxo-thiazolo[4,5-d]pyrimidin-3-yl)tetrahydrofuran-3-yl]acetate (compound 2a), by using [(3R,5S)-2-acetoxy-5-[acetoxy(cyclopropyl)methyl]tetrahydrofuran-3-yl]acetate (compound 14a) instead of [(3R,5S)-2-acetoxy-5-(1-acetoxypropyl)tetrahydrofuran-3-yl]acetate (compound 1f).

Preparation of [(S)-[(2S,4R,5R)-5-(5-amino-2-oxo-thiazolo[4,5-d]pyrimidin-3-yl)-4-hydroxy-tetrahydrofuran-2-yl]-cyclopropyl-methyl]acetate

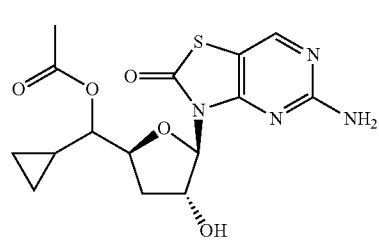

16

The title compound was prepared in analogy to Example 4, by using [(2R,3R,5S)-5-[acetoxy(cyclopropyl)methyl]-2-(5-amino-2-oxo-thiazolo[4,5-d]pyrimidin-3-yl)tetrahydrofuran-3-yl] acetate (compound 16a) instead of [(2R,3R,5S)-5-(1-acetoxypropyl)-2-(5-amino-2-oxo-thiazolo[4,5-d]pyrimidin-3-yl)tetrahydrofuran-3-yl]acetate (compound 2a). Example 16 was purified and separated by preparative HPLC to afford Example 16-A and Example 16-B as white solid.

Example 16-A: $^1$H NMR (400 MHz, CD$_3$OD) δ ppm: 8.21 (s, 1H), 6.06 (d, J=1.51 Hz, 1H), 4.93-4.98 (m, 1H), 4.38-4.52 (m, 2H), 2.64-2.76 (m, 1H), 2.02 (s, 3H), 1.96-2.00 (m, 1H), 1.02-1.12 (m, 1H), 0.59-0.67 (m, 1H), 0.49-0.55 (m, 1H), 0.36-0.48 (m, 2H). MS obsd. (ESI$^-$) [(M+H)$^+$]: 367.

Example 16-B: $^1$H NMR (400 MHz, CD$_3$OD) δ ppm: 8.18-8.25 (m, 1H), 5.98-6.07 (m, 1H), 4.96-5.03 (m, 1H), 4.64-4.72 (m, 1H), 4.40-4.51 (m, 1H), 2.80-2.91 (m, 1H), 2.03 (s, 3H), 1.94-2.00 (m, 1H), 0.96-1.09 (m, 1H), 0.58-0.68 (m, 1H), 0.44-0.55 (m, 1H), 0.27-0.41 (m, 2H). MS obsd. [(M+H)$^+$]: 367.

Example 17

5-Amino-3-[(2R,3R,5S)-5-[cyclopropyl(hydroxy)methyl]-3-hydroxy-tetrahydrofuran-2-yl]thiazolo[4,5-d]pyrimidin-2-one

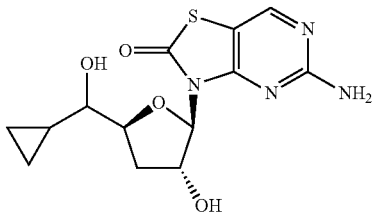

17

The title compound was prepared in analogy to Example 2, by using [(2R,3R,5S)-5-[acetoxy(cyclopropyl)methyl]-2-(5-amino-2-oxo-thiazolo[4,5-d]pyrimidin-3-yl)tetrahydrofuran-3-yl] acetate (compound 16a) instead of [(2R,3R,5S)-5-(1-acetoxypropyl)-2-(5-amino-2-oxo-thiazolo[4,5-d]pyrimidin-3-yl)tetrahydrofuran-3-yl]acetate (compound 2a). Example 17 was purified and separated by preparative HPLC to afford Example 17-A and Example 17-B as white solid.

Example 17-A: $^1$H NMR (400 MHz, CD$_3$OD) δ ppm: 8.22 (s, 1H), 6.07 (d, J=3.01 Hz, 1H), 4.93-4.98 (m, 1H), 4.29-4.40 (m, 1H), 2.93-3.01 (m, 1H), 2.59-2.69 (m, 1H), 2.00-2.09 (m, 1H), 0.89-0.98 (m, 1H), 0.49-0.58 (m, 2H), 0.32-0.41 (m, 2H). MS obsd. (ESI$^-$) [(M+H)$^+$]: 325.

Example 17-B: $^1$H NMR (400 MHz, CD$_3$OD) δ ppm: 8.23 (s, 1H), 5.99-6.06 (m, 1H), 4.96-5.02 (m, 1H), 4.33-4.40 (m, 1H), 3.10-3.17 (m, 1H), 2.74-2.81 (m, 1H), 2.00-2.07 (m, 1H), 0.83-0.92 (m, 1H), 0.49-0.58 (m, 2H), 0.36-0.42 (m, 1H), 0.26-0.33 (m, 1H). MS obsd. [(M+H)$^+$]: 325.

Example 18

5-Amino-3-[(2R,3R,5S)-3-hydroxy-5-(1-hydroxyprop-2-ynyl)tetrahydrofuran-2-yl]-6H-thiazolo[4,5-d]pyrimidine-2,7-dione

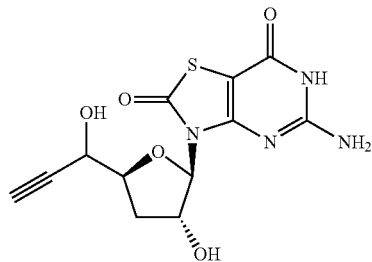

18

The title compound was prepared in analogy to Example 1, by using ethynyl magnesium bromide instead of ethyl magnesium bromide. Example 18 was purified and separated by preparative HPLC to afford Example 18-A and Example 18-B as white solid.

Example 18-A: $^1$H NMR (400 MHz, CD$_3$OD) δ ppm: 6.00 (d, J=2.51 Hz, 1H), 4.90-4.98 (m, 1H), 4.35-4.42 (m, 1H), 4.22-4.33 (m, 1H), 2.56-2.63 (m, 1H), 1.97-2.11 (m, 1H). MS obsd. (ESI$^-$) [(M−H)$^+$]: 323.

Example 18-B: $^1$H NMR (400 MHz, d$_6$-DMSO) δ ppm: 11.26-11.41 (br. s, 1H), 6.90-7.07 (br. s, 2H), 5.71-5.77 (m, 1H), 5.56-5.64 (m, 1H), 5.44-5.50 (m, 1H), 4.78-4.86 (m, 1H), 4.16-4.23 (m, 1H), 4.02-4.13 (m, 1H), 2.41-2.47 (m, 1H), 1.80-1.92 (m, 1H). MS obsd. (ESI$^-$) [(M−H)$^+$]: 323.

Example 19

5-Amino-3-[(2R,3R,5S)-3-hydroxy-5-(1-hydroxybut-2-ynyl)tetrahydrofuran-2-yl]-6H-thiazolo[4,5-d]pyrimidine-2,7-dione

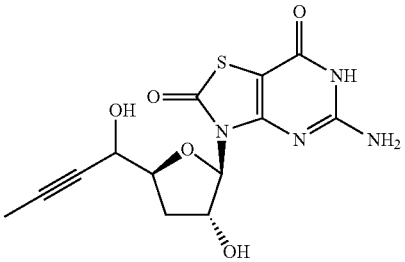

19

The title compound was prepared in analogy to Example 1, by using propynylmagnesium bromide instead of ethyl magnesium bromide. Example 19 was purified and separated by preparative HPLC to afford Example 19-A and Example 19-B as white solid.

Example 19-A: $^1$H NMR (400 MHz, CD$_3$OD) δ ppm: 5.97-6.03 (m, 1H), 4.92-4.97 (m, 1H), 4.32-4.37 (m, 1H), 4.22-4.29 (m, 1H), 2.57-2.66 (m, 1H), 1.99-2.07 (m, 1H), 1.84 (d, J=2.26 Hz, 3H). MS obsd. (ESI$^-$) [(M−H)$^+$]: 337.

Example 19-B: $^1$H NMR (400 MHz, CD$_3$OD) δ ppm: 5.93-5.98 (m, 1H), 4.95-5.01 (m, 1H), 4.41-4.46 (m, 1H), 4.24-4.32 (m, 1H), 2.67-2.77 (m, 1H), 1.98-2.07 (m, 1H), 1.83 (d, J=2.01 Hz, 3H). MS obsd. (ESI⁻) [(M–H)⁺]: 337.

Example 20

5-Amino-3-[(2R,3R,5S)-3-hydroxy-5-[hydroxy(2-thienyl)methyl]tetrahydrofuran-2-yl]-6H-thiazolo[4,5-d]pyrimidine-2,7-dione

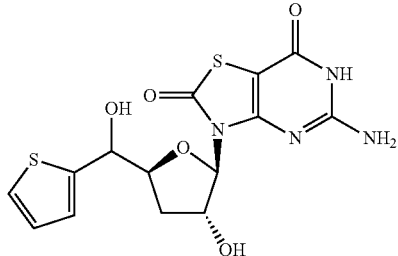

The title compound was prepared in analogy to Example 1, by using 2-thienyl lithium instead of ethyl magnesium bromide. Example 20 was purified and separated by preparative HPLC to afford Example 20-A and Example 20-B as white solid.

Example 20-A: ¹H NMR (400 MHz, CD₃OD) δ ppm: 7.33-7.39 (m, 1H), 7.07-7.11 (m, 1H), 6.98-7.02 (m, 1H), 6.02-6.06 (m, 1H), 4.90-4.97 (m, 2H), 4.46-4.52 (m, 1H), 2.52-2.57 (m, 1H), 1.71-1.76 (m, 1H). MS obsd. (ESI⁻) [(M–H)⁻]: 381.

Example 20-B: ¹H NMR (400 MHz, CD₃OD) δ ppm: 7.30-7.34 (m, 1H), 7.02-7.05 (m, 1H), 6.98 (d, J=5.02 Hz, 1H), 5.96 (d, J=3.76 Hz, 1H), 5.09-5.14 (m, 1H), 4.98-5.04 (m, 1H), 4.43-4.49 (m, 1H), 2.69-2.77 (m, 1H), 1.94-2.02 (m, 1H). MS obsd. (ESI⁻) [(M–H)⁻]: 381.

Example 21

5-Amino-3-[(2R,3R,5S)-3-hydroxy-5-(1-hydroxy-2-methoxy-ethyl)tetrahydrofuran-2-yl]-6H-thiazolo[4,5-d]pyrimidine-2,7-dione

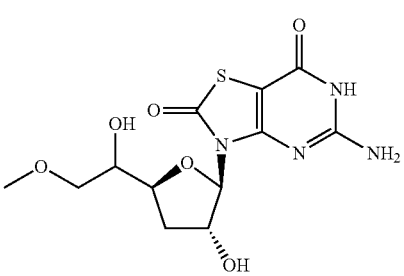

The title compound was prepared according to the following scheme:

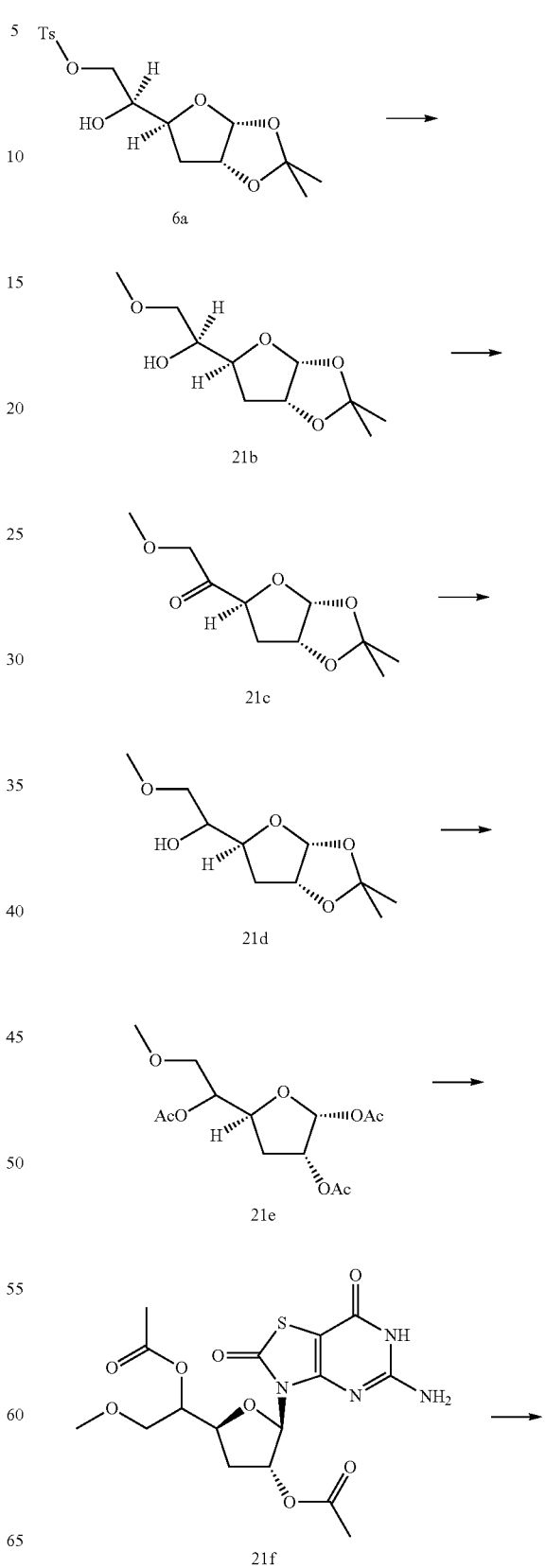

-continued

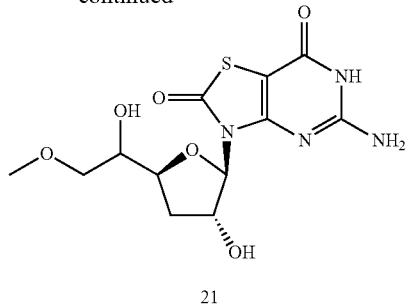

21

Preparation of (1S)-1-[(3aR,5S,6aR)-2,2-dimethyl-3a,5,6,6a-tetrahydrofuro[2,3-d][1,3]dioxol-5-yl]-2-methoxy-ethanol

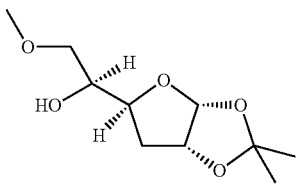

21b

To a stirred solution of [(2S)-2-[(3aR,5S,6aR)-2,2-dimethyl-3a,5,6,6a-tetrahydrofuro[2,3-d][1,3]dioxol-5-yl]-2-hydroxy-ethyl] 4-methylbenzenesulfonate (compound 6a, 3.2 g, 8.9 mmol) in methanol (50 mL) was added $K_2CO_3$ (5.4 g, 40 mmol). After being stirred at room temperature for 2 hours, the resulting solution was concentrated in vacuo and the residue was purified by column chromatography on silica gel (eluting with 1:10 EtOAc in petroleum ether) to afford 1.62 g of (1S)-1-[(3aR,5S,6aR)-2,2-dimethyl-3a,5,6,6a-tetrahydrofuro[2,3-d][1,3]dioxol-5-yl]-2-methoxy-ethanol (compound 21b) as a colorless oil.

Compound 21b: $^1$H NMR (400 MHz, $CDCl_3$) δ ppm: 5.76-5.83 (m, 1H), 4.67-4.77 (m, 1H), 4.15-4.25 (m, 1H), 3.90-4.00 (m, 1H), 3.46 (d, J=3.76 Hz, 1H), 3.31-3.42 (m, 4H), 2.57-2.68 (m, 1H), 2.01-2.10 (m, 1H), 1.78-1.90 (m, 1H), 1.49 (s, 3H), 1.31 (s, 3H).

Preparation of 1-[(3aR,5S,6aR)-2,2-dimethyl-3a,5,6,6a-tetrahydrofuro[2,3-d][1,3]dioxol-5-yl]-2-methoxy-ethanone

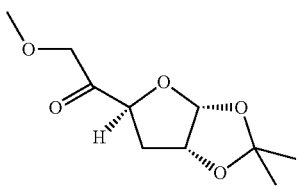

21c

To a solution of (1S)-1-[(3aR,5S,6aR)-2,2-dimethyl-3a,5,6,6a-tetrahydrofuro[2,3-d][1,3]dioxol-5-yl]-2-methoxy-ethanol (compound 21b, 1.62 g, 7.4 mmol) in DCM (50 mL) was added Dess-Martine periodinane (4.7 g, 11 mmol) with stirring. After being stirred at room temperature for 2 hours, the resulting solution was filtered and the filtrate was concentrated in vacuo. The residue was purified by column chromatography on silica gel (eluting with 1:2 EtOAc in petroleum ether) to afford 1.4 g of 1-[(3aR,5S,6aR)-2,2-dimethyl-3a,5,6,6a-tetrahydrofuro[2,3-d][1,3]dioxol-5-yl]-2-methoxy-ethanone (compound 21c) as a colorless oil. MS obsd. (ESI$^+$) [(M+NH$_4$)$^+$]: 234.

Preparation of 1-[(3aR,5S,6aR)-2,2-dimethyl-3a,5,6,6a-tetrahydrofuro[2,3-d][1,3]dioxol-5-yl]-2-methoxy-ethanol

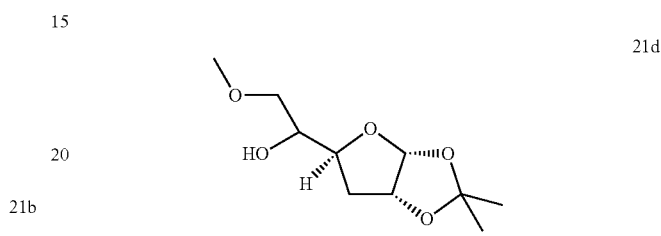

21d

To a stirred solution of 1-[(3aR,5S,6aR)-2,2-dimethyl-3a,5,6,6a-tetrahydrofuro[2,3-d][1,3]dioxol-5-yl]-2-methoxy-ethanone (compound 21c, 1.4 g, 6.5 mmol) in methanol (50 mL) was added sodium borohydride (494 mg, 13 mmol). After being stirred at room temperature for 2 hours, the resulting solution was quenched by saturated $NH_4Cl$ solution and concentrated in vacuo. The residue was suspended in EtOAc and then filtered. The filtrate was concentrated in vacuo to afford 1.24 g of crude product of 1-[(3aR,5S,6aR)-2,2-dimethyl-3a,5,6,6a-tetrahydrofuro[2,3-d][1,3]dioxol-5-yl]-2-methoxy-ethanol (compound 21d) as a colorless oil. MS obsd. (ESI$^+$) [(M+NH$_4$)$^+$]: 236.

Preparation of [(2R,3R,5S)-2-acetoxy-5-(1-acetoxy-2-methoxy-ethyl)tetrahydrofuran-3-yl] acetate

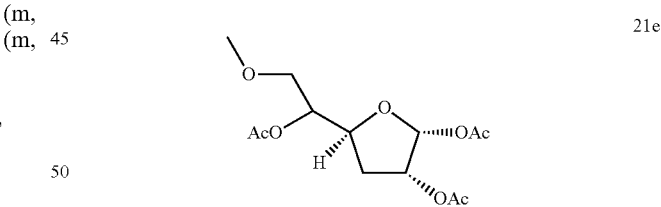

21e

To a solution of 1-[(3aR,5S,6aR)-2,2-dimethyl-3a,5,6,6a-tetrahydrofuro[2,3-d][1,3]dioxol-5-yl]-2-methoxy-ethanol (compound 21d, 1.24 g, 5.7 mmol) in the mixture of acetic acid (4 mL) and acetic acid anhydride (4 mL) was added $H_2SO_4$ (0.3 mmol). After being stirred at room temperature for 24 hours, the solution was diluted by EtOAc (40 mL) and adjusted to pH 8.0 by addition of saturated $NaHCO_3$ solution. The organic layer was separated, washed with brine, dried over $Na_2SO_4$, concentrated in vacuo and the residue was purified by column chromatography on silica gel (eluting with 1:2 EtOAc in petroleum ether) to afford 1.5 g of [(2R,3R,5S)-2-acetoxy-5-(1-acetoxy-2-methoxy-ethyl)tetrahydrofuran-3-yl]acetate (compound 21e) as a colorless oil. MS obsd. (ESI$^+$) [(M+NH$_4$)$^+$]: 322.

Preparation of [(2R,3R,5S)-5-(1-acetoxy-2-methoxy-ethyl)-2-(5-amino-2,7-dioxo-6H-thiazolo[4,5-d]pyrimidin-3-yl)tetrahydrofuran-3-yl]acetate

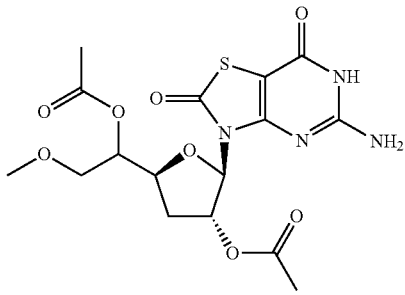

21f

To a suspension of 5-amino-3,6-dihydrothiazolo[4,5-d]pyrimidine-2,7-dione (368 mg, 2.0 mmol) in ACN (20 mL) was added BSA (1.2 mg, 6.0 mmol). The reaction mixture was stirred at 70° C. for 0.5 hour under argon to form a clear solution. After the solution was cooled to room temperature, [(2R,3R,5S)-2-acetoxy-5-(1-acetoxy-2-methoxy-ethyl)tetrahydrofuran-3-yl]acetate (compound 21e, 304 mg, 1.0 mmol) and TMSOTf (666 mg, 3.0 mmol) were added in sequence. After being heated with stirring at 70° C. for 14 hours, the solvent was removed in vacuo. The residue was partitioned between EtOAc and saturated NaHCO₃ solution (30 mL). The organic layer was separated and the aqueous phase was extracted with EtOAc (30 mL) twice. The combined organic layers were washed with brine, dried over Na₂SO₄ and concentrated in vacuo to afford 320 mg crude product of [(2R,3R,5S)-5-(1-acetoxy-2-methoxy-ethyl)-2-(5-amino-2,7-dioxo-6H-thiazolo[4,5-d]pyrimidin-3-yl)tetrahydrofuran-3-yl]acetate (compound 21f), which was used in next step without purification. MS obsd. (ESI⁻) [(M−H)⁺]: 427.

Preparation of 5-amino-3-[(2R,3R,5S)-3-hydroxy-5-(1-hydroxy-2-methoxy-ethyl)tetrahydrofuran-2-yl]-6H-thiazolo[4,5-d]pyrimidine-2,7-dione

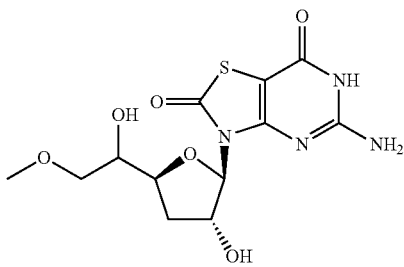

21

To a solution of [(2R,3R,5S)-5-(1-acetoxy-2-methoxy-ethyl)-2-(5-amino-2,7-dioxo-6H-thiazolo[4,5-d]pyrimidin-3-yl)tetrahydrofuran-3-yl]acetate (compound 21f, prepared above) in methanol (25 mL) was added K₂CO₃ (272 mg, 2 mmol). After being stirred at room temperature for 12 hours, the reaction mixture was adjusted to pH 7-8 by addition of HOAc (240 mg, 4 mmol), concentrated in vacuo and the residue was purified and separated by preparative HPLC to afford 22.6 mg of Example 21-A and 22.3 mg of Example 21-B as white solid.

Example 21-A: ¹H NMR (400 MHz, CD₃OD) δ ppm: 5.92-5.98 (m, 1H), 4.92-4.95 (m, 1H), 4.29-4.37 (m, 1H), 3.72-3.79 (m, 1H), 3.42-3.51 (m, 2H), 3.38 (s, 3H), 2.56-2.68 (m, 1H), 1.91-2.01 (m, 1H). MS obsd. (ESI⁻) [(M−H)⁻]: 343.

Example 21-B: ¹H NMR (400 MHz, CD₃OD) δ ppm: 5.91-5.96 (m, 1H), 4.92-4.95 (m, 1H), 4.20-4.28 (m, 1H), 3.85-3.91 (m, 1H), 3.49-3.56 (m, 1H), 3.39-3.45 (m, 1H), 3.37 (s, 3H), 2.63-2.73 (m, 1H), 1.95-2.03 (m, 1H). MS obsd. (ESI⁻) [(M−H)⁻]: 343.

Example 22

5-Amino-3-[(2R,3R,5S)-5-(1-hydroxypropyl)-3-methylsulfanyl-tetrahydrofuran-2-yl]-6H-thiazolo[4,5-d]pyrimidine-2,7-dione

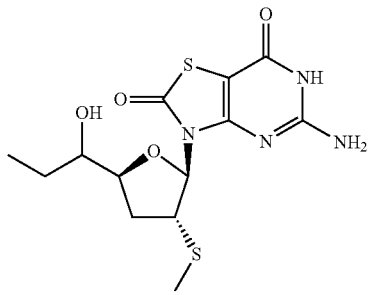

22

The title compound was prepared according to the following scheme:

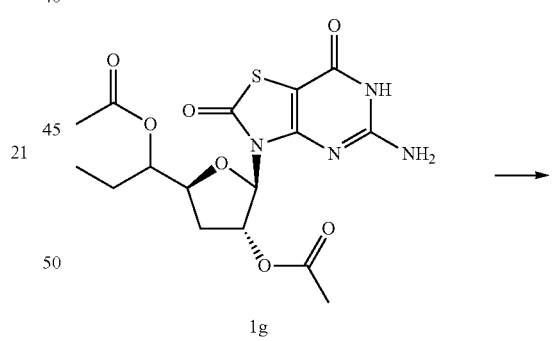

1g

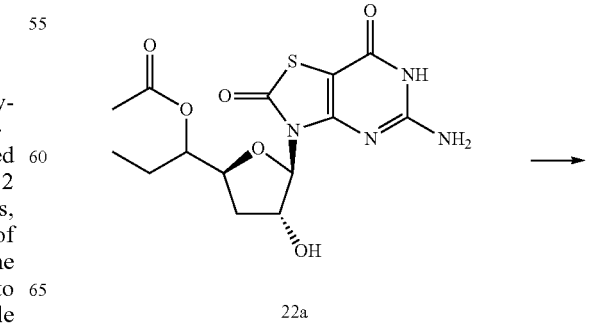

22a

-continued

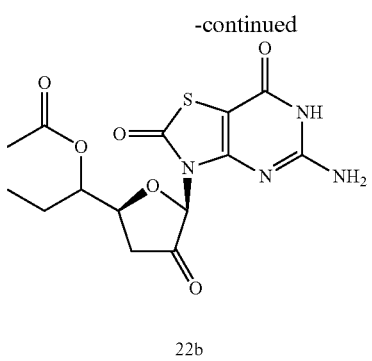

22b

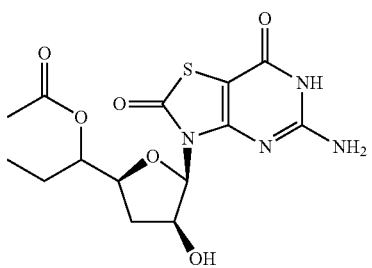

22c

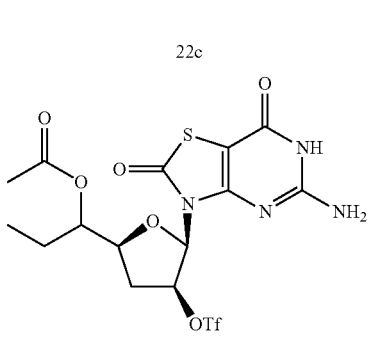

22d

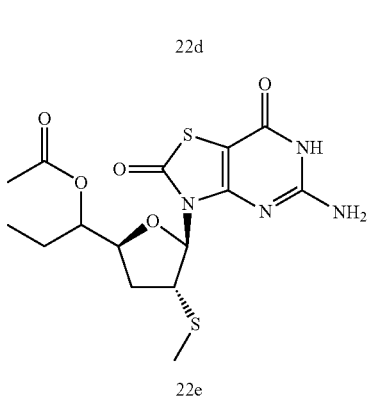

22e

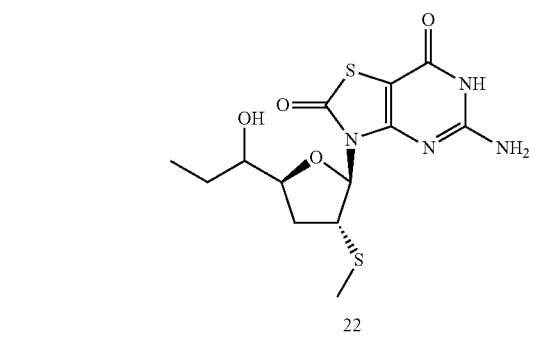

22

Preparation of 1-[(2S,4R,5R)-5-(5-amino-2,7-dioxo-6H-thiazolo[4,5-d]pyrimidin-3-yl)-4-hydroxy-tetrahydrofuran-2-yl]propyl acetate

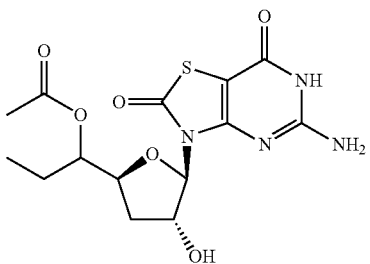

22a

To a solution of [(2R,3R,5S)-5-(1-acetoxypropyl)-2-(5-amino-2,7-dioxo-6H-thiazolo[4,5-d]pyrimidin-3-yl)tetrahydrofuran-3-yl]acetate (compound 1g, 7.0 g, 16.9 mmol) in methanol (200 mL) was added $K_2CO_3$ (1.18 g, 8.5 mmol). After being stirred at room temperature for 12 hours, the reaction mixture was adjusted to pH 6.0 by addition of HOAc (1.2 g, 17 mmol), concentrated in vacuo and the residue was purified by column chromatography on silica gel (eluting with 1:2 EtOAc in petroleum ether) to afford 2.8 g of 1-[(2S,4R,5R)-5-(5-amino-2,7-dioxo-6H-thiazolo[4,5-d]pyrimidin-3-yl)-4-hydroxy-tetrahydrofuran-2-yl]propyl acetate (compound 22a) as a yellow solid. MS obsd. (ESI$^-$) [(M–H)$^+$]: 369.

Preparation of 1-[(2S,5R)-5-(5-amino-2,7-dioxo-6H-thiazolo[4,5-d]pyrimidin-3-yl)-4-oxo-tetrahydrofuran-2-yl]propyl acetate

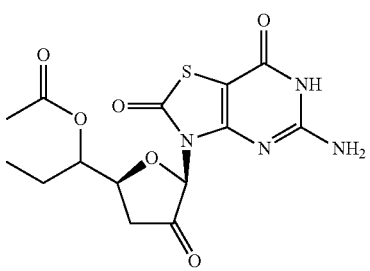

22b

To a stirred solution of 1-[(2S,4R,5R)-5-(5-amino-2,7-dioxo-6H-thiazolo[4,5-d]pyrimidin-3-yl)-4-hydroxy-tetrahydrofuran-2-yl]propyl acetate (compound 22a, 2.8 g, 7.6 mmol) in THF (100 mL) was added Dess-Martine periodinane (4.8 g, 11.3 mmol). After being stirred at room temperature for 2 hours, the resulting solution was filtered and the filtrate was concentrated in vacuo. The residue was purified by column chromatography on silica gel (eluting with 1:10 methanol in DCM) to afford 2.8 g crude product of 1-[(2S,5R)-5-(5-amino-2,7-dioxo-6H-thiazolo[4,5-d]pyrimidin-3-yl)-4-oxo-tetrahydrofuran-2-yl]propyl acetate (compound 22b). MS obsd. (ESI$^-$) [(M–H)$^-$]: 367.

Preparation of 1-[(2S,4S,5R)-5-(5-amino-2,7-dioxo-6H-thiazolo[4,5-d]pyrimidin-3-yl)-4-hydroxy-tetrahydrofuran-2-yl]propyl acetate

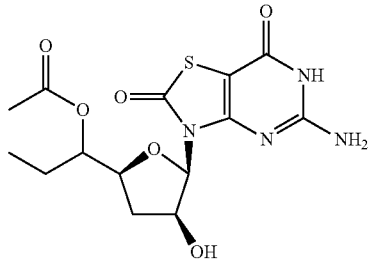

22c

To a stirred solution of 1-[(2S,5R)-5-(5-amino-2,7-dioxo-6H-thiazolo[4,5-d]pyrimidin-3-yl)-4-oxo-tetrahydrofuran-2-yl]propyl acetate (compound 22b, 2.8 g, 7.6 mmol) in THF (50 mL) was added lithium tri-tert-butoxyaluminum hydride (1M in THF, 15 mL, 15 mmol). After being stirred at room temperature for 2 hours, the resulting solution was quenched by saturated NH$_4$Cl solution and filtered. The filtrate was concentrated in vacuo and the residue was purified by column chromatography on silica gel (eluting with 1:10 methanol in DCM) to afford 1.76 g crude product of 1-[(2S,4S,5R)-5-(5-amino-2,7-dioxo-6H-thiazolo[4,5-d]pyrimidin-3-yl)-4-hydroxy-tetrahydrofuran-2-yl]propyl acetate (compound 22c). MS obsd. (ESI$^-$) [(M−H)$^+$]: 369. (Refer to *Tetrahedron* 1984, 40, 125-135).

Preparation of 1-[(2S,4S,5R)-5-(5-amino-2,7-dioxo-6H-thiazolo[4,5-d]pyrimidin-3-yl)-4-(trifluoromethylsulfonyloxy)tetrahydrofuran-2-yl]propyl acetate

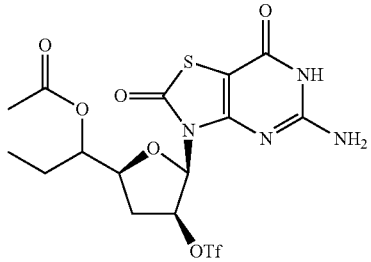

22d

To a stirred solution of 1-[(2S,4S,5R)-5-(5-amino-2,7-dioxo-6H-thiazolo[4,5-d]pyrimidin-3-yl)-4-hydroxy-tetrahydrofuran-2-yl]propyl acetate (compound 22c, 1.76 g, 0.46 mmol) in DCM (30 mL) was added pyridine (154 mg, 1.9 mmol) and trifluoromethanesulfonic anhydride (197 mg, 0.7 mmol). After being stirred at room temperature for 2 hours, the resulting solution was washed with water, brine, dried over Na$_2$SO$_4$. The organic layer was concentrated in vacuo and the residue was purified by column chromatography on silica gel (eluting with 1:10 EtOAc in petroleum ether) to afford 420 mg of 1-[(2S,4S,5R)-5-(5-amino-2,7-dioxo-6H-thiazolo[4,5-d]pyrimidin-3-yl)-4-(trifluoromethylsulfonyloxy)tetrahydrofuran-2-yl]propyl acetate (compound 22d). MS obsd. (ESI$^-$) [(M−H)$^+$]: 502.

Preparation of 1-[(2S,4R,5R)-5-(5-amino-2,7-dioxo-6H-thiazolo[4,5-d]pyrimidin-3-yl)-4-methylsulfanyl-tetrahydrofuran-2-yl]propyl acetate

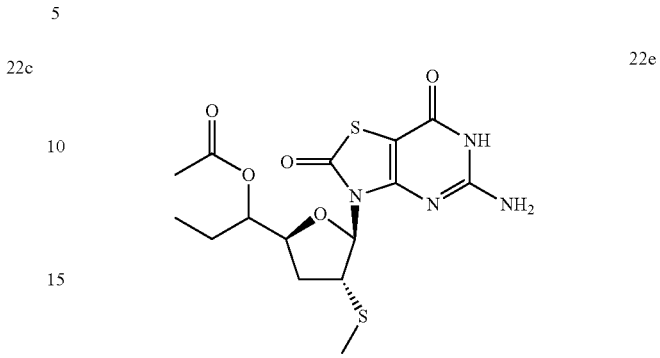

22e

To a stirred solution of 1-[(2S,4S,5R)-5-(5-amino-2,7-dioxo-6H-thiazolo[4,5-d]pyrimidin-3-yl)-4-(trifluoromethylsulfonyloxy)tetrahydrofuran-2-yl]propyl acetate (compound 22d, 420 mg, 0.83 mmol) in DMF (7 mL) was added sodium thiomethoxide (84 mg, 1.2 mmol). After being stirred at room temperature for 2 hours, the resulting solution was diluted with EtOAc, washed with brine, dried over Na$_2$SO$_4$ and concentrated in vacuo to afford crude product of 1-[(2S,4R,5R)-5-(5-amino-2,7-dioxo-6H-thiazolo[4,5-d]pyrimidin-3-yl)-4-methylsulfanyl-tetrahydrofuran-2-yl]propyl acetate (compound 22e), which was used in next step without further purification. MS obsd. (ESI$^-$) [(M−H)$^-$]: 399.

Preparation of 5-amino-3-[(2R,3R,5S)-5-(1-hydroxypropyl)-3-methylsulfanyl-tetrahydrofuran-2-yl]-6H-thiazolo[4,5-d]pyrimidine-2,7-dione

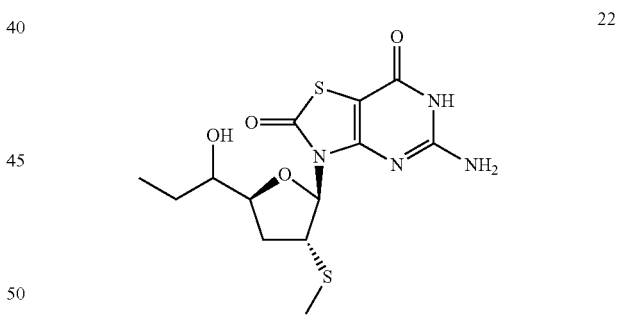

22

To a solution of 1-[(2S,4R,5R)-5-(5-amino-2,7-dioxo-6H-thiazolo[4,5-d]pyrimidin-3-yl)-4-methylsulfanyl-tetrahydrofuran-2-yl]propyl acetate (compound 22e, 200 mg, 0.5 mmol) in methanol (25 mL) was added K$_2$CO$_3$ (272 mg, 2 mmol). After being stirred at room temperature for 12 hours, the reaction mixture was adjusted to pH 7.0 by addition of HOAc (120 mg, 2 mmol), concentrated in vacuo and the residue was purified and separated by preparative HPLC to afford 4.7 mg of Example 22-A and 1.8 mg of Example 22-B as white solid.

Example 22-A: $^1$H NMR (400 MHz, CD$_3$OD) δ ppm: 6.09-6.16 (m, 1H), 4.09-4.16 (m, 1H), 3.97-4.06 (m, 1H), 3.47-3.57 (m, 1H), 2.61-2.72 (m, 1H), 2.13 (s, 3H), 1.95-2.06 (m, 1H), 1.41-1.61 (m, 2H), 1.01 (t, J=7.2 Hz, 3H). MS obsd. (ESI$^-$) [(M−H)$^-$]: 357.

Example 22-B: ¹H NMR (400 MHz, CD₃OD) δ ppm: 6.05-6.12 (m, 1H), 4.01-4.11 (m, 2H), 3.65-3.74 (m, 1H), 2.67-2.78 (m, 1H), 2.12 (s, 3H), 1.98-2.05 (m, 1H), 1.52-1.65 (m, 1H), 1.31-1.47 (m, 1H), 1.01 (t, J=7.2 Hz, 3H). MS obsd. (ESI⁻) [(M−H)⁻]: 357.

Example 23

5-Amino-3-[(2R,3R,5S)-3-azido-5-(1-hydroxypropyl)tetrahydrofuran-2-yl]-6H-thiazolo[4,5-d]pyrimidine-2,7-dione

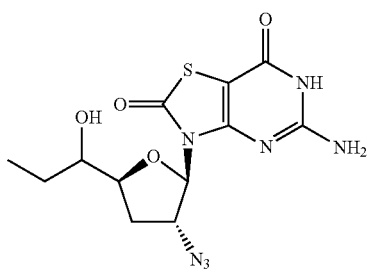

The title compound was prepared in analogy to Example 22, by using sodium azide instead of sodium thiomethoxide. Example 23 was purified and separated by preparative HPLC to afford Example 23-A and Example 23-B as white solid.

Example 23-A: ¹H NMR (400 MHz, CD₃OD) δ ppm: 5.93-5.99 (m, 1H), 4.95-5.00 (m, 1H), 4.06-4.14 (m, 1H), 3.47-3.55 (m, 1H), 2.63-2.75 (m, 1H), 2.03-2.12 (m, 1H), 1.51-1.61 (m, 1H), 1.43-1.51 (m, 1H), 1.01 (t, J=7.40 Hz, 3H). MS obsd. (ESI⁻) [(M−H)⁺]: 352.

Example 23-B: ¹H NMR (400 MHz, CD₃OD) δ ppm: 5.92-5.97 (m, 1H), 4.94-4.98 (m, 1H), 4.02-4.10 (m, 1H), 3.62-3.68 (m, 1H), 2.72-2.80 (m, 1H), 2.06-2.15 (m, 1H), 1.53-1.68 (m, 1H), 1.33-1.45 (m, 1H), 1.00 (t, J=7.40 Hz, 3H). MS obsd. (ESI⁻) [(M−H)⁺]: 352.

Example 24

5-Amino-3-[(2R,3R,5S)-3-hydroxy-5-(1-hydroxyallyl)tetrahydrofuran-2-yl]-6H-thiazolo[4,5-d]pyrimidine-2,7-dione

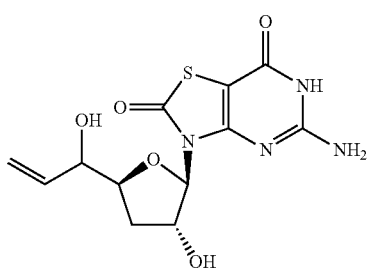

The title compound was prepared in analogy to Example 1, by using ethylene magnesium bromide instead of ethyl magnesium. Example 24 was purified and separated by preparative HPLC to afford Example 24-A and Example 24-B as white solid.

Example 24-A: ¹H NMR (400 MHz, CD₃OD) δ ppm: 5.96-6.01 (m, 1H), 5.86-5.96 (m, 1H), 5.33-5.43 (m, 1H), 5.16-5.22 (m, 1H), 4.91-4.95 (m, 1H), 4.16-4.23 (m, 1H), 4.09-4.16 (m, 1H), 2.53-2.63 (m, 1H), 1.87-1.95 (m, 1H). MS obsd. (ESI⁻) [(M−H)⁺]: 357.

Example 24-B: ¹H NMR (400 MHz, CD₃OD) δ ppm: 5.93-5.95 (m, 1H), 5.84-5.92 (m, 1H), 5.37 (td, J=1.76, 17.32 Hz, 1H), 5.17-5.23 (m, 1H), 4.93-4.99 (m, 1H), 4.29 (br. s., 1H), 4.22 (d, J=4.52 Hz, 1H), 2.57-2.68 (m, 1H), 1.88-1.98 (m, 1H). MS obsd. (ESI⁻) [(M−H)⁺]: 357.

Example 25

5-Amino-3-((2R,3R,5S)-3-azido-5-((S)-1-hydroxyethyl)tetrahydrofuran-2-yl)thiazolo[4,5-d]pyrimidine-2,7(3H,6H)-dione

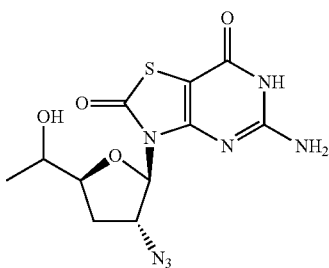

The title compound was prepared according to the following scheme:

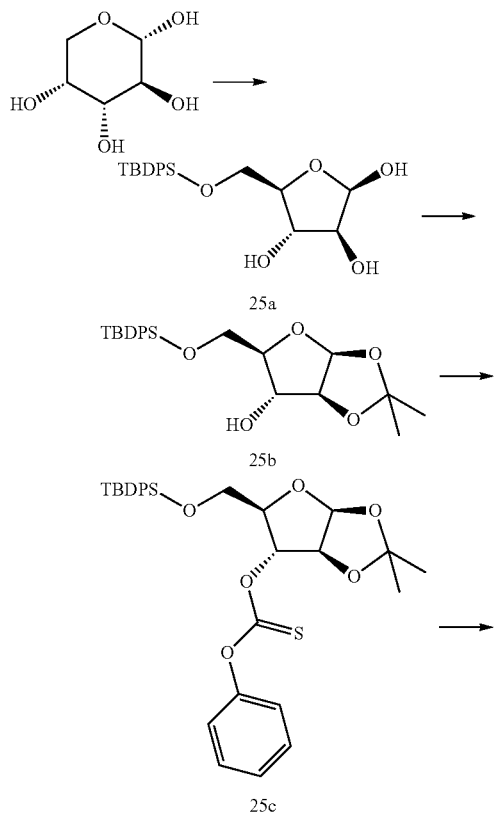

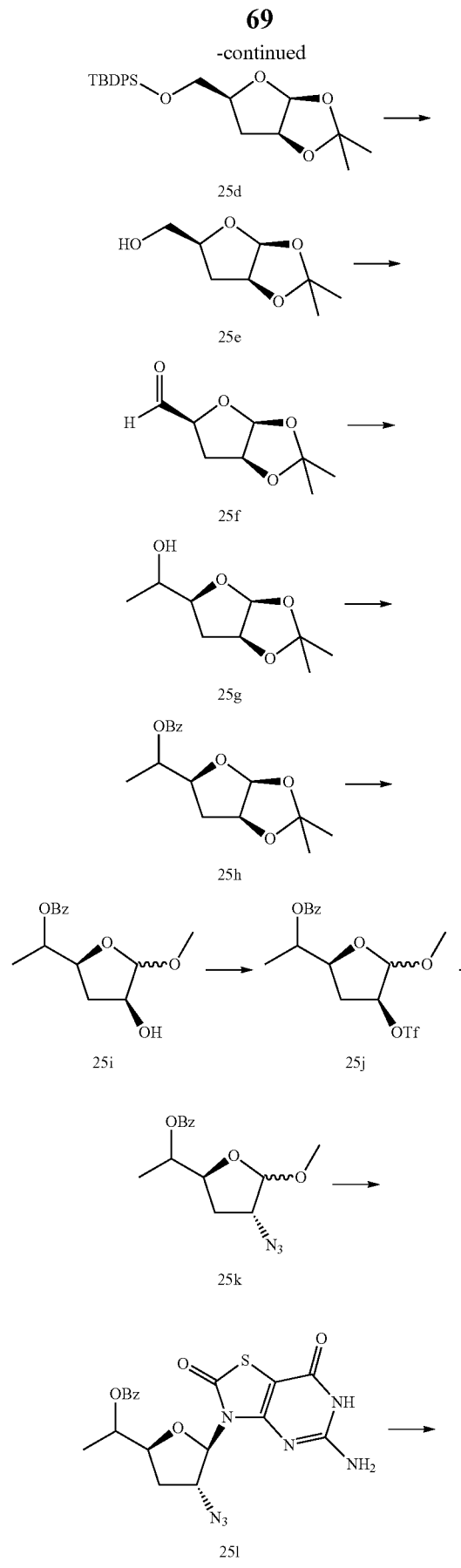

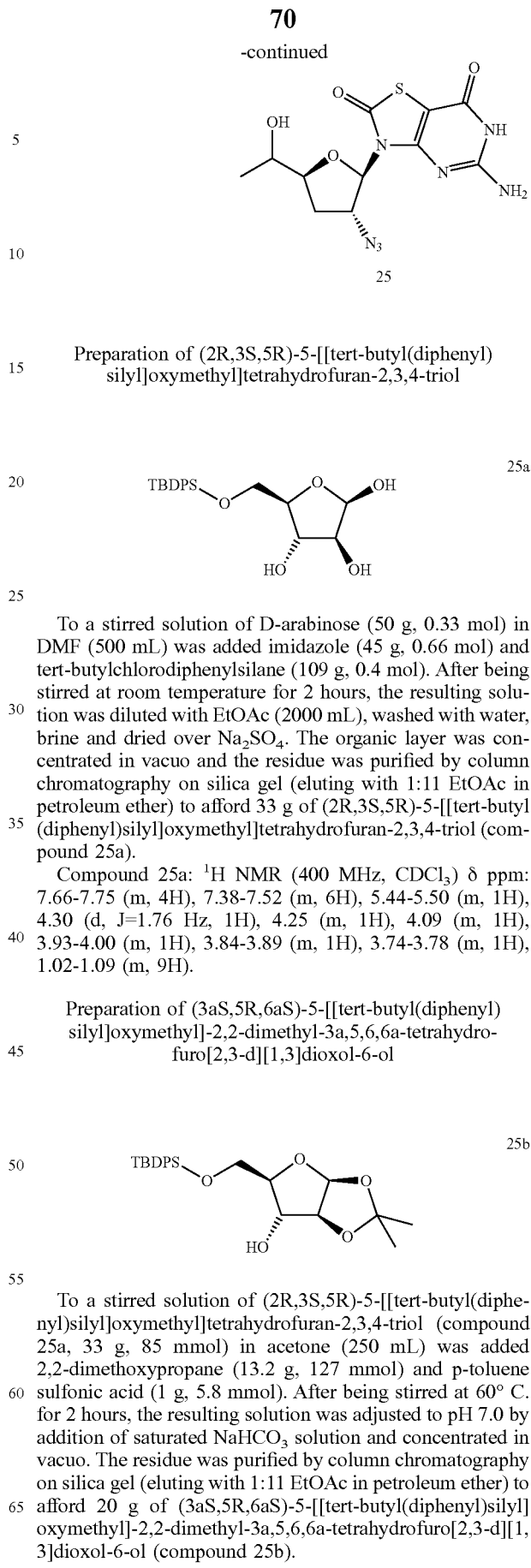

Preparation of (2R,3S,5R)-5-[[tert-butyl(diphenyl)silyl]oxymethyl]tetrahydrofuran-2,3,4-triol To a stirred solution of D-arabinose (50 g, 0.33 mol) in DMF (500 mL) was added imidazole (45 g, 0.66 mol) and tert-butylchlorodiphenylsilane (109 g, 0.4 mol). After being stirred at room temperature for 2 hours, the resulting solution was diluted with EtOAc (2000 mL), washed with water, brine and dried over $Na_2SO_4$. The organic layer was concentrated in vacuo and the residue was purified by column chromatography on silica gel (eluting with 1:11 EtOAc in petroleum ether) to afford 33 g of (2R,3S,5R)-5-[[tert-butyl (diphenyl)silyl]oxymethyl]tetrahydrofuran-2,3,4-triol (compound 25a).

Compound 25a: $^1$H NMR (400 MHz, $CDCl_3$) δ ppm: 7.66-7.75 (m, 4H), 7.38-7.52 (m, 6H), 5.44-5.50 (m, 1H), 4.30 (d, J=1.76 Hz, 1H), 4.25 (m, 1H), 4.09 (m, 1H), 3.93-4.00 (m, 1H), 3.84-3.89 (m, 1H), 3.74-3.78 (m, 1H), 1.02-1.09 (m, 9H).

Preparation of (3aS,5R,6aS)-5-[[tert-butyl(diphenyl)silyl]oxymethyl]-2,2-dimethyl-3a,5,6,6a-tetrahydrofuro[2,3-d][1,3]dioxol-6-ol To a stirred solution of (2R,3S,5R)-5-[[tert-butyl(diphenyl)silyl]oxymethyl]tetrahydrofuran-2,3,4-triol (compound 25a, 33 g, 85 mmol) in acetone (250 mL) was added 2,2-dimethoxypropane (13.2 g, 127 mmol) and p-toluene sulfonic acid (1 g, 5.8 mmol). After being stirred at 60° C. for 2 hours, the resulting solution was adjusted to pH 7.0 by addition of saturated $NaHCO_3$ solution and concentrated in vacuo. The residue was purified by column chromatography on silica gel (eluting with 1:11 EtOAc in petroleum ether) to afford 20 g of (3aS,5R,6aS)-5-[[tert-butyl(diphenyl)silyl] oxymethyl]-2,2-dimethyl-3a,5,6,6a-tetrahydrofuro[2,3-d][1,3]dioxol-6-ol (compound 25b).

Compound 25b: ¹H NMR (400 MHz, CDCl₃) δ ppm: 7.66-7.71 (m, 4H), 7.41 (d, J=7.78 Hz, 6H), 5.87-5.93 (m, 1H), 4.55-4.60 (m, 1H), 4.42-4.49 (m, 1H), 4.04-4.10 (m, 1H), 3.80-3.89 (m, 2H), 1.35 (s, 3H), 1.31 (s, 3H), 1.09 (s, 9H).

Preparation of [(3aS,5R,6aS)-5-[[tert-butyl(diphenyl)silyl]oxymethyl]-2,2-dimethyl-3a,5,6,6a-tetrahydrofuro[2,3-d][1,3]dioxol-6-yl]oxy-phenoxy-methanethione

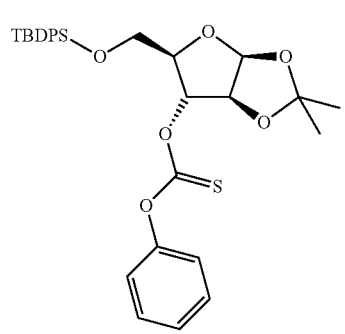

25c

To a solution of (3aS,5R,6aS)-5-[[tert-butyl(diphenyl)silyl]oxymethyl]-2,2-dimethyl-3a,5,6,6a-tetrahydrofuro[2,3-d][1,3]dioxol-6-ol (compound 25b, 23 g, 50 mmol) in DCM (200 mL) was added 0-phenyl chloromethanethioate (10.3 g, 60 mmol) and pyridine (7.9 g, 100 mmol) in DCM. After being stirred at room temperature overnight, the resulting mixture was washed with brine, dried over Na₂SO₄, and concentrated in vacuo. The residue was purified by column chromatography on silica gel (eluting with 0-30% EtOAc in petroleum ether) to afford 20 g of [(3aS,5R,6aS)-5-[[tert-butyl(diphenyl)silyl]oxymethyl]-2,2-dimethyl-3a,5,6,6a-tetrahydrofuro[2,3-d][1,3]dioxol-6-yl]oxy-phenoxy-methanethione (compound 25c). MS obsd. (ESI⁺) [(M+NH₄)⁺]: 582.

Preparation of [(3aS,5S,6aS)-2,2-dimethyl-3a,5,6,6a-tetrahydrofuro[2,3-d][1,3]dioxol-5-yl]methoxy-tert-butyl-diphenyl-silane

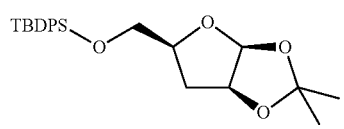

25d

To a solution of [(3aS,5R,6aS)-5-[[tert-butyl(diphenyl)silyl]oxymethyl]-2,2-dimethyl-3a,5,6,6a-tetrahydrofuro[2,3-d][1,3]dioxol-6-yl]oxy-phenoxy-methanethione (compound 25c, 17 g, 30 mmol) in toluene (150 mL) was added tri(trimethylsilyl)silane(16.4 g, 66 mmol) and azodiisobutyronitrile (98 mg, 0.6 mmol), the mixture was heated at 130° C. under nitrogen for 3 hours. After the reaction was completed, the reaction was concentrated in vacuo and the residue was purified by column chromatography on silica gel (eluting with 1:10 EtOAc in petroleum ether) to afford 11 g of [(3aS,5S,6aS)-2,2-dimethyl-3a,5,6,6a-tetrahydrofuro[2,3-d][1,3]dioxol-5-yl]methoxy-tert-butyl-diphenyl-silane (compound 25d).

Compound 25d: ¹H NMR (400 MHz, CDCl₃) δ ppm: 7.70 (qd, J=1.89, 5.87 Hz, 4H), 7.37-7.46 (m, 6H), 5.78-5.83 (m, 1H), 4.72-4.78 (m, 1H), 4.27-4.35 (m, 1H), 3.84 (d, J=6.78 Hz, 2H), 2.25-2.33 (m, 1H), 2.13-2.19 (m, 1H), 1.35 (s, 3H), 1.30 (s, 3H), 1.08 (s, 9H).

Preparation of [(3aS,5S,6aS)-2,2-dimethyl-3a,5,6,6a-tetrahydrofuro[2,3-d][1,3]dioxol-5-yl]methanol

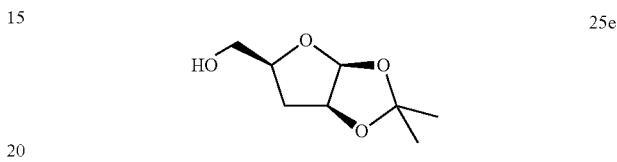

25e

To a solution of [(3aS,5S,6aS)-2,2-dimethyl-3a,5,6,6a-tetrahydrofuro[2,3-d][1,3]dioxol-5-yl]methoxy-tert-butyl-diphenyl-silane (compound 25d, 11 g, 26.6 mmol) in THF (100 mL) was added TBAF solution (1M in THF, 6 mL, 6 mmol) with stirring. After being stirred at room temperature for 4 hours, the reaction solution was washed with saturated NH₄Cl solution, dried over Na₂SO₄, concentrated in vacuo and the residue was purified by column chromatography on silica gel (eluting with 1:2 EtOAc in petroleum ether) to afford 5.8 g of [(3aS,5S,6aS)-2,2-dimethyl-3a,5,6,6a-tetrahydrofuro[2,3-d][1,3]dioxol-5-yl]methanol (compound 25e).

Compound 25e: ¹H NMR (400 MHz, CDCl₃) δ ppm: 5.81-5.89 (m, 1H), 4.75-4.83 (m, 1H), 4.32-4.41 (m, 1H), 3.81-3.91 (m, 1H), 3.60-3.70 (m, 1H), 2.21-2.28 (m, 1H), 1.97-2.09 (m, 1H), 1.57-1.59 (s, 6H).

Preparation of (3aS,5S,6aS)-2,2-dimethyl-3a,5,6,6a-tetrahydrofuro[2,3-d][1,3]dioxole-5-carbaldehyde

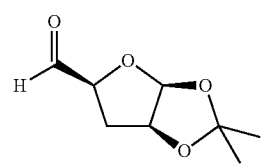

25f

To a stirred solution of [(3aS,5S,6aS)-2,2-dimethyl-3a,5,6,6a-tetrahydrofuro[2,3-d][1,3]dioxol-5-yl]methanol (compound 25e, 2 g, 11.5 mmol) in THF (20 mL) was added Dess-Martine periodinane (7.2 g, 17.2 mmol). After being stirred room temperature for 2 hours, the resulting solution was filtered and the filtrate was concentrated in vacuo. The residue was purified by column chromatography on silica gel (eluting with 1:3 EtOAc in petroleum ether) to afford 1.2 g of (3aS,5S,6aS)-2,2-dimethyl-3a,5,6,6a-tetrahydrofuro[2,3-d][1,3]dioxole-5-carbaldehyde (compound 25f). MS obsd. (ESI⁺) [(M+NH₄)⁺]: 190.

Preparation of 1-[(3aS,5S,6aS)-2,2-dimethyl-3a,5,6,6a-tetrahydrofuro[2,3-d][1,3]dioxol-5-yl]ethanol

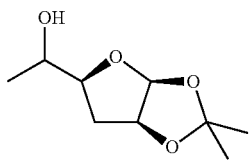

25g

To a solution of (3aS,5S,6aS)-2,2-dimethyl-3a,5,6,6a-tetrahydrofuro[2,3-d][1,3]dioxole-5-carbaldehyde (compound 25f, 800 mg, 1 mmol) in THF (20 mL) was added methyl magnesium bromide (2M in THF, 0.7 mL, 1.4 mmol) at −20° C. under argon. After being stirred at −20° C. for 20 hours, the reaction was quenched by saturated NH$_4$Cl solution, extracted with EtOAc (30 mL) three times. The organic layers were combined and concentrated in vacuo to afford 400 mg crude product of 1-[(3aS,5S,6aS)-2,2-dimethyl-3a,5,6,6a-tetrahydro furo[2,3-d][1,3]dioxol-5-yl]ethanol (compound 25g), which was used in next step without further purification. MS obsd. (ESI$^+$) [(M+NH$_4$)$^+$]: 206.

Preparation of 1-[(3aS,5S,6aS)-2,2-dimethyl-3a,5,6,6a-tetrahydrofuro[2,3-d][1,3]dioxol-5-yl]ethyl benzoate

25h

To a cooled solution of 1-[(3aS,5S,6aS)-2,2-dimethyl-3a,5,6,6a-tetrahydrofuro[2,3-d][1,3]dioxol-5-yl]ethanol (compound 25g, 200 mg, 1.06 mmol) in DCM (8 mL) was added benzoyl chloride (178 mg, 1.28 mmol) and DMAP (259 mg, 2 mmol). After the addition, the mixture was warmed naturally to room temperature and stirred at room temperature overnight. The resulting mixture was diluted with EtOAc and washed with a saturated aqueous solution of NH$_4$Cl. The organic layer was dried over Na$_2$SO$_4$ and concentrated in vacuo. The residue was purified by column chromatography on silica gel (eluting with 1:3 EtOAc in petroleum ether) to afford 170 mg of 1-[(3aS,5S,6aS)-2,2-dimethyl-3a,5,6,6a-tetrahydrofuro[2,3-d][1,3]dioxol-5-yl]ethyl benzoate (compound 25h).

Compound 25h: $^1$H NMR (400 MHz, CDCl$_3$) δ ppm: 8.05 (s, 2H), 7.56-7.63 (m, 1H), 7.46 (s, 2H), 5.85 (d, J=4.02 Hz, 1H), 5.38-5.52 (m, 1H), 4.73-4.83 (m, 1H), 4.13-4.25 (m, 1H), 2.22 (d, J=4.77 Hz, 2H), 1.62 (s, 3H), 1.46 (d, J=6.27 Hz, 3H), 1.34 (s, 3H).

Preparation of 1-[(2S,4S)-4-hydroxy-5-methoxy-tetrahydrofuran-2-yl]ethyl benzoate

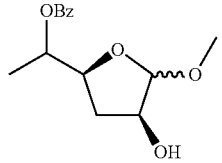

25i

A solution of 1-[(3aS,5S,6aS)-2,2-dimethyl-3a,5,6,6a-tetrahydrofuro[2,3-d][1,3]dioxol-5-yl]ethyl benzoate (compound 25h, 170 mg, 18 mmol) in the HCl solution (0.1N in MeOH, 3 mL) was stirred at room temperature overnight. The resulting mixture was neutralized by ammonium hydroxide and concentrated in vacuo. The residue was suspended in EtOAc and then filtered, the filtrate was concentrated in vacuo to afford 148 mg crude product of 1-[(2S,4S)-4-hydroxy-5-methoxy-tetrahydrofuran-2-yl] ethyl benzoate (compound 25i), which was used in the next step directly. MS obsd. (ESI$^+$) [(M+H)$^+$]: 267.

Preparation of 1-[(2S,4S)-5-methoxy-4-(trifluoromethylsulfonyloxy)tetrahydrofuran-2-yl]ethyl benzoate

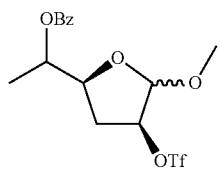

25j

To a solution of 1-[(2S,4S)-4-hydroxy-5-methoxy-tetrahydrofuran-2-yl]ethyl benzoate (compound 25i, 483 mg) and DMAP (885 mg, 7.3 mmol) in DCM (20 mL) was added trifluoromethanesulfonic anhydride (665 mg, 2.36 mmol) at 0° C. After being stirred at room temperature for 0.5 hr, the reaction was quenched by saturated NaHCO$_3$ solution and extracted with DCM three times. The organic layers were combined, dried over Na$_2$SO$_4$ and concentrated in vacuo to afford 740 mg crude product of 1-[(2S,4S)-5-methoxy-4-(trifluoromethylsulfonyloxy)tetrahydrofuran-2-yl]ethyl benzoate (compound 25j) as an oil, which was used in next step directly without further purification. MS obsd. (ESI$^+$) [(M+H)$^+$]: 400.

Preparation of 1-[(2S,4R)-4-azido-5-methoxy-tetrahydrofuran-2-yl]ethyl benzoate

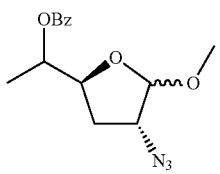

25k

To a solution of 1-[(2S,4S)-5-methoxy-4-(trifluoromethylsulfonyloxy)tetrahydrofuran-2-yl]ethyl benzoate (compound 25j, 400 mg, 1 mmol) in DMF (2 mL) was added sodium azide (65 mg, 1.05 mmol) at room temperature and the mixture was stirred at room temperature for 16 hours. The reaction mixture was partitioned between EtOAc and H$_2$O, the organic layer was separated and the aqueous layer was extracted with EtOAc twice. The organic layers were combined, washed with brine, dried over Na$_2$SO$_4$ and concentrated in vacuo to afford 600 mg crude product of 1-[(2S,4R)-4-azido-5-methoxy-tetrahydrofuran-2-yl]ethyl benzoate (compound 25k), which was used in next step without further purification.

Preparation of 1-[(2S,4R,5R)-5-(5-amino-2,7-dioxo-6H-thiazolo[4,5-d]pyrimidin-3-yl)-4-azido-tetrahydrofuran-2-yl]ethyl benzoate

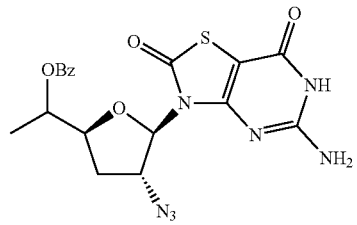

25l

To a suspension of 5-amino-3,6-dihydrothiazolo[4,5-d]pyrimidine-2,7-dione (186 mg, 1 mmol) in ACN (10 mL) was added BSA (630 mg, 3 mmol). The resulting reaction mixture was then stirred at 70° C. under argon for 0.5 hour to form a clear solution. After the solution was cooled to room temperature, 1-[(2S,4R)-4-azido-5-methoxy-tetrahydrofuran-2-yl]ethyl benzoate (compound 25k, 300 mg, 1.0 mmol) and TMSOTf (1.15 g, 5 mmol) were added in sequence. After being heated at 70° C. for 14 hours, the solvent was removed in vacuo. The residue was partitioned between EtOAc and saturated NaHCO$_3$ solution (30 mL). The organic layer was separated and the aqueous phase was extracted with EtOAc (30 mL) twice. The combined organic layers were washed with brine, dried over Na$_2$SO$_4$ and concentrated in vacuo to afford 600 mg crude product of 1-[(2S,4R,5R)-5-(5-amino-2,7-dioxo-6H-thiazolo[4,5-d]pyrimidin-3-yl)-4-azido-tetrahydrofuran-2-yl]ethyl benzoate (compound 25l), which was used in next step without further purification. MS obsd. (ESI$^+$) [(M+H)$^+$]: 442.

Preparation of 5-amino-3-[(2R,3R,5S)-3-azido-5-(1-hydroxyethyl)tetrahydrofuran-2-yl]-6H-thiazolo[4,5-d]pyrimidine-2,7-dione

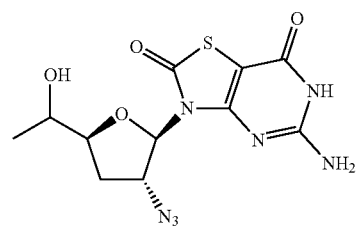

25

To a solution of 1-[(2S,4R,5R)-5-(5-amino-2,7-dioxo-6H-thiazolo[4,5-d]pyrimidin-3-yl)-4-azido-tetrahydrofuran-2-yl]ethyl benzoate (compound 25l, 600 mg, crude) in MeOH (8 mL) was added K$_2$CO$_3$ (187 mg, 1.4 mmol). After being stirred at room temperature for 5 hours, the reaction mixture was concentrated in vacuo and the residue was purified by preparative HPLC to afford 30 mg of 5-amino-3-[(2R,3R,5S)-3-azido-5-(1-hydroxyethyl)tetrahydrofuran-2-yl]-6H-thiazolo[4,5-d]pyrimidine-2,7-dione (Example 25) as a white solid.

Example 25: $^1$H NMR (400 MHz, d$_6$-DMSO) δ ppm: 11.26 (s, 1H), 6.96 (br. s., 2H), 5.76 (d, J=3.3 Hz, 1H), 5.03 (dt, J=7.4, 2.8 Hz, 1H), 4.71 (d, J=5.0 Hz, 1H), 3.80 (dt, J=9.2, 6.1 Hz, 1H), 3.57-3.67 (m, 1H), 2.53-2.68 (m, 1H), 2.04 (ddd, J=13.2, 6.0, 2.6 Hz, 1H), 1.05 (d, J=6.3 Hz, 3H). MS obsd. (ESI$^-$) [(M−H)$^+$]: 338.

Example 26

3-[(2R,3R,5S)-3-allyl-5-(1-hydroxypropyl)tetrahydrofuran-2-yl]-5-amino-6H-thiazolo[4,5-d]pyrimidine-2,7-dione

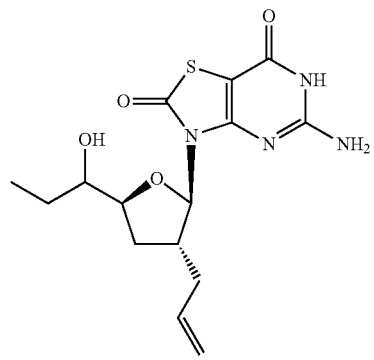

26

The title compound was prepared according to the following scheme:

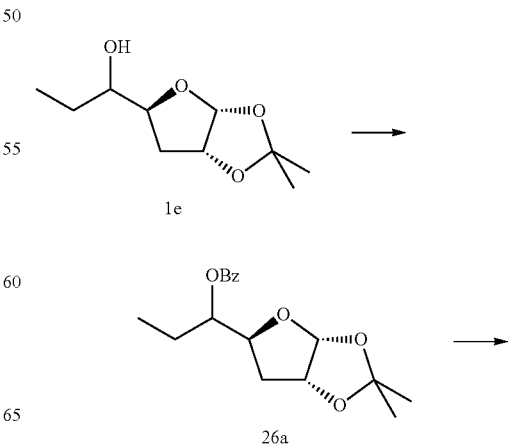

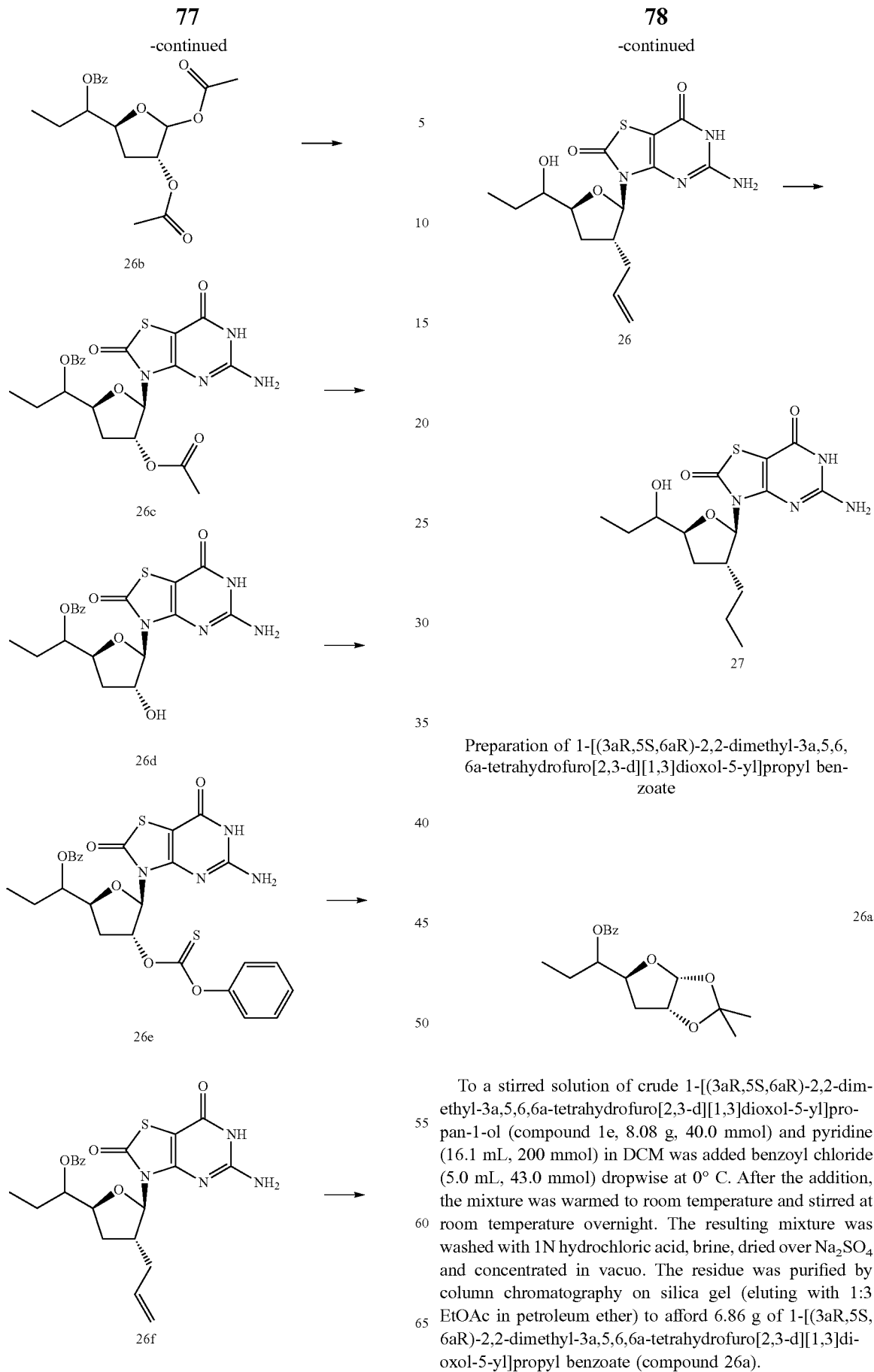

Preparation of 1-[(3aR,5S,6aR)-2,2-dimethyl-3a,5,6,6a-tetrahydrofuro[2,3-d][1,3]dioxol-5-yl]propyl benzoate To a stirred solution of crude 1-[(3aR,5S,6aR)-2,2-dimethyl-3a,5,6,6a-tetrahydrofuro[2,3-d][1,3]dioxol-5-yl]propan-1-ol (compound 1e, 8.08 g, 40.0 mmol) and pyridine (16.1 mL, 200 mmol) in DCM was added benzoyl chloride (5.0 mL, 43.0 mmol) dropwise at 0° C. After the addition, the mixture was warmed to room temperature and stirred at room temperature overnight. The resulting mixture was washed with 1N hydrochloric acid, brine, dried over $Na_2SO_4$ and concentrated in vacuo. The residue was purified by column chromatography on silica gel (eluting with 1:3 EtOAc in petroleum ether) to afford 6.86 g of 1-[(3aR,5S,6aR)-2,2-dimethyl-3a,5,6,6a-tetrahydrofuro[2,3-d][1,3]dioxol-5-yl]propyl benzoate (compound 26a).

Preparation of 1-[(2S,4R)-4,5-diacetoxytetrahydrofuran-2-yl]propyl benzoate

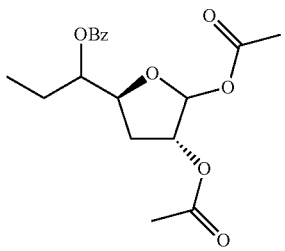

26b

To a stirred solution of 1-[(3aR,5S,6aR)-2,2-dimethyl-3a,5,6,6a-tetrahydrofuro[2,3-d][1,3]dioxol-5-yl]propyl benzoate (compound 26a, 6.73 g, 22.0 mmol) and acetic anhydride (11 mL) in acetic acid (44 mL) and chloroform (11 mL) was added concentrated sulfuric acid (200 uL) dropwise. After being stirred at room temperature overnight, the resulted mixture was diluted with EtOAc (100 mL) and washed with a saturated aqueous solution of NaHCO$_3$ (100 mL) three times. The combined organic layers were dried over Na$_2$SO$_4$ and concentrated in vacuo. The residue was purified by column chromatography on silica gel (eluting with 1:20 to 1:10 EtOAc in petroleum ether) to afford 5.1 g 1-[(2S,4R)-4,5-diacetoxytetrahydrofuran-2-yl]propyl benzoate (compound 26b) as a viscous oil.

Preparation of 1-[(2S,4R,5R)-4-acetoxy-5-(5-amino-2,7-dioxo-6H-thiazolo[4,5-d]pyrimidin-3-yl)tetrahydrofuran-2-yl]propyl benzoate

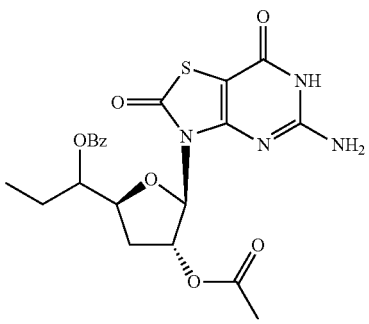

26c

To a suspension of 5-amino-3,6-dihydrothiazolo[4,5-d]pyrimidine-2,7-dione (2.82 g, 16.8 mmol) in ACN (100 mL) was added BSA (10.4 mL, 42 mmol). The resulting reaction mixture was then stirred at 70° C. under argon for 0.5 hour to form a clear solution. After the solution was cooled to room temperature, 1-[(2S,4R)-4,5-diacetoxytetrahydrofuran-2-yl]propyl benzoate (compound 26b, 4.9 g, 14.0 mmol) and TMSOTf (4.7 mL, 2.3 21 mmol) were added in sequence. After being heated with stirring at 70° C. for 14 hours, the solvent was removed in vacuo. The residue was partitioned between EtOAc and saturated NaHCO$_3$ solution (30 mL). The organic layer was separated and the aqueous phase was extracted with EtOAc (30 mL) twice. The combined organic layers were washed with brine, dried over Na$_2$SO$_4$ and concentrated in vacuo. The residue was purified by column chromatography on silica gel (eluting with 1:200 methanol in DCM) to afford 5.27 g crude product of 1-[(2S,4R,5R)-4-acetoxy-5-(5-amino-2,7-dioxo-6H-thiazolo[4,5-d]pyrimidin-3-yl)tetrahydrofuran-2-yl]propyl benzoate (compound 26c) as a light yellow solid. MS obsd. (ESI$^+$) [(M+H)$^+$]: 475.

Preparation of 1-[(2S,4R,5R)-5-(5-amino-2,7-dioxo-6H-thiazolo[4,5-d]pyrimidin-3-yl)-4-hydroxy-tetrahydrofuran-2-yl]propyl benzoate

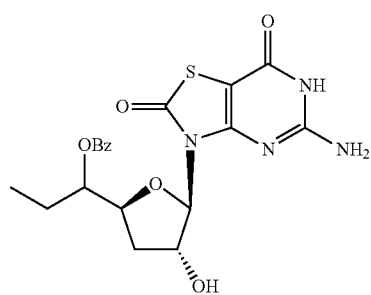

26d

To a solution of 1-[(2S,4R,5R)-4-acetoxy-5-(5-amino-2,7-dioxo-6H-thiazolo[4,5-d]pyrimidin-3-yl)tetrahydrofuran-2-yl]propyl benzoate (compound 26c, 4.98 g, 10.5 mmol) in methanol (105 mL) was added K$_2$CO$_3$ (1.38 g, 10.0 mmol). After being stirred at room temperature for 1 hour, the reaction was adjusted to pH 7.0 with HOAc (1.2 g, 20.0 mmol), concentrated in vacuo and the residue was purified by column chromatography on silica gel (eluting with 1:200 methanol in DCM) to afford 4.5 g of 1-[(2S,4R,5R)-5-(5-amino-2,7-dioxo-6H-thiazolo[4,5-d]pyrimidin-3-yl)-4-hydroxy-tetrahydrofuran-2-yl]propyl benzoate (compound 26d) as a light brown solid. MS obsd. (ESI$^+$) [(M+H)$^+$]: 433.

Preparation of 1-[(2S,4R,5R)-5-(5-amino-2,7-dioxo-6H-thiazolo[4,5-d]pyrimidin-3-yl)-4-phenoxycarbothioyloxy-tetrahydrofuran-2-yl]propyl benzoate

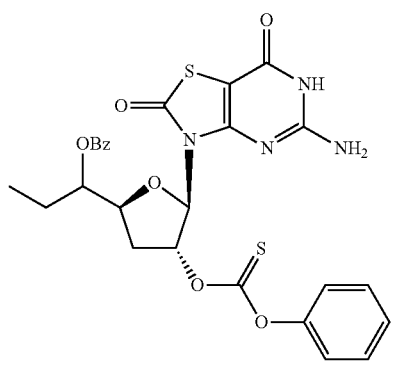

26e

To a solution of 1-[(2S,4R,5R)-5-(5-amino-2,7-dioxo-6H-thiazolo[4,5-d]pyrimidin-3-yl)-4-hydroxy-tetrahydrofuran-2-yl]propyl benzoate (compound 26d, 4.32 g, 10.0 mmol) in DCM (60 mL) was added DMAP (2.44 g, 20 mmol) and O-phenyl chloromethanethioate (1.6 mL, 12.0 mmol) with stirring. After being stirred at room temperature for 2 hours, the resulting solution was concentrated in vacuo and the residue was purified by column chromatography on silica gel (eluting with 1:10 to 1:1 EtOAc in petroleum ether) to afford 1.9 g of 1-[(2S,4R,5R)-5-(5-amino-2,7-dioxo-6H-thiazolo[4,5-d]pyrimidin-3-yl)-4-phenoxycarbothioyloxy-tetrahydrofuran-2-yl]propyl benzoate (compound 26e). MS obsd. (ESI+) [(M+H)+]: 569.

Preparation of 1-[(2S,4R,5R)-4-allyl-5-(5-amino-2,7-dioxo-6H-thiazolo[4,5-d]pyrimidin-3-yl)tetrahydrofuran-2-yl]propyl benzoate

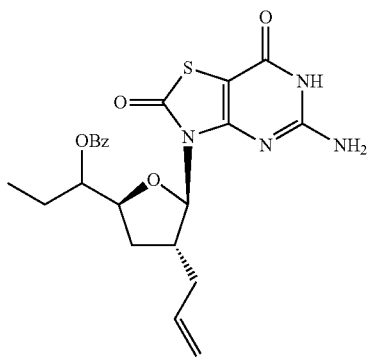

26f

A mixture of 1-[(2S,4R,5R)-5-(5-amino-2,7-dioxo-6H-thiazolo[4,5-d]pyrimidin-3-yl)-4-phenoxycarbothioyloxy-tetrahydrofuran-2-yl]propyl benzoate (compound 26e, 1.14 g, 2.0 mmol), 2,2'-azobisisobutyronitrile (168 mg, 1 mmol) and allyl(tributyl)stannane (3.08 mL, 10 mmol) in anhydrous toluene (15 mL) was degassed with argon and then heated with stirring at 80° C. for 4 hours. The resulting mixture was stirred with saturated aqueous NH4F at room temperature for 2 hours and extracted with DCM twice. The combined organic layers were dried over Na2SO4, concentrated in vacuo and the residue was purified by column chromatography on silica gel (eluting with 1:3 EtOAc in petroleum ether) to afford 820 mg of 1-[(2S,4R,5R)-4-allyl-5-(5-amino-2,7-dioxo-6H-thiazolo[4,5-d]pyrimidin-3-yl)tetrahydrofuran-2-yl]propyl benzoate (compound 26f) as a brown solid. MS obsd. (ESI+) [(M+H)+]: 457.

Preparation of 3-[(2R,3R,5S)-3-allyl-5-(1-hydroxypropyl)tetrahydrofuran-2-yl]-5-amino-6H-thiazolo[4,5-d]pyrimidine-2,7-dione To a solution of 1-[(2S,4R,5R)-4-allyl-5-(5-amino-2,7-dioxo-6H-thiazolo[4,5-d]pyrimidin-3-yl)tetrahydrofuran-2-yl]propyl benzoate (compound 26f, 800 mg, 1.75 mmol) in methanol (25 mL) was added K2CO3 (483 mg, 3.5 mmol). After being stirred at room temperature for 12 hours, the reaction was diluted by saturated NH4Cl solution and extracted with DCM. The organic layers were combined and concentrated in vacuo. The residue was purified by preparative HPLC to afford 200 mg of 3-[(2R,3R,5S)-3-allyl-5-(1-hydroxypropyl)tetrahydrofuran-2-yl]-5-amino-6H-thiazolo[4,5-d]pyrimidine-2,7-dione (Example 26). 100 mg of Example 26 was further separated by supercritical fluid chromatography (SFC) to afford 32.0 mg of Example 26-A and 30.8 mg of Example 26-B as white solid.

Example 26: 1H NMR (400 MHz, d6-DMSO) δ ppm: 11.32 (br. s., 1H), 6.89 (br. s., 2H), 5.64-5.81 (m, 2H), 4.92-5.10 (m, 2H), 4.45-4.63 (m, 1H), 3.74-3.93 (m, 1H), 3.37-3.48 (m, 1H), 2.97-3.14 (m, 1H), 2.12-2.39 (m, 3H), 1.61-1.79 (m, 1H), 1.36-1.52 (m, 1H), 1.14-1.29 (m, 1H), 0.88 (q, J=7.36 Hz, 3H) MS obsd. (ESI+) [(M+H)+]: 353.

Example 26-A: 1H NMR (400 MHz, d6-DMSO) δ ppm: 11.24 (br. s., 1H), 6.87 (br. s., 2H), 5.66-5.80 (m, 2H), 4.95-5.11 (m, 2H), 4.45 (d, J=6.53 Hz, 1H), 3.82-3.93 (m, 1H), 3.39-3.49 (m, 1H), 2.95-3.06 (m, 1H), 2.14-2.30 (m, 3H), 1.66 (ddd, J=4.89, 7.09, 12.11 Hz, 1H), 1.34-1.49 (m, 1H), 1.18-1.33 (m, 1H), 0.88 (t, J=7.28 Hz, 3H). MS obsd. (ESI+) [(M+H)+]: 353.

Example 26-B: 1H NMR (400 MHz, d6-DMSO) δ ppm: 11.28 (br. s., 1H), 6.87 (br. s., 2H), 5.65-5.79 (m, 2H), 4.92-5.10 (m, 2H), 4.57 (d, J=4.77 Hz, 1H), 3.78 (q, J=6.78 Hz, 1H), 3.39-3.50 (m, 1H), 3.03-3.15 (m, 1H), 2.35 (ddd, J=5.77, 8.66, 12.42 Hz, 1H), 2.16 (t, J=7.15 Hz, 2H), 1.73 (td, J=7.34, 12.42 Hz, 1H), 1.42-1.55 (m, 1H), 1.14-1.28 (m, 1H), 0.87 (t, J=7.28 Hz, 3H). MS obsd. (ESI+) [(M+H)+]: 353.

Example 27

Example 27-A and Example 27-B: 5-amino-3-[(2R,3R,5S)-5-[(1S)-1-hydroxypropyl]-3-propyl-tetrahydrofuran-2-yl]-6H-thiazolo[4,5-d]pyrimidine-2,7-dione and 5-amino-3-[(2R,3R,5S)-5-[(1R)-1-hydroxypropyl]-3-propyl-tetrahydrofuran-2-yl]-6H-thiazolo[4,5-d]pyrimidine-2,7-dione

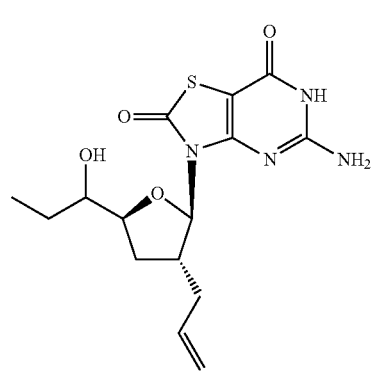

26

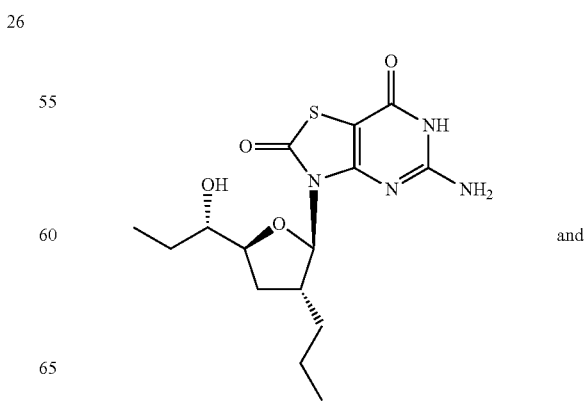

and

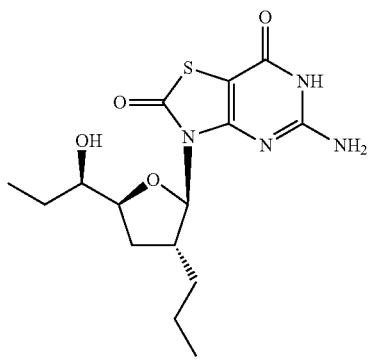

A solution of Example 26-A (50 mg, 0.15 mmol) in methanol was stirred with PtO$_2$ (10 mg) under hydrogen atmosphere for 4 hours at room temperature. The reaction mixture was filtered to remove PtO$_2$. The filtrate was concentrated in vacuo and the residue was purified and separated by preparative HPLC to afford 32.1 mg of Example 27-A as a white solid.

Example 27-A: $^1$H NMR (400 MHz, d$_6$-DMSO) δ ppm: 10.86-11.27 (br. s, 1H), 6.81-7.00 (br. s, 2H), 5.64-5.72 (m, 1H), 4.41-4.49 (m, 1H), 3.82-3.91 (m, 1H), 2.81-2.95 (m, 1H), 2.16-2.30 (m, 1H), 1.57-1.69 (m, 1H), 1.34-1.50 (m, 4H), 1.22-1.34 (m, 4H), 0.79-0.94 (m, 6H). MS obsd. (ESI$^+$) [(M+H)$^+$]: 355.

Example 27-B was prepared in analogy to Example 27-A, by using Example 26-B instead of Example 26-A.

Example 27-B: $^1$H NMR (400 MHz, d$_6$-DMSO) δ ppm: 11.18-11.47 (br. s., 1H), 6.79-7.02 (br. s., 2H), 5.61-5.75 (m, 1H), 4.57 (d, J=4.27 Hz, 1H), 3.69-3.85 (m, 1H), 3.45 (m, 1H), 2.94-3.08 (m, 1H), 2.35 (m, 1H), 1.71 (m, 1H), 1.42-1.55 (m, 1H), 1.31-1.42 (m, 2H), 1.12-1.31 (m, 3H), 0.69-0.95 (m, 6H). MS obsd. (ESI$^+$) [(M+H)$^+$]: 355.

Example 28

5-amino-3-[(2R,3R,5S)-5-[(1S)-1-hydroxypropyl]-3-methyl-tetrahydrofuran-2-yl]-6H-thiazolo[4,5-d]pyrimidine-2,7-dione

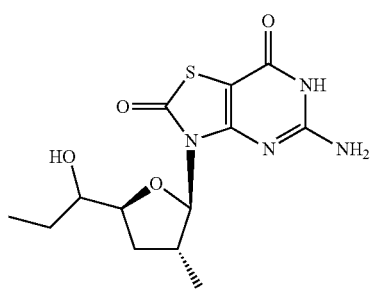

The title compound was prepared according to the following scheme:

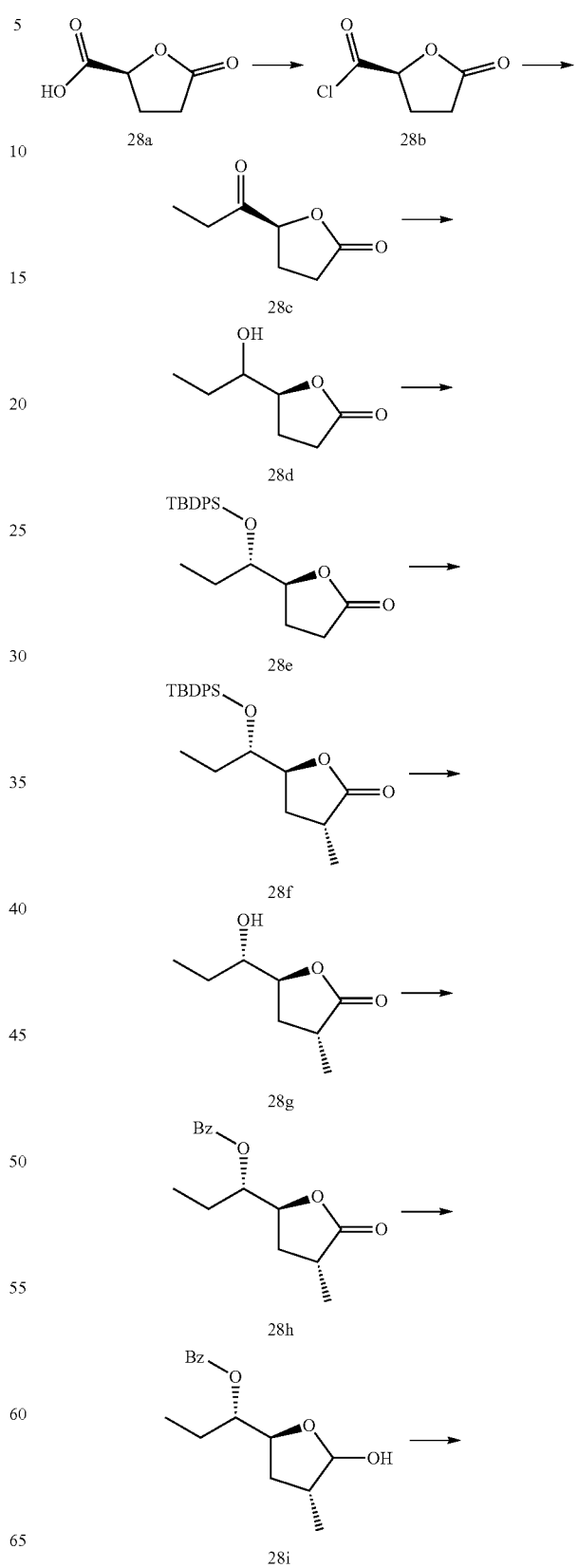

-continued

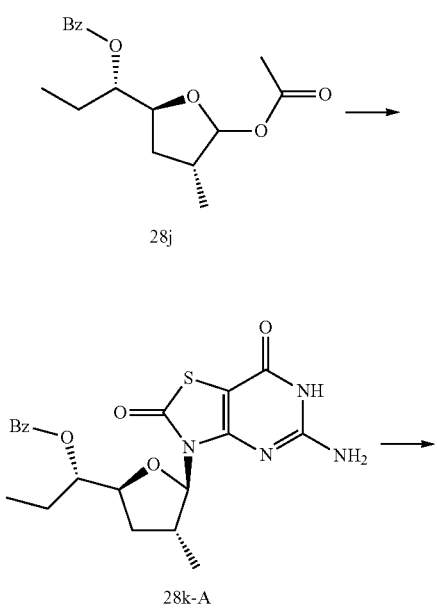

Preparation of
(2S)-5-oxotetrahydrofuran-2-carboxylic acid

To a solution of (S)-2-aminopentanedioic acid (100 g, 680 mmol) in H₂O (500 mL) was added HCl (140 mL, 1.6 mol) and then NaNO₂ (70.4 g, 1.02 mol) in H₂O (100 mL) was added slowly at −5° C.-0° C., and the reaction mixture was stirred at room temperature for 24 hours. The solvent was concentrated in vacuo below 50° C. The residue was suspended in EtOAc (500 mL) and filtered. The filtrate was dried over Na₂SO₄ and concentrated in vacuo to afford 56 g crude product of (2S)-5-oxotetrahydrofuran-2-carboxylic acid (compound 28a) as yellow oil, which was used in next step without further purification.

Preparation of
(2S)-5-oxotetrahydrofuran-2-carbonyl chloride

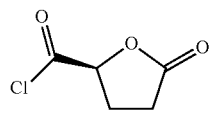

To a solution of (2S)-5-oxotetrahydrofuran-2-carboxylic acid (compound 28a, 70 g, 539 mmol) and a drop of DMF in anhydrous DCM (500 mL) was added oxalyl dichloride (137 g, 1.07 mol) dropwise. The reaction mixture was stirred at room temperature for 3 hours. The reaction was then concentrated in vacuo to afford 70 g crude product of (2S)-5-oxotetrahydrofuran-2-carbonyl chloride (compound 28b), which was used in next step without further purification.

Preparation of
(5S)-5-propanoyltetrahydrofuran-2-one

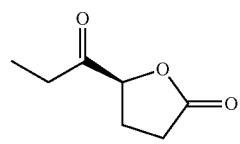

To a solution of (2S)-5-oxotetrahydrofuran-2-carbonyl chloride (compound 28b, 70 g, 473 mmol) in dry THF (400 mL) was added ethylmagnesium bromide (173 mL, 520 mmol, 3M in THF) slowly at −78° C. under N₂. After addition, the reaction mixture was stirred at −78° C. for another 2 hours. The mixture was then quenched with saturated NH₄Cl solution and extracted with EtOAc (500 mL) twice. The combined organic layers were concentrated in vacuo and the residue was purified by column chromatography on silica gel (eluting with 1:7 to 1:3 EtOAc in petroleum ether) to afford 35 g of (5S)-5-propanoyltetrahydrofuran-2-one (compound 28c) as a light yellow oil.

Preparation of
(5S)-5-(1-hydroxypropyl)tetrahydrofuran-2-one

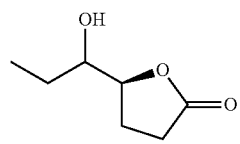

To a solution of (5S)-5-propanoyltetrahydrofuran-2-one (compound 28c, 35 g, 246.5 mmol) was added L-selectride (320 mL, 320 mmol, 1 M in THF) at −78° C. under N₂. After addition, the reaction mixture was stirred at −78° C. for 2 hours. The reaction mixture was then quenched with 2N HCl (200 mL) and extracted with EtOAc (400 mL) twice. The combined organic layers were washed with brine (100 mL), concentrated in vacuo and the residue was purified by column chromatography on silica gel (eluting with 1:7 to 1:3 EtOAc in petroleum ether) to afford 20 g of (5S)-5-(1-hydroxypropyl)tetrahydrofuran-2-one (compound 28d) as a yellow oil. (Refer to *Eur. J. Med. Chem.* 1997, 32, 617-623).

Preparation of (5S)-5-[(1S)-1-[tert-butyhdiphenyl)silyl]oxypropyl]tetrahydrofuran-2-one and (5S)-5-[(1R)-1-[tert-butyhdiphenyl)silyl]oxypropyl]tetrahydrofuran-2-one

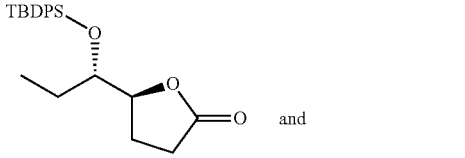

28e-S and

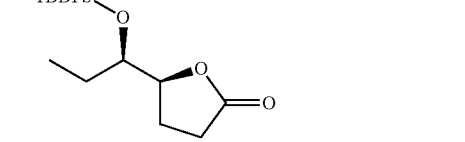

28e-R

To a solution of (5S)-5-(1-hydroxypropyl)tetrahydrofuran-2-one (compound 28d, 9 g, 62.5 mmol) in DMF (100 mL) was added tert-butylchlorodiphenylsilane (42.8 g, 156 mmol) and imidazole (10.6 g, 156 mmol) under $N_2$. After being stirred at 50° C. for 12 hours, the mixture was diluted with water and extracted with EtOAc. The combined organic layers were washed with brine (100 mL) and concentrated in vacuo. The residue was purified by column chromatography on silica gel (eluting with 1:20 to 1:3 EtOAc in petroleum ether) to afford 18 g of (5S)-5-[(1-[tert-butyl(diphenyl)silyl]oxypropyl]tetrahydrofuran-2-one. 10 g of the mixture was further purified and separated by SFC to afford 5.6 g of (5S)-5-[(1S)-1-[tert-butyl(diphenyl)silyl]oxypropyl]tetrahydrofuran-2-one (compound 28e-S) and 2 g of (5S)-5-[(1R)-1-[tert-butyl(diphenyl)silyl]oxypropyl]tetrahydrofuran-2-one (compound 28e-R). (Refer to *Tetrahedron.* 1997, 53, 6281-6294).

Compound 28e-S: $^1$H NMR (CDCl$_3$ 400 MHz) δ ppm: 7.73-7.69 (m, 4H), 7.46-7.39 (m, 6H), 4.56 (m, 1H), 3.66 (m, 1H), 2.64-2.47 (m, 2H), 2.20-2.15 (m, 1H), 1.72-1.67 (m, 1H), 1.47-1.42 (m, 1H), 1.15-1.05 (m, 9H), 0.82-0.73 (t, 3H).

Compound 28e-R: $^1$H NMR (CDCl$_3$ 400 MHz) δ ppm: 7.72-7.69 (m, 4H), 7.48-7.39 (m, 6H), 4.54 (m, 1H), 3.92 (m, 1H), 2.60-2.47 (m, 2H), 2.38-2.31 (m, 1H), 2.19-2.12 (m, 1H), 1.50-1.41 (m, 1H), 1.05 (s, 9H), 0.74-0.72 (t, 3H).

Preparation of (3R,5S)-5-[(1S)-1-[tert-butyl(diphenyl)silyl]oxypropyl]-3-methyl-tetrahydrofuran-2-one

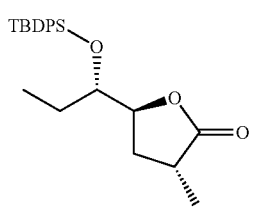

28f

To a solution of (5S)-5-[(1S)-1-[tert-butyl(diphenyl)silyl]oxypropyl]tetrahydrofuran-2-one (Compound 28e-S, 3.0 g, 7.8 mmol) in THF (60 mL) at −78° C. was added lithium diisopropylamide (2M in THF, 5.9 mL, 11.8 mmol) dropwise. After addition, the reaction was stirred at −78° C. for 1 hour. To the mixture was added iodomethane (5.5 g, 39 mmol) and the mixture was stirred at −78° C. for another 1 hour. The mixture was quenched with saturated NH$_4$Cl solution (40 mL), extracted with EtOAc (100 mL) twice. The organic layers were combined, washed with brine (50 mL), dried over Na$_2$SO$_4$ and concentrated in vacuo. The residue was purified by column chromatography on silica gel (eluting with 1:20 to 1:10 EtOAc in petroleum ether) to afford 2.7 g of (3R,5S)-5-[(1S)-1-[tert-butyl(diphenyl)silyl]oxypropyl]-3-methyl-tetrahydrofuran-2-one (compound 28f) as a colourless oil. (Refer to *Tetrahedron.* 1997, 53, 6281-6294).

Preparation of (3R,5S)-5-[(1S)-1-hydroxypropyl]-3-methyl-tetrahydrofuran-2-one

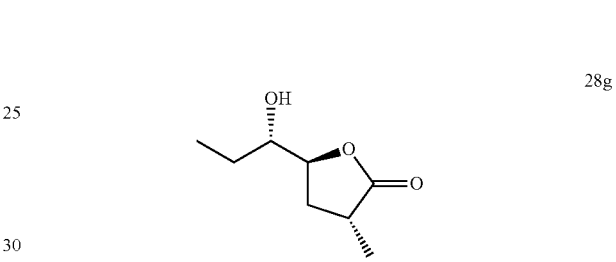

28g

A solution of (3R,5S)-5-[(1S)-1-[tert-butyl(diphenyl)silyl]oxypropyl]-3-methyl-tetrahydrofuran-2-one (compound 28f, 2.7 g, 6.8 mmol) in THF (10 mL) was added TBAF (1M in THF, 13.6 mL, 13.6 mmol) and the mixture was stirred at room temperature for 12 hours. Then the mixture was concentrated in vacuo and the residue was purified by column chromatography on silica gel (eluting with 1:30 to 1:20 EtOAc in petroleum ether) to afford 1.02 g of (3R,5S)-5-[(1S)-1-hydroxypropyl]-3-methyl-tetrahydrofuran-2-one (compound 28g) as a colourless oil.

Preparation of [(1S)-1-[(2S,4R)-4-methyl-5-oxo-tetrahydrofuran-2-yl]propyl] benzoate

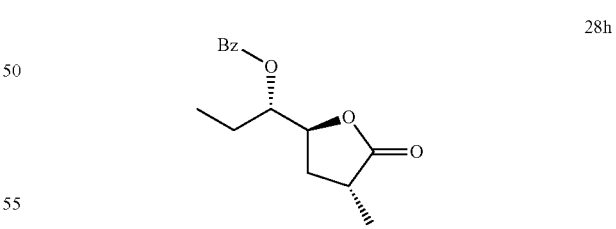

28h

To a solution of (3R,5S)-5-[(1S)-1-hydroxypropyl]-3-methyl-tetrahydrofuran-2-one (compound 28g, 1.0 g, 6.3 mmol), TEA (3.2 g, 31.2 mmol) and DMAP (100 mg) in DCM (50 mL) was added benzoyl chloride (1.8 g, 12.6 mmol) slowly at 0° C. The mixture was stirred at 25° C. for 4 hours and then quenched by saturated NaHCO$_3$ solution, extracted with EtOAc (100 mL) twice. The organic layers were combined, washed with brine (50 mL), dried over Na$_2$SO$_4$ and concentrated in vacuo. The residue was purified by column chromatography on silica gel (eluting with 1:20 to 1:5 EtOAc in petroleum ether) to afford 1.4 g of [(1S)-1-[(2S,4R)-4-methyl-5-oxo-tetrahydrofuran-2-yl]propyl] benzoate (compound 28h) as a colourless oil.

Preparation of [(1S)-1-[(2S,4R)-5-hydroxy-4-methyl-tetrahydrofuran-2-yl]propyl] benzoate

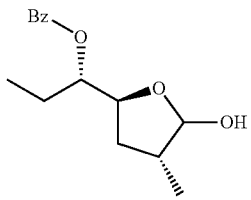

28i

To a solution of [(1S)-1-[(2S,4R)-4-methyl-5-oxo-tetrahydrofuran-2-yl]propyl] benzoate (compound 28h, 1.3 g, 5.0 mmol) in THF (100 mL) was added diisobutyl aluminium hydride (11 mL, 11 mmol) dropwise at −78° C. and the mixture was stirred at −78° C. for 2 hours. The mixture was quenched by saturated NH$_4$Cl solution (5 mL) and extracted with EtOAc (100 mL) twice. The organic layers were combined, washed with brine (50 ml), dried over Na$_2$SO$_4$ and concentrated in vacuo to afford 1.2 g crude product of [(1S)-1-[(2S,4R)-5-hydroxy-4-methyl-tetrahydrofuran-2-yl]propyl] benzoate (compound 28i), which was used in next step without further purification.

Preparation of [(1S)-1-[(2S,4R)-5-acetoxy-4-methyl-tetrahydrofuran-2-yl]propyl] benzoate

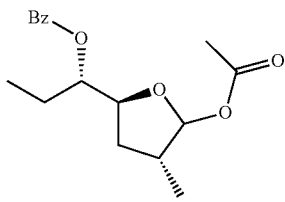

28j

To a solution of [(1S)-1-[(2S,4R)-5-hydroxy-4-methyl-tetrahydrofuran-2-yl]propyl] benzoate (compound 28i, crude, 1.2 g, 4.5 mmol) in pyridine (60 mL) was added acetic acid anhydride (0.918 g, 9 mmol) and DMAP (200 mg) with stirring. After being stirred 25° C. for 2 hours, the mixture was quenched with saturated NaHCO$_3$ solution and extracted with EtOAc (40 mL). The organic layers were combined, washed with brine (50 mL), dried over Na$_2$SO$_4$ and concentrated in vacuo. The residue was purified by column chromatography on silica gel (eluting with 1:20 to 1:5 EtOAc in petroleum ether) to afford 1.0 g of [(1S)-1-[(2S,4R)-5-acetoxy-4-methyl-tetrahydrofuran-2-yl]propyl] benzoate (compound 28j) as a colourless oil.

Preparation of [(1S)-1-[(2S,4R,5R)-5-(5-amino-2,7-dioxo-6H-thiazolo[4,5-d]pyrimidin-3-yl)-4-methyl-tetrahydrofuran-2-yl]propyl] benzoate (compound 28k-A) and [(1R)-1-[(2S,4R,5R)-5-(5-amino-2,7-dioxo-6H-thiazolo[4,5-d]pyrimidin-3-yl)-4-methyl-tetrahydrofuran-2-yl]propyl]benzoate (compound 28k-B)

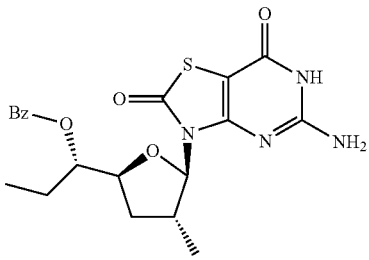

To a suspension of 5-amino-3,6-dihydrothiazolo[4,5-d]pyrimidine-2,7-dione (872 mg, 4.7 mmol) in ACN (20 mL) was added BSA (913.5 mg, 4.5 mmol). The resulting reaction mixture was then stirred at 70° C. under argon for 2 hours to form a clear solution. After the solution was cooled to room temperature, [(1S)-1-[(2S,4R)-5-acetoxy-4-methyl-tetrahydrofuran-2-yl]propyl] benzoate (compound 28j, 294 mg, 0.95 mmol) and TMSOTf (1.44 g, 6.6 mmol) were added in sequence. After being stirred with stirring at 20° C. for 14 hrs, the solvent was removed in vacuo. The residue was partitioned between EtOAc and saturated NaHCO$_3$ solution (30 mL). The organic layer was separated and the aqueous phase was extracted with EtOAc (30 mL) twice. The combined organic layers were washed with brine, dried over Na$_2$SO$_4$ and concentrated in vacuo. The residue was purified and separated by preparative HPLC to afford 9.7 mg of [(1S)-1-[(2S,4R,5R)-5-(5-amino-2,7-dioxo-6H-thiazolo[4,5-d]pyrimidin-3-yl)-4-methyl-tetrahydrofuran-2-yl]propyl] benzoate (compound 28k-A) and 8.4 mg of [(1R)-1-[(2S,4R,5R)-5-(5-amino-2,7-dioxo-6H-thiazolo[4,5-d]pyrimidin-3-yl)-4-methyl-tetrahydrofuran-2-yl]propyl] benzoate (compound 28k-B) as white solid.

Compound 28k-A: $^1$H NMR (400 MHz, CD$_3$OD) δ ppm: 7.97-8.05 (m, 2H), 7.55-7.62 (m, 1H), 7.41-7.48 (m, 2H), 5.77 (d, J=4.14 Hz, 1H), 5.19-5.27 (m, 1H), 4.35 (dt, J=8.38, 6.48 Hz, 1H), 3.16 (dd, J=7.40, 4.27 Hz, 1H), 2.57 (dt, J=12.33, 8.77 Hz, 1H), 1.67-1.87 (m, 3H), 1.16 (d, J=7.28 Hz, 3H), 0.95 (t, J=7.47 Hz, 3H). MS obsd. (ESI$^+$) [(M+H)$^+$]: 431.

Compound 28k-B: $^1$H NMR (400 MHz, CD$_3$OD) δ ppm: 8.03-8.08 (m, 2H), 7.61-7.66 (m, 1H), 7.48-7.55 (m, 2H), 6.41 (d, J=7.65 Hz, 1H), 5.06 (td, J=6.65, 4.27 Hz, 1H), 4.75 (d, J=7.15 Hz, 1H), 2.72-2.84 (m, 1H), 2.25-2.42 (m, 1H), 1.97-2.06 (m, 1H), 1.75-1.85 (m, 2H), 0.97 (t, J=7.40 Hz, 3H), 0.89 (d, J=6.90 Hz, 3H). MS obsd. (ESI+) [(M+H)+]: 431.

Preparation of 5-amino-3-[(2R,3R,5S)-5-[(1S)-1-hydroxypropyl]-3-methyl-tetrahydrofuran-2-yl]-6H-thiazolo[4,5-d]pyrimidine-2,7-dione

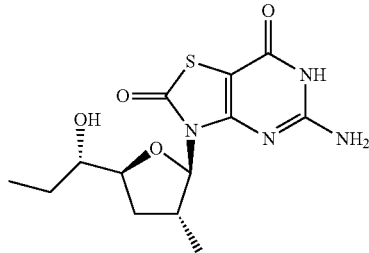

28

To a solution of compound [(1S)-1-[(2S,4R,5R)-5-(5-amino-2,7-dioxo-6H-thiazolo[4,5-d]pyrimidin-3-yl)-4-methyl-tetrahydrofuran-2-yl]propyl] benzoate (compound 28k-A, 120 mg, 0.27 mmol) in MeOH (2 mL) was added K₂CO₃ (58 mg, 0.42 mmol). After being stirred at room temperature for 5 hours, the reaction mixture was adjusted to pH 7 by bubbling CO₂ and then concentrated in vacuo. The residue was purified by preparative HPLC to afford 24 mg of 5-amino-3-[(2R,3R,5S)-5-[(1S)-1-hydroxypropyl]-3-methyl-tetrahydrofuran-2-yl]-6H-thiazolo[4,5-d]pyrimidine-2,7-dione (Example 28) as a white solid.

Example 28: ¹H NMR (400 MHz, CD₃OD) δ ppm: 5.81 (d, J=7.03 Hz, 1H), 4.03-4.18 (m, 1H), 3.45-3.48 (m, 1H), 3.05-3.11 (m, 1H), 2.37-2.42 (m, 1H), 1.80-1.85 (m, 1H), 1.40-1.62 (m, 2H), 1.11 (d, J=6.78 Hz, 3H), 1.00 (t, J=7.40 Hz, 3H). MS obsd. (ESI+) [(M+H)+]: 327.

Example 29

5-Amino-3-[(2R,3R,5S)-5-[(1S)-1-hydroxybut-2-yl]-3-methyl-tetrahydrofuran-2-yl]-6H-thiazolo[4,5-d]pyrimidine-2,7-dione

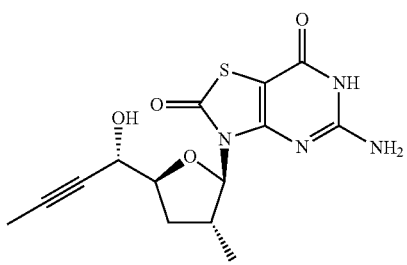

29

The title compound was prepared in analogy to Example 28 by using 1-propynyl magnesium bromide instead of ethyl magnesium bromide. After being purified by preparative HPLC, 5-amino-3-[(2R,3R,5S)-5-[(1S)-1-hydroxybut-2-yl]-3-methyl-tetrahydrofuran-2-yl]-6H-thiazolo[4,5-d]pyrimidine-2,7-dione (Example 29) was afforded as a white solid.

Example 29: ¹H NMR (400 MHz, CD₃OD) δ ppm: 5.83-5.85 (m, 1H), 4.74-4.78 (m, 1H), 4.42-4.44 (m, 1H), 4.12-4.13 (m, 1H), 3.15-3.17 (m, 1H), 1.87-1.89 (m, 1H), 1.83-1.84 (m, 3H), 1.10-1.12 (m, 3H). MS obsd. (ESI+) [(M+H)+]: 337.

Example 30

5-Amino-3-[(2R,3R,5S)-5-[(S)-cyclopropyl(hydroxy)methyl]-3-methyl-tetrahydrofuran-2-yl]-6H-thiazolo[4,5-d]pyrimidine-2,7-dione

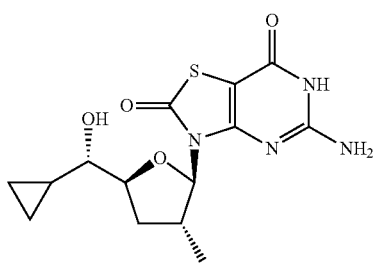

30

The title compound was prepared in analogy to Example 28 by using cyclopropyl magnesium bromide instead of ethyl magnesium bromide. After being purified by preparative HPLC, 5-amino-3-[(2R,3R,5S)-5-[(S)-cyclopropyl(hydroxy)methyl]-3-methyl-tetrahydrofuran-2-yl]-6H-thiazolo[4,5-d]pyrimidine-2,7-dione (Example 30) was afforded as a white solid.

Example 30: ¹H NMR (400 MHz, CD₃OD) δ ppm: 5.82 (d, J=6.78 Hz, 1H), 4.20 (dt, J=7.87, 5.22 Hz, 1H), 3.05 (d, J=7.78 Hz, 1H), 2.92 (dd, J=8.34, 4.58 Hz, 1H), 2.38-2.47 (m, 1H), 1.83 (dt, J=12.39, 7.73 Hz, 1H), 1.10 (d, J=6.90 Hz, 3H), 0.87-0.98 (m, 1H), 0.46-0.52 (m, 2H), 0.26-0.39 (m, 2H). MS obsd. (ESI+) [(M+H)+]: 339.

Example 31

5-Amino-3-[(2R,3R,5S)-5-[(1S)-1-hydroxyethyl]-3-methyl-tetrahydrofuran-2-yl]-6H-thiazolo[4,5-d]pyrimidine-2,7-dione

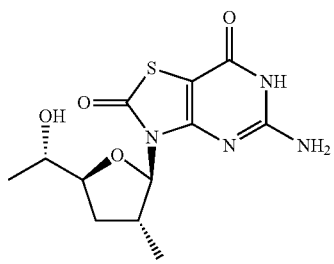

31

The title compound was prepared in analogy to Example 29 by using methyl magnesium bromide instead of ethyl magnesium bromide. After being purified by preparative HPLC, 5-amino-3-[(2R,3R,5S)-5-[(1S)-1-hydroxyethyl]-3-methyl-tetrahydrofuran-2-yl]-6H-thiazolo[4,5-d]pyrimidine-2,7-dione (Example 31) was afforded as a white solid.

Example 31: ¹H NMR (400 MHz, CD₃OD) δ ppm: 5.81 (d, J=6.52 Hz, 1H), 3.90-4.06 (m, 1H), 3.74-3.86 (m, 1H), 2.97-3.16 (m, 1H), 2.25-2.41 (m, 1H), 1.68-1.83 (m, 1H), 1.15 (d, J=6.40 Hz, 3H), 1.10 (d, J=6.90 Hz, 3H). MS obsd. (ESI⁺) [(M+H)⁺]: 313.

Example 32

5-Amino-3-[(2R,3R,5S)-5-(hydroxymethyl)-3-pyrrolidin-1-yl-tetrahydrofuran-2-yl]-6H-thiazolo[4,5-d]pyrimidine-2,7-dione The title compound was prepared according to the following scheme:

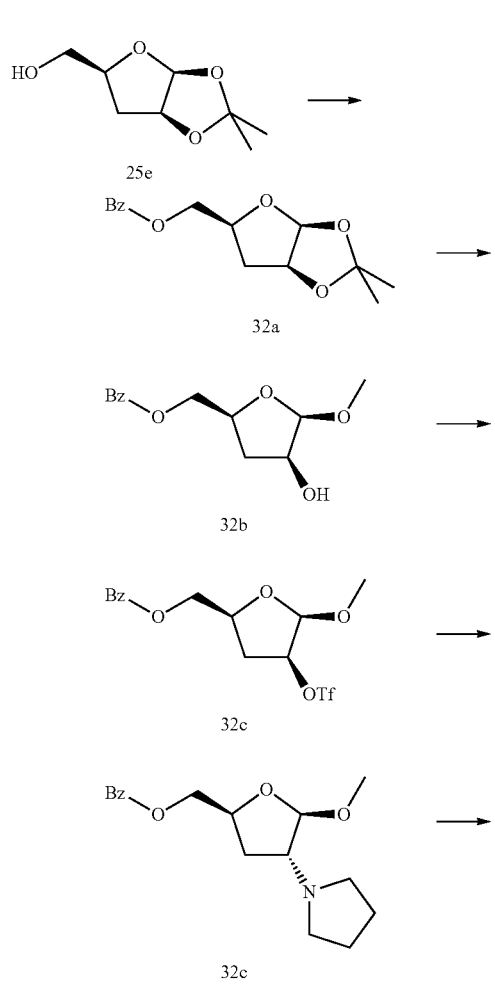

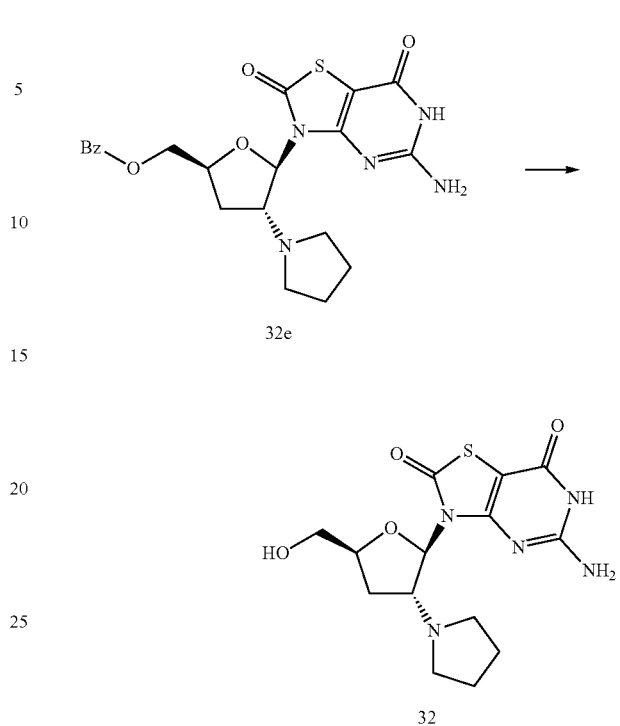

Preparation of [(3aS,5S,6aS)-2,2-dimethyl-3a,5,6,6a-tetrahydrofuro[2,3-d][1,3]dioxol-5-yl]methyl benzoate

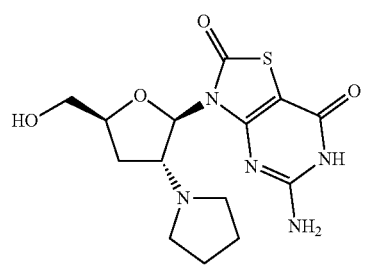

To a cooled solution of crude [(3aS,5S,6aS)-2,2-dimethyl-3a,5,6,6a-tetrahydrofuro[2,3-d][1,3]dioxol-5-yl]methanol (compound 25e, 7.6 g, 43.6 mmol) and TEA (8.6 g, 109 mmol) in DCM was added benzoyl chloride (9.1 g, 65.5 mmol) dropwise at 0° C. with stirring. After the addition, the mixture was warmed naturally to room temperature and stirred at room temperature overnight. The resulting mixture was washed with 1N hydrochloric acid, brine, dried over Na₂SO₄ and concentrated in vacuo. The residue was purified by column chromatography on silica gel (eluting with 0-30% EtOAc in petroleum ether) to afford 5.8 g of 1-[(3aR,5S,6aR)-2,2-dimethyl-3a,5,6,6a-tetrahydrofuro[2,3-d][1,3]dioxol-5-yl]propyl benzoate (compound 32a).

Compound 32a: ¹H NMR (400 MHz, CDCl₃) δ ppm: 8.06-8.16 (m, 2H), 7.54-7.62 (m, 1H), 7.42-7.52 (m, 2H), 5.88 (d, J=3.76 Hz, 1H), 4.81 (d, J=1.00 Hz, 1H), 4.51-4.65 (m, 2H), 4.46 (dd, J=4.64, 10.16 Hz, 1H), 2.27-2.34 (m, 1H), 2.19 (s, 1H), 1.63 (s, 3H), 1.36 (s, 3H).

Preparation of [(2S,4S)-4-hydroxy-5-methoxy-tetrahydrofuran-2-yl]methyl benzoate

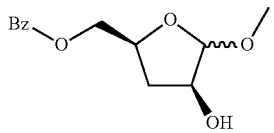

32b

To a solution of [(3aS,5S,6aS)-2,2-dimethyl-3a,5,6,6a-tetrahydrofuro[2,3-d][1,3]dioxol-5-yl]methyl benzoate (compound 32a, 5.1 g, 18 mmol) in MeOH (50 mL) was added H$_2$SO$_4$ (0.5 mL) at room temperature. After being stirred at 80° C. for 0.5 hour, the reaction mixture was cooled to room temperature, neutralized by solid NaHCO$_3$ and concentrated in vacuo. The residue was re-dissolved in EtOAc, washed with water twice. The separated organic layer was dried over Na$_2$SO$_4$ and concentrated in vacuo to afford 4.1 g crude product of [(2S,4S)-4-hydroxy-5-methoxy-tetrahydrofuran-2-yl]methyl benzoate (compound 32b) as oil, which was used in next step directly. MS obsd. (ESI$^+$) [(M+NH$_4$)$^+$]: 270.

Preparation of [(2S,4S)-5-methoxy-4-(trifluoromethylsulfonyloxy)tetrahydrofuran-2-yl]methyl benzoate

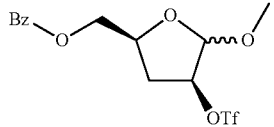

32c

To a solution of [(2S,4S)-4-hydroxy-5-methoxy-tetrahydrofuran-2-yl]methyl benzoate (compound 32b, 4.1 g, 17 mmol), pyridine (4.8 g, 60 mmol) and DMAP (300 mg, 2.5 mmol) in DCM (50 mL) was added trifluoromethanesulfonic anhydride (8.5 g, 30 mmol) at –30° C. After being stirred at –30° C.-0° C. for 2 hours, the reaction was quenched by saturated NaHCO$_3$ solution and extracted with DCM three times. The combined organic layers were dried over Na$_2$SO$_4$ and concentrated to afford 6.6 g crude product of [(2S,4S)-5-methoxy-4-(trifluoromethylsulfonyloxy)tetrahydrofuran-2-yl]methyl benzoate (compound 32c) as an oil, which was used in next step without further purification. MS obsd. (ESI$^+$) [(M+H)$^+$]: 385.

Preparation of [(2S,4R)-5-methoxy-4-pyrrolidin-1-yl-tetrahydrofuran-2-yl]methyl benzoate

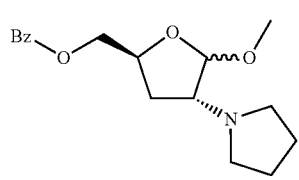

32d

To a solution of [(2S,4S)-5-methoxy-4-(trifluoromethylsulfonyloxy)tetrahydrofuran-2-yl]methyl benzoate (compound 32c, 400 mg, 1.04 mmol) in DMF (3 mL) was added pyrrolidine (142 mg, 2.0 mmol) at room temperature and the mixture was stirred at room temperature for 16 hours. The reaction mixture was diluted by water and extracted with EtOAc, the organic layers were combined and concentrated in vacuo to afford 230 mg crude product of [(2S,4R)-5-methoxy-4-pyrrolidin-1-yl-tetrahydrofuran-2-yl]methyl benzoate (compound 32d) as an oil, which was used in next step without further purification. MS obsd. (ESP) [(M+H)$^+$]: 306.

Preparation of [(2S,4R,5R)-5-(5-amino-2,7-dioxo-6H-thiazolo[4,5-d]pyrimidin-3-yl)-4-pyrrolidin-1-yl-tetrahydrofuran-2-yl]methyl benzoate

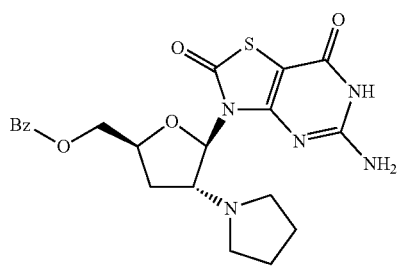

32e

To a suspension of 5-amino-3,6-dihydrothiazolo[4,5-d]pyrimidine-2,7-dione (138 mg, 0.75 mmol) in ACN (5 mL) was added BSA (535 mg, 2.6 mmol). The resulting reaction mixture was then stirred at 70° C. under argon for 0.5 hour to form a clear solution. After the solution was cooled to room temperature, [(2S,4R)-5-methoxy-4-pyrrolidin-1-yl-tetrahydrofuran-2-yl]methyl benzoate (compound 32d, 230 mg, 0.75 mmol) and TMSOTf (832 mg, 3.75 mmol) were added in sequence. After being heated with stirring at 70° C. for 14 hours, the solvent was removed in vacuo. The residue was partitioned between EtOAc and saturated NaHCO$_3$ solution (30 mL). The organic layer was separated and the aqueous phase was extracted with EtOAc (30 mL) twice. The combined organic layers were washed with brine, dried over Na$_2$SO$_4$ and concentrated in vacuo to afford 250 mg crude product of [(2S,4R,5R)-5-(5-amino-2,7-dioxo-6H-thiazolo[4,5-d]pyrimidin-3-yl)-4-pyrrolidin-1-yl-tetrahydrofuran-2-yl]methyl benzoate (compound 32e) as a yellow solid. MS obsd. (ESI$^+$) [(M+H)$^+$]: 458.

Preparation of 5-amino-3-[(2R,3R,5S)-5-(hydroxymethyl)-3-pyrrolidin-1-yl-tetrahydrofuran-2-yl]-6H-thiazolo[4,5-d]pyrimidine-2,7-dione

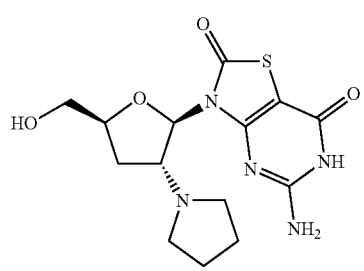

32

To a solution of compound [(2S,4R,5R)-5-(5-amino-2,7-dioxo-6H-thiazolo[4,5-d]pyrimidin-3-yl)-4-pyrrolidin-1-yl-tetrahydrofuran-2-yl]methyl benzoate (compound 32e, 250 mg, 0.54 mmol) in MeOH (8 mL) was added K$_2$CO$_3$ (138 mg, 1.0 mmol). After being stirred at room temperature for 5 hours, the reaction mixture was concentrated in vacuo and the residue was purified by preparative HPLC to afford 10.0 mg of 5-amino-3-[(2R,3R,5S)-5-(hydroxymethyl)-3-pyrrolidin-1-yl-tetrahydrofuran-2-yl]-6H-thiazolo[4,5-d]pyrimidine-2,7-dione (Example 32) as a white solid.

Example 32: $^1$H NMR (400 MHz, CD$_3$OD) δ ppm: 6.08 (d, J=6.8 Hz, 1H), 4.30-4.37 (m, 1H), 3.78-3.89 (m, 2H), 3.54-3.61 (m, 1H), 2.57-2.64 (m, 2H), 2.50-2.56 (m, 2H), 2.42-2.49 (m, 1H), 2.20-2.30 (m, 1H), 1.79 (m, 4H). MS obsd. (ESI) [(M+H)$^+$]: 354.

Example 33

N-[(2R,3R,5S)-2-(5-amino-2,7-dioxo-6H-thiazolo[4,5-d]pyrimidin-3-yl)-5-(hydroxymethyl)tetrahydrofuran-3-yl]methanesulfonamide

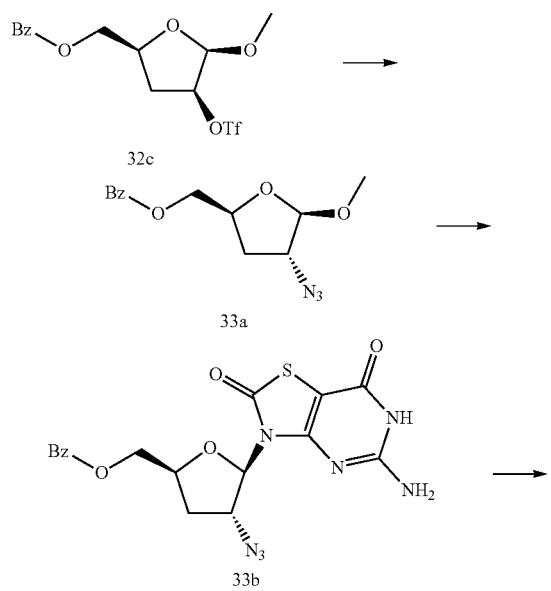

The title compound was prepared according to the following scheme:

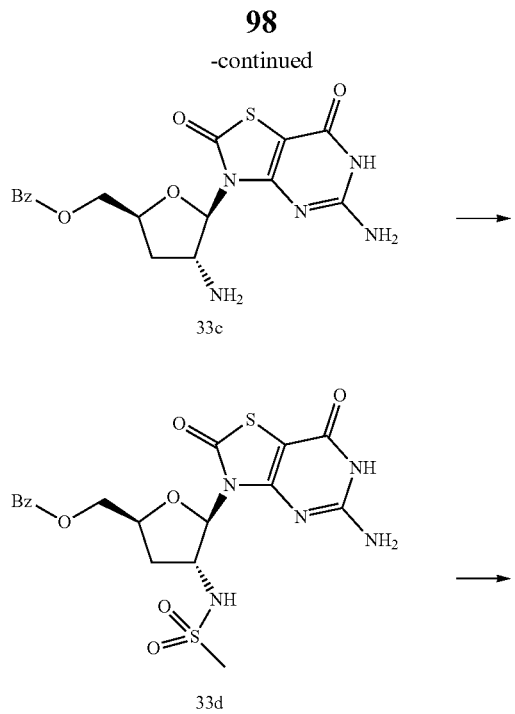

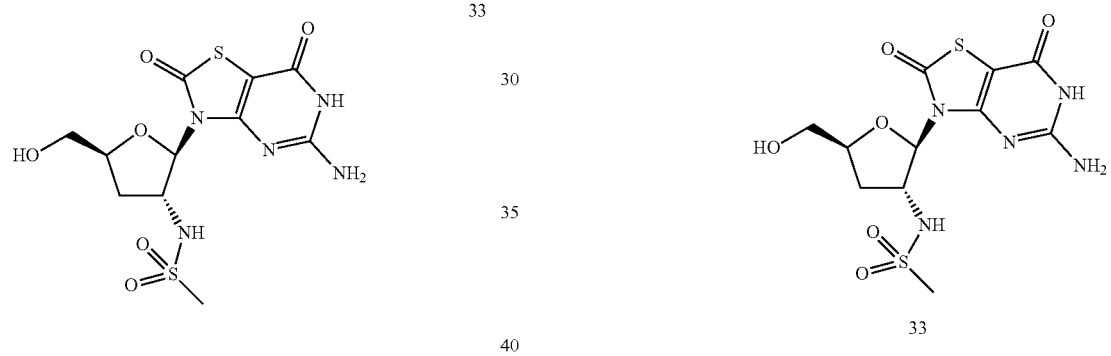

Preparation of [(2S,4R,5R)-4-azido-5-methoxy-tetrahydrofuran-2-yl]methyl benzoate

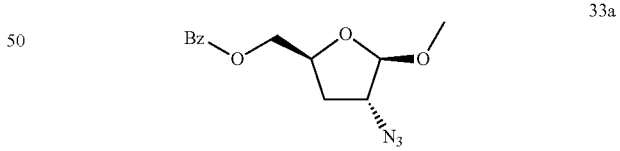

To a solution of [(2S,4S)-5-methoxy-4-(trifluoromethylsulfonyloxy)tetrahydrofuran-2-yl]methyl benzoate (compound 32c, 1.1 g, 2.8 mmol) in DMF (5 mL) was added sodium azide (372 mg, 5.7 mmol) at room temperature and the mixture was stirred at room temperature for 16 hours. The reaction mixture was diluted with water and extracted with EtOAc, the organic layers were combined and concentrated in vacuo to afford 1.1 g crude product of [(2S,4R,5R)-4-azido-5-methoxy-tetrahydrofuran-2-yl]methyl benzoate (compound 33a) as an oil, which was used in next step without further purification.

Preparation of [(2S,4R,5R)-5-(5-amino-2,7-dioxo-6H-thiazolo[4,5-d]pyrimidin-3-yl)-4-azido-tetrahydrofuran-2-yl]methyl benzoate

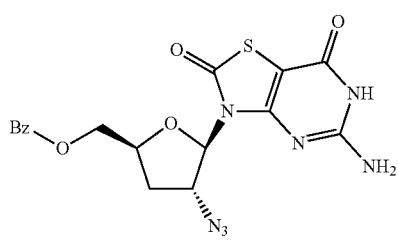

33b

To a suspension of 5-amino-3,6-dihydrothiazolo[4,5-d]pyrimidine-2,7-dione (730 mg, 3.97 mmol) in ACN (15 mL) was added BSA (2.8 mg, 13.8 mmol). The resulting reaction mixture was then stirred at 70° C. under argon for 0.5 hour to form a clear solution. After the solution was cooled to room temperature, [(2S,4R,5R)-4-azido-5-methoxy-tetrahydrofuran-2-yl]methyl benzoate (compound 33a, crude, 1.1 g, 3.97 mmol) and TMSOTf (4.4 g, 19.5 mmol) were added in sequence. After being heated with stirring at 70° C. for 14 hours, the solvent was removed in vacuo. The residue was partitioned between EtOAc and saturated NaHCO₃ solution (30 mL). The organic layer was separated and the aqueous phase was extracted with EtOAc (30 mL) twice. The combined organic layers were washed with brine, dried over Na₂SO₄ and concentrated in vacuo to afford 500 mg crude product of [(2S,4R,5R)-5-(5-amino-2,7-dioxo-6H-thiazolo[4,5-d]pyrimidin-3-yl)-4-azido-tetrahydrofuran-2-yl]methyl benzoate (compound 33b) as a yellow solid. MS obsd. (ESI⁺) [(M+H)⁺]: 430.

Preparation of [(2S,4R,5R)-4-amino-5-(5-amino-2,7-dioxo-6H-thiazolo[4,5-d]pyrimidin-3-yl)tetrahydrofuran-2-yl]methyl benzoate

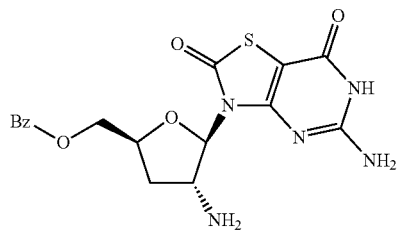

33c

To a solution of compound [(2S,4R,5R)-5-(5-amino-2,7-dioxo-6H-thiazolo[4,5-d]pyrimidin-3-yl)-4-azido-tetrahydrofuran-2-yl]methyl benzoate (compound 33b, 200 mg, 0.466 mmoL) and triphenylphosphine (364 mg, 1.39 mmoL) in THF (10 mL) was added water (0.5 mL) at room temperature. After being stirred at 80° C. for 1 hour, the reaction was filtered and the filtrate was concentrated in vacuo to afford 80 mg crude product of [(2S,4R,5R)-4-amino-5-(5-amino-2,7-dioxo-6H-thiazolo[4,5-d]pyrimidin-3-yl)tetrahydrofuran-2-yl]methyl benzoate (compound 33c), which was used in next step directly. MS obsd. (ESI⁺) [(M+H)⁺]: 404.

Preparation of [(2S,4R,5R)-5-(5-amino-2,7-dioxo-6H-thiazolo[4,5-d]pyrimidin-3-yl)-4-(methanesulfonamido)tetrahydrofuran-2-yl]methyl benzoate

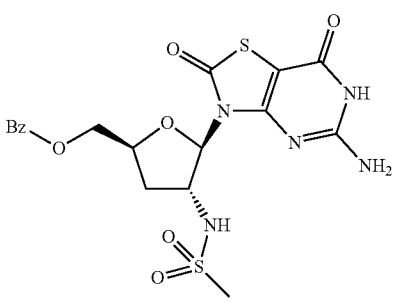

33d

To a solution of compound [(2S,4R,5R)-4-amino-5-(5-amino-2,7-dioxo-6H-thiazolo[4,5-d]pyrimidin-3-yl)tetrahydrofuran-2-yl]methyl benzoate (compound 33c, crude, 80 mg, 0.198 mmoL) in DCM (10 mL) and THF (2 mL) were added TEA (44 mg, 0.436 mmoL) and methanesulfonyl chloride (27 mg, 0.237 mmol) at 0° C. After being stirred at room temperature for 2 hours, the reaction mixture was diluted by DCM, washed with water, brine, dried over Na₂SO₄ and concentrated in vacuo to afford 80 mg crude product of [(2S,4R,5R)-5-(5-amino-2,7-dioxo-6H-thiazolo[4,5-d]pyrimidin-3-yl)-4-(methanesulfonamido)tetrahydrofuran-2-yl]methyl benzoate (compound 33d), which was used in next step directly. MS obsd. (ESI⁻) [(M−H)⁺]: 480.

Preparation of N-[(2R,3R,5S)-2-(5-amino-2,7-dioxo-6H-thiazolo[4,5-d]pyrimidin-3-yl)-5-(hydroxymethyl)tetrahydrofuran-3-yl]methanesulfonamide

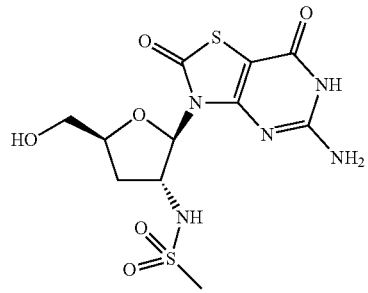

33

To a solution of [(2S,4R,5R)-5-(5-amino-2,7-dioxo-6H-thiazolo[4,5-d]pyrimidin-3-yl)-4-(methanesulfonamido)tetrahydrofuran-2-yl]methyl benzoate (compound 33d, crude, 80 mg, 0.54 mmol) in MeOH (5 mL) was added K₂CO₃ (80 mg, 0.6 mmol). After being stirred at room temperature for 5 hours, the reaction mixture was concentrated in vacuo and the residue was purified by preparative HPLC to afford 8.0 mg of N-[(2R,3R,5S)-2-(5-amino-2,7-dioxo-6H-thiazolo[4,5-d]pyrimidin-3-yl)-5-(hydroxymethyl)tetrahydrofuran-3-yl]methanesulfonamide (Example 33) as a white solid.

Example 33: 8 mg, ¹H NMR (400 MHz, d₆-DMSO) δ ppm: 11.45-11.78 (br. s., 1H), 7.82 (d, J=8.5 Hz, 1H), 6.99 (br. s., 2H), 5.79 (d, J=4.8 Hz, 1H), 4.68-4.84 (m, 2H), 4.15

(dt, J=12.7, 6.3 Hz, 1H), 3.46 (m, 2H), 2.89 (s, 3H), 2.37-2.44 (m, 1H), 1.90-2.00 (m, 1H). MS obsd. (ESI⁺) [(M+H)⁺]: 378.

Example 34

N-[(2R,3R,5S)-2-(5-amino-2,7-dioxo-6H-thiazolo[4,5-d]pyrimidin-3-yl)-5-(hydroxymethyl)tetrahydrofuran-3-yl]acetamide

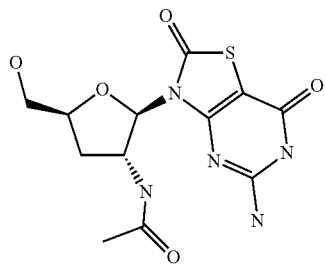

34

The title compound was prepared in analogy to Example 33 by using acyl chloride instead of methylsulfonyl chloride. After being purified by preparative HPLC, N-[(2R,3R,5S)-2-(5-amino-2,7-dioxo-6H-thiazolo[4,5-d]pyrimidin-3-yl)-5-(hydroxymethyl)tetrahydrofuran-3-yl]acetamide (Example 34) was afforded as a white solid.

Example 34: ¹H NMR (400 MHz, d₆-DMSO) δ ppm: 6.09 (dd, J=9.0, 5.8 Hz, 1H), 5.08 (t, J=5.6 Hz, 1H), 3.92-4.01 (m, 1H), 3.66 (dd, J=11.4, 6.1 Hz, 1H), 3.50-3.53 (m, 1H), 3.10-3.23 (m, 2H), 1.56-1.61 (m, 1H), 1.23-1.38 (m, 1H), 0.93 (t, J=7.3 Hz, 1H). MS obsd. (ESI⁺) [(M+H)⁺]: 342.

Example 35

5-Amino-3-[(2R,3R,5S)-5-(hydroxymethyl)-3-morpholino-tetrahydrofuran-2-yl]-6H-thiazolo[4,5-d]pyrimidine-2,7-dione

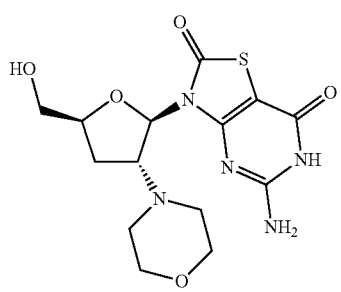

35

The title compound was prepared in analogy to Example 32 by using morpholine instead of pyrrolidine. After being purified by preparative HPLC, 5-amino-3-[(2R,3R,5S)-5-(hydroxymethyl)-3-morpholino-tetrahydrofuran-2-yl]-6H-thiazolo[4,5-d]pyrimidine-2,7-dione (Example 35) was afforded as a white solid.

Example 35: ¹H NMR (400 MHz, CD₃OD) δ ppm: 6.17 (d, J=5.3 Hz, 1H), 4.26 (tt, J=7.5, 4.8 Hz, 1H), 3.88-3.97 (m, 1H), 3.65-3.75 (m, 6H), 2.52-2.64 (m, 4H), 2.37 (ddd, J=13.2, 8.8, 7.4 Hz, 1H), 2.21 (ddd, J=13.1, 7.8, 5.0 Hz, 1H). MS obsd. (ESI⁺) [(M+H)⁺]: 370.

Example 36

5-Amino-3-[(2R,3R,5S)-5-(hydroxymethyl)-3-(1-piperidyl)tetrahydrofuran-2-yl]-6H-thiazolo[4,5-d]pyrimidine-2,7-dione

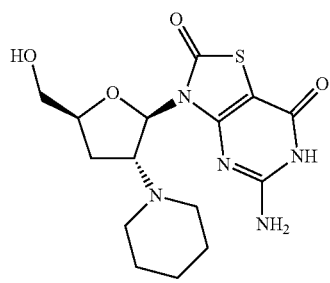

36

The title compound was prepared in analogy to Example 32 by using piperidine instead of pyrrolidine. After being purified by preparative HPLC, 5-amino-3-[(2R,3R,5S)-5-(hydroxymethyl)-3-(1-piperidyl)tetrahydrofuran-2-yl]-6H-thiazolo[4,5-d]pyrimidine-2,7-dione (Example 36) was afforded as a white solid.

Example 36: ¹H NMR (400 MHz, CD₃OD) δ ppm: 6.16 (d, J=6.0 Hz, 1H), 4.28 (d, J=2.8 Hz, 1H), 4.01 (t, J=4.8 Hz, 1H), 3.74 (dd, J=3.6, 11.6 Hz, 1H), 3.63 (dd, J=4.8, 12.0 Hz, 1H), 2.54-2.21 (m, 6H), 1.63-1.48 (m, 6H). MS obsd. (ESI⁺) [(M+H)⁺]: 368.

Example 37

5-Amino-3-[(2R,3R,5S)-3-(dimethylamino)-5-(hydroxymethyl)tetrahydrofuran-2-yl]-6H-thiazolo[4,5-d]pyrimidine-2,7-dione

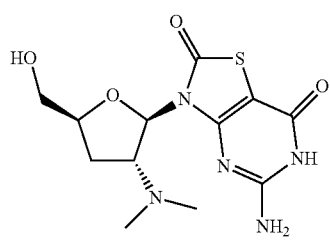

37

The title compound was prepared in analogy to Example 32 by using dimethylamine instead of pyrrolidine. After being purified by preparative HPLC, 5-amino-3-[(2R,3R,5S)-3-(dimethylamino)-5-(hydroxymethyl)tetrahydrofuran-2-yl]-6H-thiazolo[4,5-d]pyrimidine-2,7-dione (Example 37) was afforded as a white solid.

Example 37: ¹H NMR (400 MHz, CD₃OD) δ ppm: 6.08 (d, J=6.52 Hz, 1H), 4.26-4.32 (m, 1H), 3.87-3.95 (m, 1H), 3.77 (dd, J=11.92, 2.89 Hz, 1H), 3.57 (dd, J=11.92, 3.64 Hz, 1H), 2.41 (ddd, J=13.11, 8.47, 5.02 Hz, 1H), 2.27 (s, 6H), 2.19 (ddd, J=12.89, 8.63, 7.59 Hz, 1H). MS obsd. (ESI⁺) [(M+H)⁺]: 328.

Example 38
(2R,3S,5S)-2-(5-amino-2,7-dioxo-6H-thiazolo[4,5-d]pyrimidin-3-yl)-5-(hydroxymethyl)tetrahydrofuran-3-carbonitrile
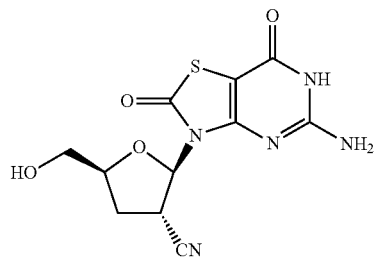
The title compound was prepared according to the following scheme:
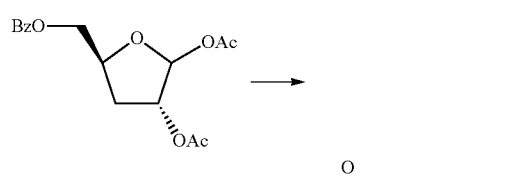
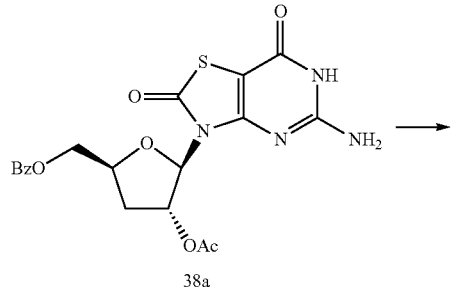
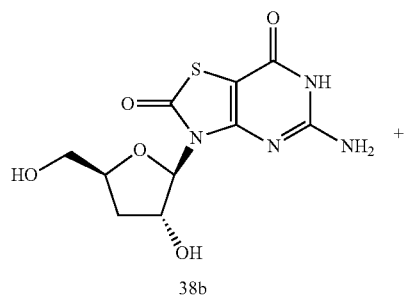
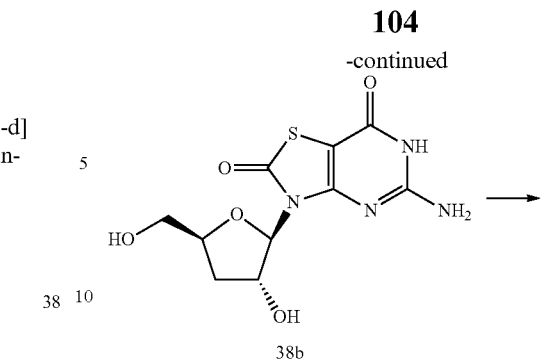
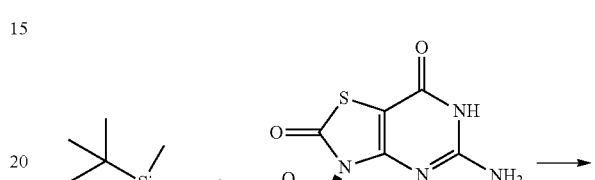
38d
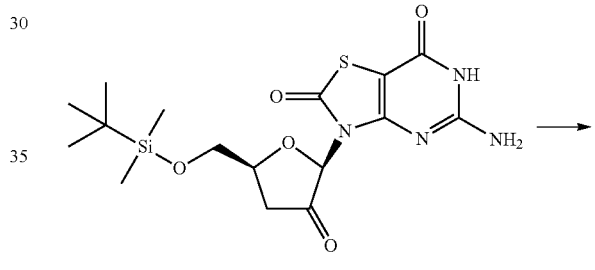
38e
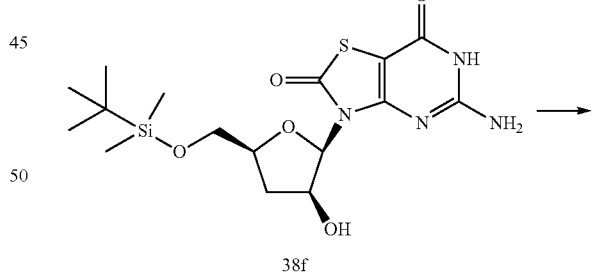
38f
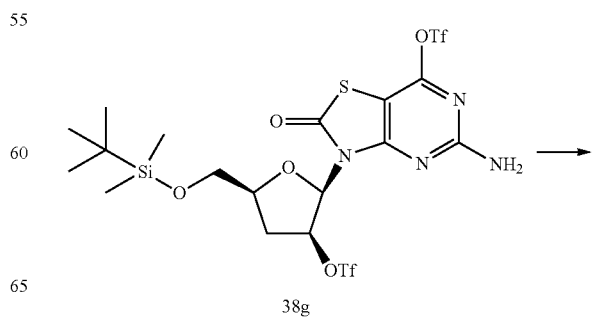
38g -continued

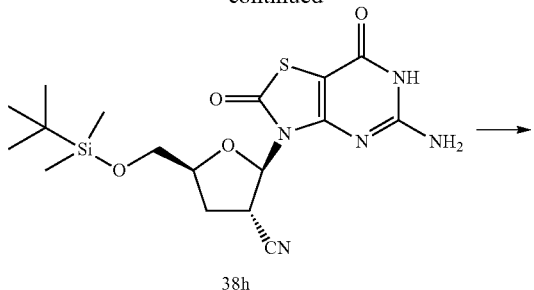

38h

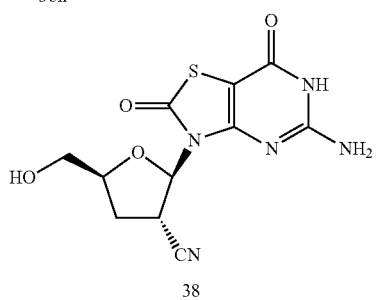

38

Preparation of [(2S,4R,5R)-4-acetoxy-5-(5-amino-2, 7-dioxo-6H-thiazolo[4,5-d]pyrimidin-3-yl)tetrahydrofuran-2-yl]methyl benzoate

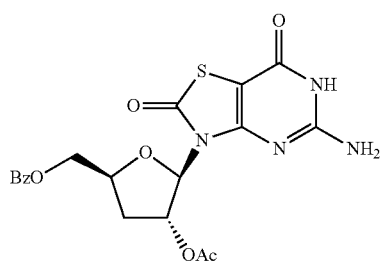

38a

To a suspension of 5-amino-3,6-dihydrothiazolo[4,5-d]pyrimidine-2,7-dione (4.42 g, 24.0 mmol) in ACN (20 mL) was added BSA (14.8 mL, 60.0 mmol). The resulting reaction mixture was then stirred at 70° C. under argon for 0.5 hr to form a clear solution. After the solution was cooled to room temperature, [(2S,4R)-4,5-diacetoxytetrahydrofuran-2-yl]methyl benzoate (CAS #: 4613-71-2, Cat.#: MD04725, commercially available from Carbosynth Limited, 6.45 g, 20.0 mmol) and TMSOTf (5.5 mL, 30.0 mmol) were added in sequence. After being heated with stirring at 70° C. for 14 hours, the solvent was removed in vacuo. The residue was partitioned between EtOAc and saturated NaHCO₃ solution (30 mL). The organic layer was separated and the aqueous phase was extracted with EtOAc (100 mL) twice. The combined organic layers were washed with brine, dried over Na₂SO₄ and concentrated in vacuo. The residue was purified by column chromatography on silica gel to afford 5.7 g of [(2S,4R,5R)-4-acetoxy-5-(5-amino-2,7-dioxo-6H-thiazolo[4,5-d]pyrimidin-3-yl)tetrahydrofuran-2-yl]methyl benzoate (compound 38a) as a light yellow solid.

Preparation of 5-amino-3-[(2R,3R,5S)-3-hydroxy-5-(hydroxymethyl)tetrahydrofuran-2-yl]-6H-thiazolo[4,5-d]pyrimidine-2,7-dione (compound 38b) and [(2S,4R,5R)-5-(5-amino-2,7-dioxo-6H-thiazolo[4,5-d]pyrimidin-3-yl)-4-hydroxy-tetrahydrofuran-2-yl] methyl benzoate (compound 38c)

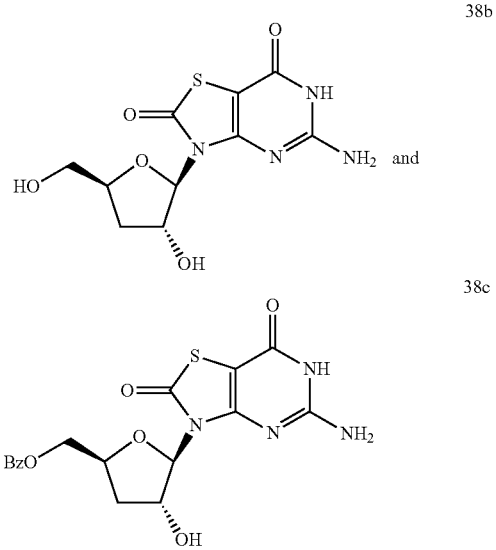

A mixture of [(2S,4R,5R)-4-acetoxy-5-(5-amino-2,7-dioxo-6H-thiazolo[4,5-d]pyrimidin-3-yl)tetrahydrofuran-2-yl]methyl benzoate (compound 38a, 4.72 g, 10.6 mmol) and potassium carbonate (1.46 g, 10.6 mmol) in methanol (106 mL) was stirred at room temperature for 3.5 hours. The reaction was quenched by addition of acetic acid (1.5 mL). The resulting mixture was concentrated in vacuo to remove the solvent and the residue was purified by column chromatography on silica gel (eluting with 0-5% methanol in DCM) to afford 1.0 g of 5-amino-3-[(2R,3R,5S)-3-hydroxy-5-(hydroxymethyl)tetrahydrofuran-2-yl]-6H-thiazolo[4,5-d]pyrimidine-2,7-dione (compound 38b) and 2.8 g of [(2S,4R,5R)-5-(5-amino-2,7-dioxo-6H-thiazolo[4,5-d]pyrimidin-3-yl)-4-hydroxy-tetrahydrofuran-2-yl]methyl benzoate (compound 38c) as a pale solid.

Preparation of 5-amino-3-[(2R,3R,5S)-5-[[tert-butyl (dimethyl)silyl]oxymethyl]-3-hydroxy-tetrahydrofuran-2-yl]-6H-thiazolo[4,5-d]pyrimidine-2,7-dione

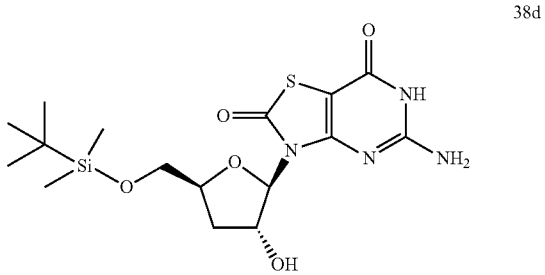 [SMILES: CC(C)(C)[Si](C)(C)OC[C@@H]1C[C@@H](O)[C@H](n2c(=O)sc3c(=O)[nH]c(N)nc32)O1]

38d

To a solution of 5-amino-3-[(2R,3R,5S)-3-hydroxy-5-(hydroxymethyl)tetrahydrofuran-2-yl]-6H-thiazolo[4,5-d]

pyrimidine-2,7-dione (compound 38b, 3.8 g, 12.7 mmol) in DMF (30 mL) was added imidazole (2.6 g, 38 mmol) and tert-butylchlorodimethylsilane (4.2 g, 28 mmol) with stirring. After being stirred at room temperature for 2 hours, the resulting solution was diluted by EtOAc (200 mL), washed with water, brine, dried over $Na_2SO_4$. The organic layer was concentrated in vacuo and the residue was purified by column chromatography on silica gel (eluting with 1:5 EtOAc in petroleum ether) to afford 3.3 g of 5-amino-3-[(2R,3R,5S)-5-[[tert-butyl(dimethyl)silyl]oxymethyl]-3-hydroxy-tetrahydrofuran-2-yl]-6H-thiazolo[4,5-d]pyrimidine-2,7-dione (compound 38d).

Compound 38d: $^1$H NMR (400 MHz, $CDCl_3$) δ ppm: 11.21 (s, 1H), 6.94 (br. s., 2H), 5.70-5.80 (m, 1H), 5.44 (d, J=4.5 Hz, 1H), 4.79 (ddt, J=6.6, 4.4, 2.2 Hz, 1H), 4.11-4.24 (m, 1H), 3.58-3.70 (m, 2H), 2.32 (ddd, J=12.7, 9.4, 6.8 Hz, 1H), 1.80 (ddd, J=12.7, 6.1, 2.0 Hz, 1H), 0.79-0.92 (s, 9H), 0 (s, 6H).

Preparation of 5-amino-3-[(2R,5S)-5-[[tert-butyl(dimethyl)silyl]oxymethyl]-3-oxo-tetrahydrofuran-2-yl]-6H-thiazolo[4,5-d]pyrimidine-2,7-dione

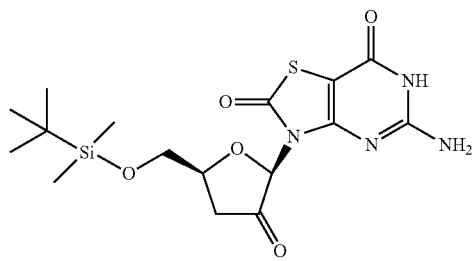

38e

To a solution of 5-amino-3-[(2R,3R,5S)-5-[[tert-butyl(dimethyl)silyl]oxymethyl]-3-hydroxy-tetrahydrofuran-2-yl]-6H-thiazolo[4,5-d]pyrimidine-2,7-dione (compound 38d, 3.3 g, 7.8 mmol) in THF (100 mL) was added Dess-Martine periodinane (3.68 g, 8.76 mmol) with stirring. After being stirred at room temperature for 2 hours, the resulting solution was filtered and the filtrate was concentrated in vacuo. The residue was purified by column chromatography on silica gel (eluting with 1:10 methanol in DCM) to afford 2.4 g crude product of 5-amino-3-[(2R,5S)-5-[[tert-butyl(dimethyl)silyl]oxymethyl]-3-oxo-tetrahydrofuran-2-yl]-6H-thiazolo[4,5-d]pyrimidine-2,7-dione (compound 38e). MS obsd. (ESI$^+$) [(M+H)$^+$]: 413.

Preparation of 5-amino-3-[(2R,3S,5S)-5-[[tert-butyl(dimethyl)silyl]oxymethyl]-3-hydroxy-tetrahydrofuran-2-yl]-6H-thiazolo[4,5-d]pyrimidine-2,7-dione

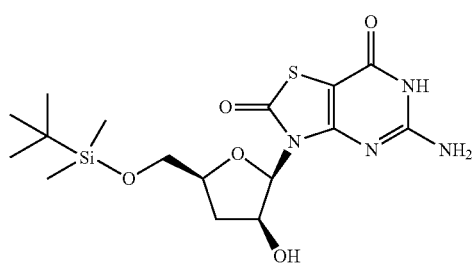

38f

To a stirred solution of 5-amino-3-[(2R,5S)-5-[[tert-butyl(dimethyl)silyl]oxymethyl]-3-oxo-tetrahydrofuran-2-yl]-6H-thiazolo[4,5-d]pyrimidine-2,7-dione (compound 38e, 1.0 g, 2.43 mmol) in THF (5 mL) was added lithium tri-tert-butoxyaluminum hydride solution (1M in THF, 2.7 mL, 2.7 mmol). After being stirred at room temperature for 2 hours, the resulting solution was quenched by saturated $NH_4Cl$ solution and filtered. The filtrate was concentrated in vacuo and the residue was purified by column chromatography on silica gel (eluting with 1:10 methanol in DCM) to afford 750 mg crude product of 5-amino-3-[(2R,3S,5S)-5-[[tert-butyl(dimethyl)silyl]oxymethyl]-3-hydroxy-tetrahydrofuran-2-yl]-6H-thiazolo[4,5-d]pyrimidine-2,7-dione (compound 38f). (Refer to *Tetrahedron* 1984, 40, 125-135).

Compound 38f: $^1$H NMR (400 MHz, $d_6$-DMSO) δ ppm: 7.00 (br. s., 2H), 6.08 (d, J=7.5 Hz, 1H), 5.35 (d, J=5.5 Hz, 1H), 4.53-4.65 (m, 1H), 3.91-3.99 (m, 1H), 3.82-3.89 (m, 1H), 3.70 (dd, J=10.5, 4.3 Hz, 1H), 2.11 (t, J=8.7 Hz, 2H), 0.84-0.86 (m, 9H), 0.84-0.88 (m, 10H), 0.84-0.86 (m, 9H), 0.01 (d, J=2.3 Hz, 6H).

Preparation of [5-amino-3-[(2R,3R,5S)-5-[[tert-butyl(dimethyl)silyl]oxymethyl]-3-(trifluoromethylsulfonyloxy)tetrahydrofuran-2-yl]-2-oxo-thiazolo[4,5-d]pyrimidin-7-yl] trifluoromethanesulfonate

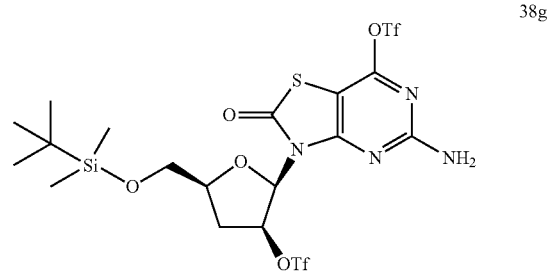 [SMILES: CC(C)(C)[Si](C)(C)OC[C@@H]1C[C@H](OS(=O)(=O)C(F)(F)F)[C@H](n2c(=O)sc3c(OS(=O)(=O)C(F)(F)F)nc(N)nc32)O1]

38g

To a stirred solution of 5-amino-3-[(2R,3S,5S)-5-[[tert-butyl(dimethyl)silyl]oxymethyl]-3-hydroxy-tetrahydrofuran-2-yl]-6H-thiazolo[4,5-d]pyrimidine-2,7-dione (compound 38f, 100 mg, 0.24 mmol) in DCM (15 mL) was added DMAP (147 mg, 1.2 mmol) and trifluoromathanesulfonyl chloride (122 mg, 0.7 mmol). After being stirred at room temperature for 2 hours, the resulting solution was washed with water, brine, dried over $Na_2SO_4$. The organic layer was concentrated in vacuo to afford 120 mg crude product of [5-amino-3-[(2R,3R,5S)-5-[[tert-butyl(dimethyl)silyl]oxymethyl]-3-(trifluoromethylsulfonyloxy)tetrahydrofuran-2-yl]-2-oxo-thiazolo[4,5-d]pyrimidin-7-yl] trifluoromethanesulfonate (compound 38g), which was used in next step without further purification. MS obsd. (ESI$^-$) [(M−H)$^+$]: 679.

Preparation of (2R,3S,5S)-2-(5-amino-2,7-dioxo-6H-thiazolo[4,5-d]pyrimidin-3-yl)-5-[[tert-butyl(dimethyl)silyl]oxymethyl]tetrahydrofuran-3-carbonitrile

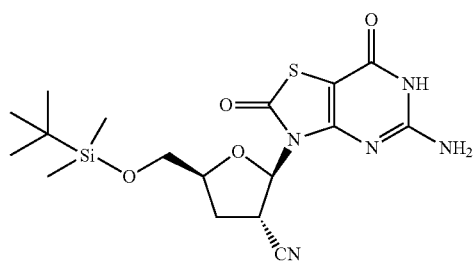

38h

To a stirred solution of [5-amino-3-[(2R,3R,5S)-5-[[tert-butyl(dimethyl)silyl]oxymethyl]-3-(trifluoromethylsulfonyloxy)tetrahydrofuran-2-yl]-2-oxo-thiazolo[4,5-d]pyrimidin-7-yl] trifluoromethanesulfonate (compound 38g, crude, 120 mg, 0.2 mmol) in DMF (2 mL) was added sodium cyanide (100 mg, 2.3 mmol). After being stirred at room temperature for 2 hours, the resulting solution was diluted by EtOAc, washed with brine, dried over $Na_2SO_4$ and concentrated in vacuo to afford 100 mg crude product of (2R,3S,5S)-2-(5-amino-2,7-dioxo-6H-thiazolo[4,5-d]pyrimidin-3-yl)-5-[[tert-butyl(dimethyl)silyl]oxymethyl]tetrahydrofuran-3-carbonitrile (compound 38h), which was used in next step without further purification. MS obsd. (ESI$^+$) [(M+H)$^+$]: 424.

Preparation of (2R,3S,5S)-2-(5-amino-2,7-dioxo-6H-thiazolo[4,5-d]pyrimidin-3-yl)-5-(hydroxymethyl)tetrahydrofuran-3-carbonitrile

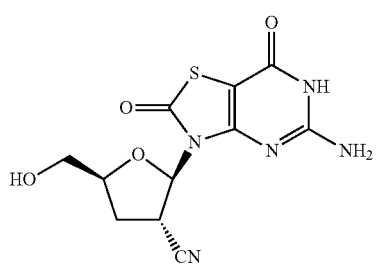

38

To a stirred solution of (2R,3S,5S)-2-(5-amino-2,7-dioxo-6H-thiazolo[4,5-d]pyrimidin-3-yl)-5-[[tert-butyl(dimethyl)silyl]oxymethyl]tetrahydrofuran-3-carbonitrile (compound 38h, crude, 100 mg) in THF (5 mL) was added TBAF solution (1M in THF, 6 mL, 6 mmol) at 0° C. After being stirred at room temperature for 4 hours, the reaction solution was washed with saturated $NH_4Cl$ solution, dried over $Na_2SO_4$ and concentrated in vacuo. The residue was purified by preparative HPLC to afford 9 mg of (2R,3S,5S)-2-(5-amino-2,7-dioxo-6H-thiazolo[4,5-d]pyrimidin-3-yl)-5-(hydroxymethyl)tetrahydrofuran-3-carbonitrile (Example 38) as a white solid.

Example 38: $^1$H NMR (400 MHz, d$_6$-DMSO) δ ppm: 11.11-11.99 (br. s., 1H), 7.10 (br. s., 2H), 6.15 (d, J=4.8 Hz, 1H), 4.86 (br. s., 1H), 4.33 (dt, J=9.5, 4.7 Hz, 1H), 4.07-4.20 (m, 1H), 3.50 (d, J=4.8 Hz, 2H), 2.44-2.48 (m, 1H), 2.23-2.36 (m, 1H). MS obsd. (ESI$^+$) [(M+H)$^+$]:310.

Example 39

5-Amino-3-[(2R,3R,5S)-5-(hydroxymethyl)-3-methylsulfanyl-tetrahydrofuran-2-yl]-6H-thiazolo[4,5-d]pyrimidine-2,7-dione

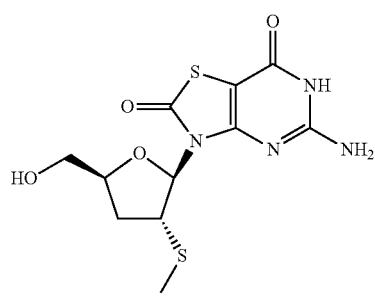

39

The title compound was prepared in analogy to Example 38 by using sodium methylsulfide instead of sodium cyanide. After being purified by preparative HPLC, 5-Amino-3-[(2R,3R,5S)-5-(hydroxymethyl)-3-methylsulfanyl-tetrahydrofuran-2-yl]-6H-thiazolo[4,5-d]pyrimidine-2,7-dione (Example 39) was afforded as a white solid.

Example 39: $^1$H NMR (400 MHz, d$_6$-DMSO) δ ppm: 11.37-11.55 (br. s., 1H), 6.91-7.10 (br. s., 2H), 5.94 (d, J=4.8 Hz, 1H), 4.75 (t, J=5.9 Hz, 1H), 4.03-4.15 (m, 2H), 3.45-3.55 (m, 3H), 2.09 (s, 3H), 1.92 (ddd, J=12.8, 6.8, 4.8 Hz, 1H). MS obsd. (ESI$^+$) [(M+H)$^+$]: 331

Example 40

5-Amino-3-[(2R,3R,5S)-3-(1-fluoro-1-methyl-ethyl)-5-(hydroxymethyl)tetrahydrofuran-2-yl]-6H-thiazolo[4,5-d]pyrimidine-2,7-dione

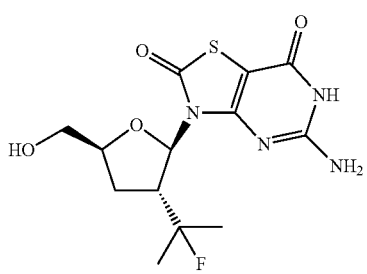

40

The title compound was prepared according to the following scheme:

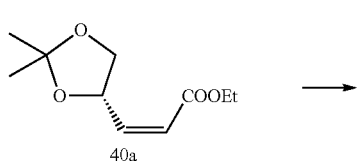

40a

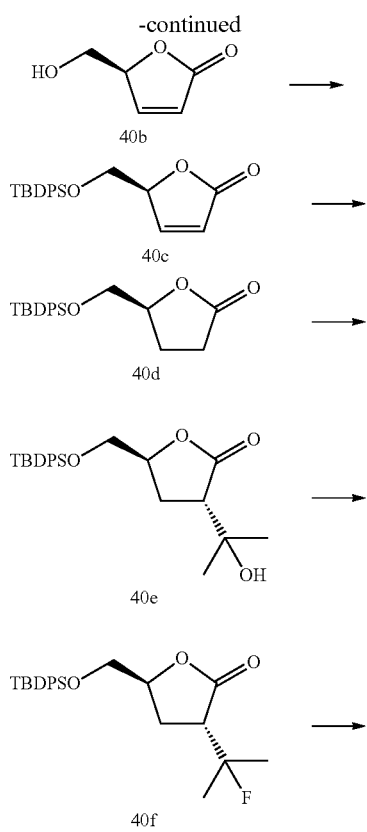

Preparation of (2S)-2-(hydroxymethyl)-2H-furan-5-one

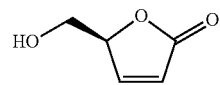

To a solution of ethyl (Z)-3-[(4S)-2,2-dimethyl-1,3-dioxolan-4-yl]prop-2-enoate (CAS #: 91926-90-8, Cat.#: PB1131897, commercially available from Pharma Block (Nanjing) R&D Co., Ltd, 4.0 g, 20.0 mmol) in methanol was added catalytic amount of concentrated sulfuric acid (25 μL of 10% concentrated sulfuric acid in methanol). The mixture was stirred at room temperature for 2 hours. The resulting mixture was concentrated in vacuo and the residue was purified by column chromatography on silica gel (eluting with 0-10% methanol in DCM) to afford 2.25 g of (2S)-2-(hydroxymethyl)-2H-furan-5-one (compound 40b) as a viscous oil.

Preparation of (2S)-2-[[tert-butyhdiphenyl)silyl]oxymethyl]-2H-furan-5-one

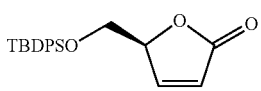

To a solution of 2.25 g of (2S)-2-(hydroxymethyl)-2H-furan-5-one (compound 40b, 2.11 g, 16.0 mmol) and imidazole (1.63 g, 24.0 mmol) in DCM was added tert-butyl(chloro)diphenylsilane (5.2 mL, 20.0 mmol) dropwise. The resulting mixture was stirred at room temperature for 2 hours. The resulting mixture was washed with brine. The aqueous layer was extracted with DCM. The organic layers were combined, washed with 1N hydrochloric acid, dried over Na$_2$SO$_4$ and concentrated in vacuo. The residue was purified by column chromatography on silica gel (eluting with 0-30% EtOAc in petroleum ether) to afford 4.6 g of (2S)-2-[[tert-butyl(diphenyl)silyl]oxymethyl]-2H-furan-5-one (compound 40c) as a white solid. MS obsd. (ESI$^+$) [(M+H)$^+$]: 353.

Preparation of (5S)-5-[[tert-butyl(diphenyl)silyl]oxymethyl]tetrahydrofuran-2-one

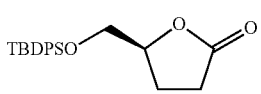

A solution of (2S)-2-[[tert-butyl(diphenyl)silyl]oxymethyl]-2H-furan-5-one (compound 40c, 2.8 g, 8.0 mmol) in EtOAc (40 mL) was stirred with 10% palladium on carbon (280 mg) under hydrogen atmosphere overnight. The resulting mixture was filtered and the filtrate was concentrated in vacuo to afford 2.7 g of (5S)-5-[[tert-butyl(diphenyl)silyl]oxymethyl]tetrahydrofuran-2-one (compound 40d) as a viscous oil. MS obsd. (ESI$^+$) [(M+H)$^+$]: 355.

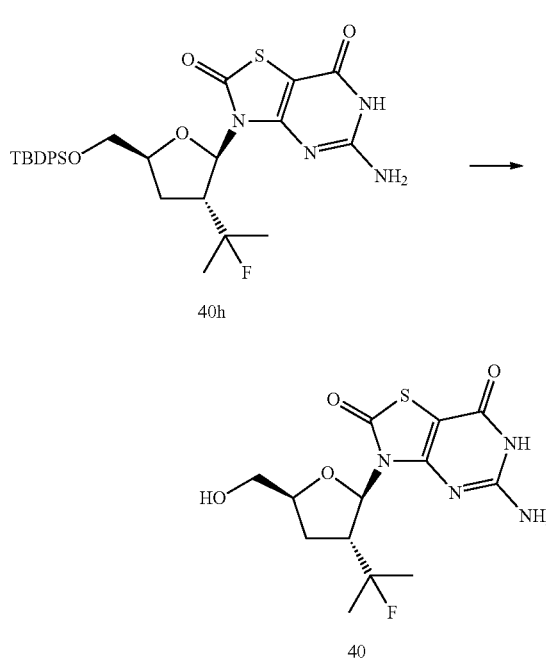

Preparation of (3S,5S)-5-[[tert-butyl(diphenyl)silyl]oxymethyl]-3-(1-hydroxy-1-methyl-ethyl)tetrahydrofuran-2-one

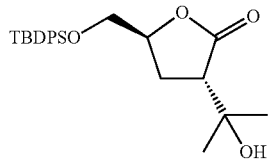

40e

To a cooled solution of (5S)-5-[[tert-butyl(diphenyl)silyl]oxymethyl]tetrahydrofuran-2-one (compound 40d, 5.00 g, 14.0 mmol) in dry tetrahydrofuran (28 mL) was added a solution of lithium bis(trimethylsilyl)azanide (1.3 M in THF, 11.8 mL, 15.4 mmol) dropwise at −78° C. under argon. After addition, the mixture was stirred at −78° C. for 1 hour. Then distilled acetone (1.23 mL, 15.4 mmol) was added dropwise to the mixture and the resulting mixture was stirred at −78° C. for another 2 hours. The reaction was quenched by saturated NH$_4$Cl solution and extracted with EtOAc (30 mL) three times. The combined organic layers were dried over Na$_2$SO$_4$ and concentrated in vacuo. The residue was purified by column chromatography on silica gel (eluting with 0-30% EtOAc in petroleum ether) to afford 5.7 g of (3S,5S)-5-[[tert-butyl(diphenyl)silyl]oxymethyl]-3-(1-hydroxy-1-methyl-ethyl)tetrahydrofuran-2-one (compound 40e) as a light yellow oil. MS obsd. (ESI$^+$) [(M+NH$_4$)$^+$]: 430. (For the synthesis, please refer to: *Tetrahedron* 1997, 53, 6281-6294).

Preparation of (3R,5S)-5-[[tert-butyl(diphenyl)silyl]oxymethyl]-3-(1-fluoro-1-methyl-ethyl)tetrahydrofuran-2-one

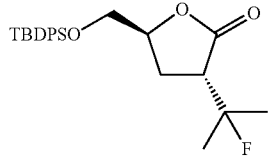

40f

To a solution of diethylaminosulfur trifluoride (414 μL, 3.0 mmol) in DCM (10 mL) at −78° C. was added a solution of (3S,5S)-5-[[tert-butyl(diphenyl)silyl]oxymethyl]-3-(1-hydroxy-1-methyl-ethyl)tetrahydrofuran-2-one (compound 40e, 1.03 g, 2.5 mmol) in DCM (10 mL) dropwise. The resulting mixture was warmed up to room temperature and stirred at room temperature overnight. The resulting mixture was concentrated in vacuo and the residue was purified by column chromatography on silica gel (eluting with 0-20% EtOAc in petroleum ether) to afford 820 mg of (3R,5S)-5-[[tert-butyl(diphenyl)silyl]oxymethyl]-3-(1-fluoro-1-methyl-ethyl)tetrahydrofuran-2-one (compound 40f) as a viscous oil. MS obsd. (ESI$^+$) [(M+H)$^+$]: 415.

Preparation of [(3R,5S)-5-[[tert-butyl(diphenyl)silyl]oxymethyl]-3-(1-fluoro-1-methyl-ethyl)tetrahydrofuran-2-yl]acetate

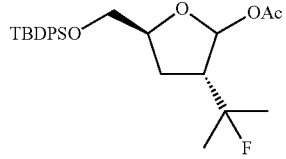

40g

To a cooled solution of (3R,5S)-5-[[tert-butyl(diphenyl)silyl]oxymethyl]-3-(1-fluoro-1-methyl-ethyl)tetrahydrofuran-2-one (compound 40f, 820 mg, 1.92 mmol) in dry DCM (10 mL) at −78° C. was added diisobutyl aluminium hydride (1.0 M in toluene, 6.0 mL, 6.0 mmol) dropwise. The resulting mixture was stirred at −78° C. for 1 hour. Then to the mixture was added pyridine (790 mg, 10 mmol), acetic anhydride (0.93 mL, 10.0 mmol) and DMAP (732 mg, 6.0 mmol). The reaction mixture was allowed to warm to −20° C. slowly and stirred at −20° C. for several hours until the reaction was complete. The resulted mixture was quenched by brine and extracted with EtOAc (30 mL) three times. The organic layers were combined, dried over Na$_2$SO$_4$ and concentrated in vacuo. The residue was purified by column chromatography on silica gel (eluting with 0-20% EtOAc in petroleum ether) to afford 360 mg of [(3R,5S)-5-[[tert-butyl(diphenyl)silyl]oxymethyl]-3-(1-fluoro-1-methyl-ethyl)tetrahydrofuran-2-yl]acetate (compound 40g) as a viscous oil. MS obsd. (ESI$^+$) [(M+H)$^+$]: 459.

Preparation of 5-amino-3-[(2R,3R,5S)-5-[[tert-butyl(diphenyl)silyl]oxymethyl]-3-(1-fluoro-1-methyl-ethyl)tetrahydrofuran-2-yl]-6H-thiazolo[4,5-d]pyrimidine-2,7-dione

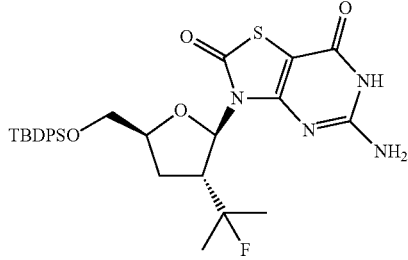

40h

A mixture of 5-amino-3,6-dihydrothiazolo[4,5-d]pyrimidine-2,7-dione (162 mg, 0.87 mmol) and bis(trimethylsilyl)acetamide (527 mg, 2.61 mmol) was heated with stirring at 75° C. under argon until the mixture became clear. The mixture was cooled to room temperature. To the previous reaction mixture, [(3R,5S)-5-[[tert-butyl(diphenyl)silyl]oxymethyl]-3-(1-fluoro-1-methyl-ethyl)tetrahydrofuran-2-yl]acetate (compound 40g, 280 mg, 1.02 mmol) and trimethylsilyltrifluoromethanesulfonate (290 mg, 1.31 mmol) were introduced. The resulting mixture was heated at 75° C. under argon for 3 hours. Then the resulting mixture was concentrated in vacuo to remove the solvent and the residue was purified by column chromatography on silica gel (eluting with 0-5% methanol in DCM) to afford 225 mg of 5-amino-3-[(2R,3R,5S)-5-[[tert-butyl(diphenyl)silyl]oxymethyl]-3-(1-fluoro-1-methyl-ethyl)tetrahydrofuran-2-yl]-6H-thiazolo[4,5-d]pyrimidine-2,7-dione (compound 40h) as a brown solid. MS obsd. (ESI+) [(M+H)+]: 583.

Preparation of 5-amino-3-[(2R,3R,5S)-3-(1-fluoro-1-methyl-ethyl)-5-(hydroxymethyl)tetrahydrofuran-2-yl]-6H-thiazolo[4,5-d]pyrimidine-2,7-dione

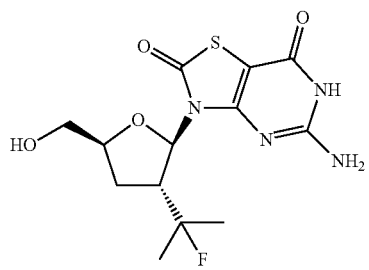

40

A mixture of 5-amino-3-[(2R,3R,5S)-5-[[tert-butyl(diphenyl)silyl]oxymethyl]-3-(1-fluoro-1-methyl-ethyl)tetrahydrofuran-2-yl]-6H-thiazolo[4,5-d]pyrimidine-2,7-dione (compound 40h, 66 mg, 0.12 mmol) and NH₄F (133 mg, 3.6 mmol) in methanol was heated under reflux for 1.5 hrs. The resulting mixture was concentrated in vacuo and the residue was purified by preparative HPLC to afford 10 mg of 5-amino-3-[(2R,3R,5S)-3-(1-fluoro-1-methyl-ethyl)-5-(hydroxymethyl)tetrahydrofuran-2-yl]-6H-thiazolo[4,5-d]pyrimidine-2,7-dione (Example 40) as a white solid.

Example 40: ¹H NMR (400 MHz, d₆-DMSO) δ ppm: 11.27-11.40 (br. s., 1H), 6.90-7.08 (br. s., 2H), 6.03-6.10 (m, 1H), 4.65-4.74 (m, 1H), 3.92-4.03 (m, 1H), 3.42-3.53 (m, 2H), 3.18-3.30 (m, 1H), 2.10-2.23 (m, 1H), 1.96-2.06 (m, 1H), 1.19-1.42 (m, 6H). MS obsd. (ESI+) [(M+H)+]: 345.

Example 41

5-Amino-3-[(2R,3R,5S)-5-(hydroxymethyl)-3-(2-methylallyl)tetrahydrofuran-2-yl]-6H-thiazolo[4,5-d]pyrimidine-2,7-dione

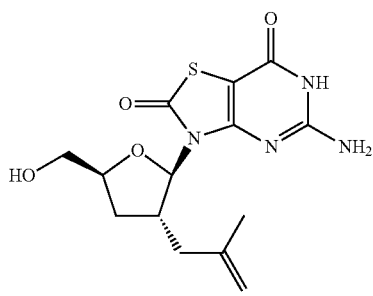

41

The title compound was prepared according to the following scheme.

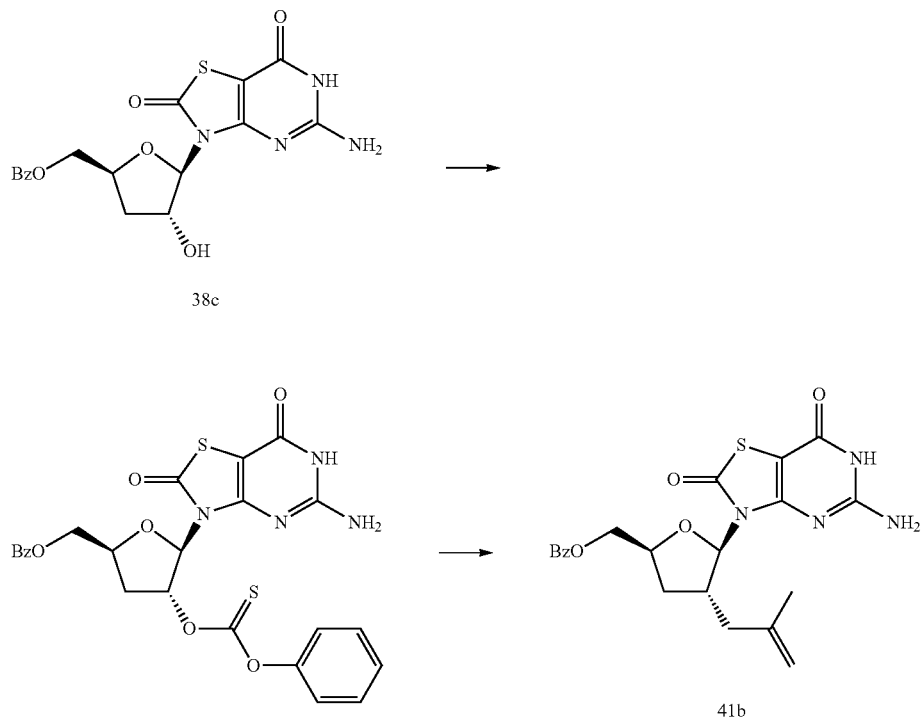

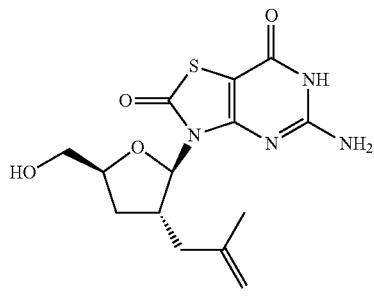

41

Preparation of [(2S,4R,5R)-5-(5-amino-2,7-dioxo-6H-thiazolo[4,5-d]pyrimidin-3-yl)-4-phenoxycarbothioyloxy-tetrahydrofuran-2-yl]methyl benzoate

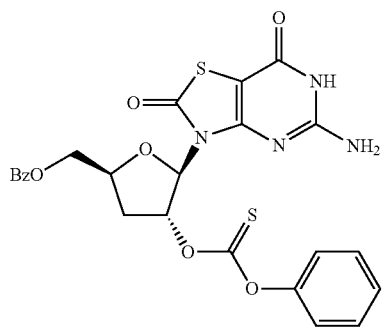

41a

A mixture of [(2S,4R,5R)-5-(5-amino-2,7-dioxo-6H-thiazolo[4,5-d]pyrimidin-3-yl)-4-hydroxy-tetrahydrofuran-2-yl]methyl benzoate (compound 38c, 2.08 g, 5.0 mmol), O-phenyl chloromethanethioate (0.80 mL) and DMAP (1.22 g, 10.0 mmol) in DCM (50 mL) was stirred at room temperature overnight. The resulting mixture was washed with brine, dried over $Na_2SO_4$, and concentrated in vacuo. The residue was purified by column chromatography on silica gel (eluting with 0-30% EtOAc in petroleum ether) to afford 2.20 g of [(2S,4R,5R)-5-(5-amino-2,7-dioxo-6H-thiazolo[4,5-d]pyrimidin-3-yl)-4-phenoxycarbothioyloxy-tetrahydrofuran-2-yl]methyl benzoate (compound 41a) as a pale solid. MS obsd. (ESI⁻) [(M–H)⁺]: 539.

Preparation of [(2S,4R,5R)-5-(5-amino-2,7-dioxo-6H-thiazolo[4,5-d]pyrimidin-3-yl)-4-(2-methylallyl) tetrahydrofuran-2-yl]methyl benzoate

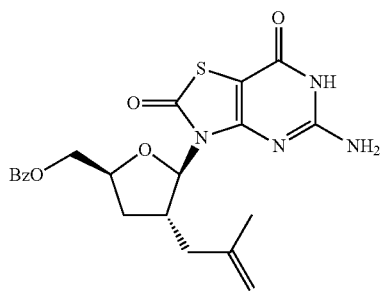

41b

A mixture of [(2S,4R,5R)-5-(5-amino-2,7-dioxo-6H-thiazolo[4,5-d]pyrimidin-3-yl)-4-phenoxycarbothioyloxy-tetrahydrofuran-2-yl]methyl benzoate (compound 41a, 324 mg, 0.60 mmol), 2,2'-azobis(2-methylpropionitrile) (50 mg, 0.30 mmol) and tributyl(2-methylallyl)stannane (0.70 mL, 3.0 mmol) in anhydrous toluene (10 mL) was degassed with argon and then heated with stirring at 80° C. for 4 hours. The resulting mixture was stirred with saturated aqueous $NH_4F$ at room temperature for 2 hours, and then extracted with DCM twice. The combined organic layers were dried over $Na_2SO_4$ and concentrated in vacuo. The residue was purified by column chromatography on silica gel (eluting with 0-30% EtOAc in petroleum ether) to afford 190 mg of [(2S,4R,5R)-5-(5-amino-2,7-dioxo-6H-thiazolo[4,5-d]pyrimidin-3-yl)-4-(2-methylallyl)tetrahydrofuran-2-yl]methyl benzoate (compound 41b) as a brown solid. MS obsd. (ESI⁻) [(M–H)⁺]: 441.

Preparation of 5-amino-3-[(2R,3R,5S)-5-(hydroxymethyl)-3-(2-methylallyl)tetrahydrofuran-2-yl]-6H-thiazolo[4,5-d]pyrimidine-2,7-dione

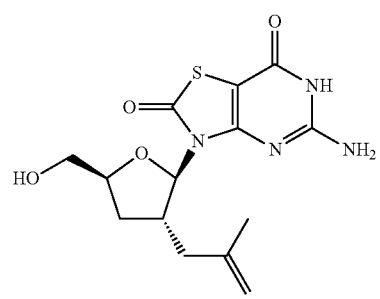

41

A solution of [(2S,4R,5R)-5-(5-amino-2,7-dioxo-6H-thiazolo[4,5-d]pyrimidin-3-yl)-4-(2-methylallyl)tetrahydrofuran-2-yl]methyl benzoate (compound 41b, 180 mg, 0.41 mmol) in methanol was stirred with $K_2CO_3$ (150 mg, 1.09 mmol) at room temperature for 4 hours. The reaction was quenched by addition of acetic acid and the resulting mixture was concentrated in vacuo. The residue was purified by preparative HPLC to afford 41 mg of 3-[(2R,3R,5S)-3-allyl-5-(hydroxymethyl)tetrahydrofuran-2-yl]-5-amino-6H-thiazolo[4,5-d]pyrimidine-2,7-dione (Example 41) as a white powder.

Example 41: $^1$H NMR (400 MHz, $d_6$-DMSO) δ ppm: 11.03-11.29 (m, 1H), 6.76-7.04 (m, 2H), 5.68 (d, J=6.02 Hz, 1H), 4.62-4.70 (m, 3H), 3.96-4.10 (m, 1H), 3.47 (t, J=5.27 Hz, 2H), 3.24-3.30 (m, 1H), 2.16-2.25 (m, 1H), 2.13 (d, J=7.53 Hz, 2H), 1.67-1.76 (m, 1H), 1.62 (s, 3H). MS obsd. (ESI⁺) [(M+H)⁺]: 339.

Example 42

[(1S)-1-[(2S,4R,5R)-5-(5-Amino-2,7-dioxo-6H-thiazolo[4,5-d]pyrimidin-3-yl)-4-hydroxy-tetrahydrofuran-2-yl]propyl] 2-methylpropanoate

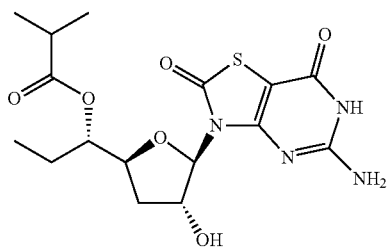

42

The title compound was prepared according to the following Scheme.

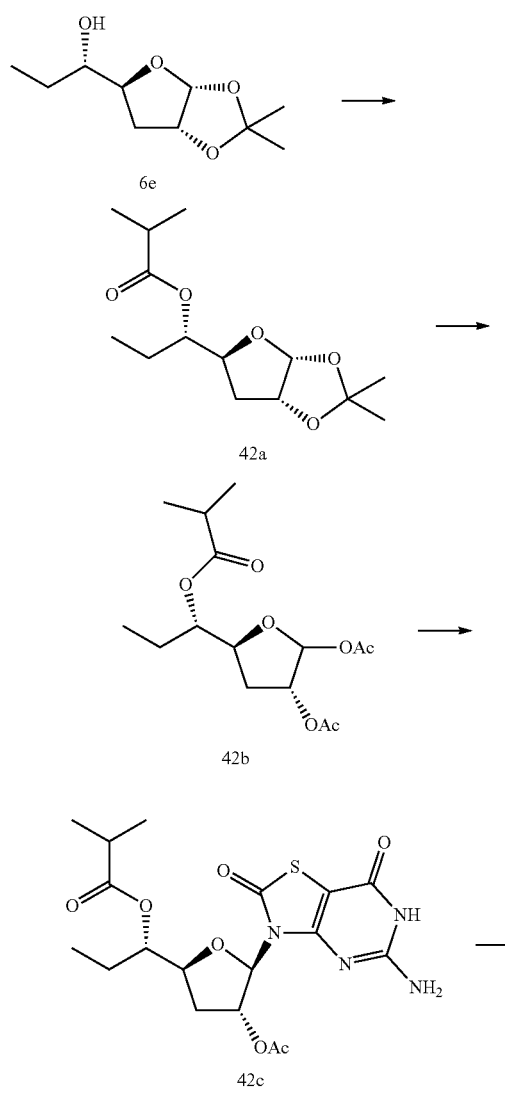

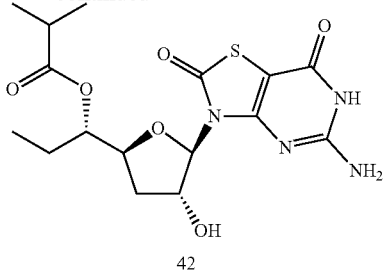

42

Preparation of [(1S)-1-[(3aR,5S,6aR)-2,2-dimethyl-3a,5,6,6a-tetrahydrofuro[2,3-d][1,3]dioxol-5-yl]propyl] 2-methylpropanoate 42a To a cooled solution of (1S)-1-[(3aR,5S,6aR)-2,2-dimethyl-3a,5,6,6a-tetrahydrofuro[2,3-d][1,3]dioxol-5-yl]propan-1-ol (compound 6e, 505.6 mg, 2.5 mmol) in pyridine was added isobutyryl chloride (0.39 mL, 3.72 mmol) dropwise while cooled with an ice-water bath. After the addition, the mixture was warmed to room temperature and stirred at room temperature overnight. The resulting mixture was diluted with EtOAc and washed with a saturated NH$_4$Cl solution. The organic layer was dried over Na$_2$SO$_4$ and concentrated in vacuo. The residue was purified by column chromatography on silica gel (eluting with 0-30% EtOAc in petroleum ether) to afford 470 mg of [(1S)-1-[(3aR,5S,6aR)-2,2-dimethyl-3a,5,6,6a-tetrahydrofuro[2,3-d][1,3]dioxol-5-yl]propyl] 2-methylpropanoate (compound 42a).

Preparation of [(1S)-1-[(2S,4R,5R)-4,5-diacetoxytetrahydrofuran-2-yl]propyl] 2-methylpropanoate

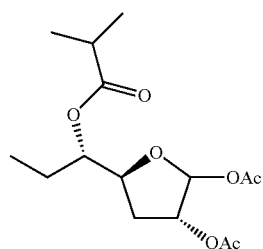

42b

To a stirred solution of [(1S)-1-[(3aR,5S,6aR)-2,2-dimethyl-3a,5,6,6a-tetrahydrofuro[2,3-d][1,3]dioxol-5-yl]propyl] 2-methylpropanoate (compound 42a, 470 mg, 1.73 mmol), acetic anhydride (0.81 mL, 8.64 mmol) and acetic acid (0.51 mL, 8.64 mmol) in DCM (10 mL) was added concentrated sulfuric acid (18.4 μL, 0.17 mmol). The resulting mixture was stirred at room temperature overnight. The resulting mixture was concentrated in vacuo. The residue was purified by column chromatography on silica gel (eluting with 0-20% EtOAc in petroleum ether) to afford 105 mg of [(1S)-1-[(2S,4R,5R)-4,5-diacetoxytetrahydrofuran-2-yl] propyl] 2-methylpropanoate (compound 42b).

Preparation of [(1S)-1-[(2S,4R,5R)-4-acetoxy-5-(5-amino-2,7-dioxo-6H-thiazolo[4,5-d]pyrimidin-3-yl) tetrahydrofuran-2-yl]propyl] 2-methylpropanoate

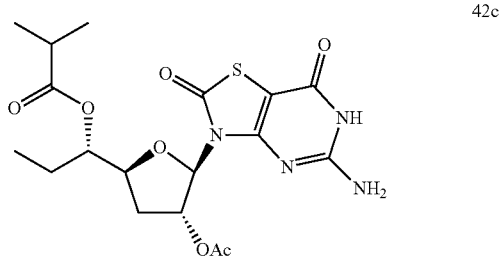 [SMILES: CC[C@H](OC(=O)C(C)C)[C@@H]1C[C@@H](OC(C)=O)[C@H](n2c(=O)sc3c(=O)[nH]c(N)nc32)O1]

42c

To a suspension of 5-amino-3,6-dihydrothiazolo[4,5-d]pyrimidine-2,7-dione (63 mg, 0.34 mmol) in ACN (5 mL) was added BSA (252 μL, 1.02 mmol). The resulting reaction mixture was then stirred at 70° C. under argon for 0.5 hour to form a clear solution. After the solution was cooled to room temperature, [(1S)-1-[(2S,4R,5R)-4,5-diacetoxytetrahydrofuran-2-yl]propyl] 2-methylpropanoate (compound 42b, 105 mg, 0.34 mmol) and TMSOTf (113 μL, 0.51 mmol) were added in sequence. After being heated with stirring at 70° C. for 14 hours, the resulting mixture was concentrated in vacuo to remove the solvent and the residue was purified by column chromatography on silica gel (eluting with 0-5% methanol in DCM) to afford 75 mg of [(1S)-1-[(2S,4R,5R)-4-acetoxy-5-(5-amino-2,7-dioxo-6H-thiazolo[4,5-d]pyrimidin-3-yl)tetrahydrofuran-2-yl]propyl] 2-methylpropanoate (compound 42c) as a light yellow solid.

Preparation of [(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl] 2-methylpropanoate

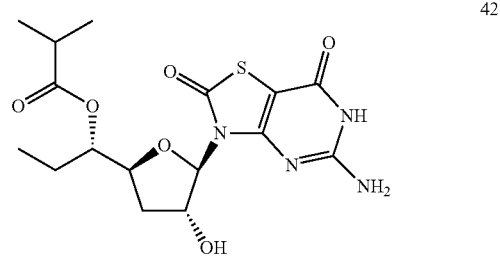 [SMILES: CC[C@H](OC(=O)C(C)C)[C@@H]1C[C@@H](O)[C@H](n2c(=O)sc3c(=O)[nH]c(N)nc32)O1]

42

A mixture of [(1S)-1-[(2S,4R,5R)-4-acetoxy-5-(5-amino-2,7-dioxo-6H-thiazolo[4,5-d]pyrimidin-3-yl)tetrahydrofuran-2-yl]propyl] 2-methylpropanoate (compound 42c, 70 mg, 0.16 mmol) and $K_2CO_3$ (13.2 mg, 0.096 mmol) in methanol (0.5 mL) and tetrahydrofuran (2 mL) was stirred at room temperature overnight. The reaction was quenched by addition of acetic acid (1 drop). The resulting mixture was concentrated in vacuo to remove the solvents and the residue was purified by preparative HPLC to afford 18.2 mg of [(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl] 2-methylpropanoate (Example 42) as a pale solid.

Example 42: $^1$H NMR (400 MHz, $CD_3OD$) δ ppm: 5.89-5.95 (m, 1H), 4.93-5.01 (m, 2H), 4.29-4.38 (m, 1H), 2.51-2.63 (m, 2H), 1.83-1.93 (m, 1H), 1.58-1.76 (m, 2H), 1.15 (dd, J=4.02, 7.03 Hz, 6H), 0.88-0.95 (m, 3H). MS obsd. (ESI$^+$) [(M+H)$^+$]: 399.

Example 43

HEK293-Blue-hTLR-7 Cells Assay

A stable HEK293-Blue-hTLR-7 cell line was purchased from InvivoGen (Cat.#: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7 for 20 hours. The cell culture supernatant SEAP reporter activity was determined using QUANTI-Blue™ kit (Cat.#: rep-qbl, Invivogen, San Diego, Ca, USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum for 24 h. Then the HEK293-Blue-hTLR-7 cells were incubated with addition of 20 μL test compound in a serial dilution in the presence of final DMSO at 1% and perform incubation under 37° C. in a $CO_2$ incubator for 20 hours. Then 20 μL of the supernatant from each well was incubated with 180 μL Quanti-blue substrate solution at 37° C. for 2 hours and the absorbance was read at 620~655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002).

The TLR7 agonism activity in HEK293-hTLR-7 assay of compounds of present invention is listed in Table 1. The Examples were tested in the above assay and found to have EC50 of about 10 μM to about 90 μM.

TABLE 1

Activity of Compounds in HEK293- hTLR-7 assay

| Example No. | HEK293- hTLR-7 $EC_{50}$ (μM) |
|---|---|
| ANA-122 | 446 |
| 1-A | 52 |
| 5-A | 48 |

TABLE 1-continued

Activity of Compounds in HEK293- hTLR-7 assay

| Example No. | HEK293- hTLR-7 $EC_{50}$ (µM) |
|---|---|
| 8-A | 87 |
| 10-A | 63 |
| 14-A | 48 |
| 18-A | 12 |
| 19-A | 38 |
| 22-A | 14 |
| 23-A | 26 |
| 24-A | 70 |
| 26 | 29 |
| 26-A | 12 |
| 27-A | 15 |
| 28 | 10 |
| 29 | 29 |
| 30 | 15 |
| 31 | 70 |
| 32 | 67 |
| 39 | 62 |
| 42 | 51 |

A reference compound disclosed in patent WO2006066080(A1) as compound 122 (herein referred as ANA-122) was also tested for TLR7 agonism activity in HEK293-hTLR-7 assay mentioned above, EC50 of ANA-122 was found to be 446 µM.

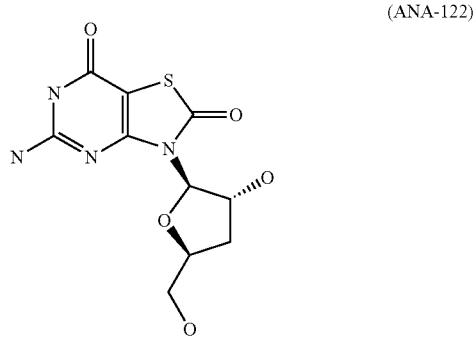 [SMILES: Nc1nc2c(sc(=O)n2[C@@H]2O[C@H](CO)C[C@H]2O)c(=O)[nH]1]

(ANA-122)

Example 44

Metabolism of Prodrugs: Formula (II) or Formula (IIa)

A study was undertaken to evaluate the metabolic conversion of prodrugs, formula (II) or formula (IIa), to compounds of formula (I) or formula (Ia) of the present invention. The produgs, formula (II) or formula (IIa), can be metabolized to the active compound of formula (I) or formula (Ia) and other compounds of the invention in the body if they are served as prodrugs. Hepatocytes are often used to assess the degree of metabolic conversion of prodrugs in the body of animal or human.

A study was undertaken to evaluate the metabolic conversion of prodrugs, Example 2-A, Example 3-A, Example 4-A, Example 16-A and Example 17-A, to the corresponding active forms, Example 1-A and Example 14-A, in the presence of human hepatocytes. The formation of active forms, Example 1-A and Example 14-A, were monitored in the study. For comparison, the metabolic conversion of famciclovir to penciclovir was also assessed.

Hepatocytes Suspension

Cryopreserved hepatocytes plating medium (Cat.#: PY-HMD-01) was purchased from RILD Research Institute for Liver Diseases (Shanghai) Co. Ltd. Cryopreserved human hepatocyte (Cat.#: X008005, Lot#:VRR) was purchased from In Vitro Technologies (Baltimore, Md.).

The stock hepatocyte suspension was prepared from cryopreserved hepatocytes in plating medium at the concentration of $1.8 \times 10^6$ cells/mL.

Working Solutions of Compounds

Compounds were dissolved in DMSO to make 50 mM stock solutions. 10 µl of the stock solution was diluted to 5 mL plating medium to get a 100 µM working solution.

Incubations

Reaction suspensions were prepared in 24-well cell culture plate by mixing 200 µl of hepatocytes suspension (Cyno or human) and 200 µl of working solution. The final incubation contained $0.9 \times 10^6$ cells/mL and 50 µM compound. The above mixtures were incubated at 37° C. in a humidified 5% $CO_2$ atmosphere, with a 150 rpm shaking.

Preparation of Samples for Analysis

After 180 min of incubation, 200 µL of the incubation mixture was transferred to 1.5 mL tube and quenched with 400 µL stop solution (ice-cold acetonitrile with 0.2 µM Tolbutamide as internal standard). The samples were centrifuged at 12000 rpm for 10 minutes and the resultant supernatants were subjected to LC-MS/MS analysis.

The calibration curves were prepared in the following way. To a 200 µL of cell suspension (cell density of 1.8 million cells/mL), 198 µL of hepatocyte plating medium and 2 µL of the appropriate concentration of the compound in DMSO were added. Samples were mixed thoroughly and 200 µL of the mixture was transferred to 400 uL of the stop solution (see above). The standard curve range is from 1 µM to 25 µM.

Bioanalysis

The compounds were quantified on an API5500 LC-MC/MC instrument in the ESI-Positive MRM mode. The results of prodrug conversion and metabolite generation are summarized in Table 2.

TABLE 2

Concentration of the metabolites formed in human hepatocytes after 3-hour incubation of 50 µM of prodrugs.

| Example No. | Metabolized Product | Product Concentration in human hepatocytes (µM) |
|---|---|---|
| 2-A | 1-A | 8.7 |
| 3-A | 1-A | 19.3 |
| 4-A | 1-A | 10.3 |
| 16-A | 14-A | 7.3 |
| 17-A | 14-A | 7.3 |
| Famciclovir | Penciclovir | 23.5 |

In human hepatocytes, compounds of Example 2-A, Example 3-A, Example 4-A, Example 16-A and Example 17-A as well as famciclovir were metabolized to yield the corresponding active metabolites of Example 1-A, Example 14-A and penciclovir, respectively.

Example 45

TLR7 Agonist Example 1-A Activates Murine TLR7

The potency of the TLR7 agonist Example 1-A activating murine TLR7 was assessed using a stable HEK293-Blue-mTLR7 cell line available from InvivoGen (Cat.#: hkbmtlr7, San Diego, Calif., USA). Similar to the HEK293-Blue-hTLR7 as described in Example 43, the HEK293-Blue-mTLR7 is designed for studying the stimulation of murine TLR7 by monitoring the activation of NF-κB. A SEAP reporter gene was placed under the control of the IFN-β minimal promoter fused to five NF-κB and AP-1-binding sites. The SEAP expression was induced by the activation of NF-κB and AP-1 upon stimulation of murine TLR7 with TLR7 ligands. SEAP expression in cell culture supernatant was determined using a QUANTI-Blue™ kit (Cat.#: rep-qbl, Invivogen, San Diego, Ca, USA), a detection medium that turns purple/blue in the presence of alkaline phosphatase, at a wavelength of 655 nm.

HEK293-Blue-mTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum for 24 hours. The HEK293-cells were then incubated with 20 μL of test compound in a serial dilution in the presence of final 1% DMSO at 37° C. in a $CO_2$ incubator for 20 hours. 20 μL of the supernatant from each well was incubated with 180 μL Quanti-blue substrate solution at 37° C. for 2 hours and the absorbance was measured at 655 nm using a spectrophotometer.

As shown in FIG. 1, Example 1-A activates murine TLR7 in a dose dependent manner with an EC50 of 71.8 μM.

Example 46

TLR7 Agonist Example 1-A Induces Antiviral Cytokines in Murine Peripheral Blood Mononuclear Cells (PBMC) In Vitro To demonstrate TLR7 activation on leukocytes by the compound of this invention, murine PBMC (available from ALLCells, LLC.) were subjected to stimulation by Example 1-A. 70 million murine PBMC (C57b1/6 strain) were seeded into each well of a 24-well plate at the concentration of $2 \times 10^6$/mL in 1.5 mL RPMI-1640 medium containing 10% fetal bovine serum. The seeded PBMC were incubated with Example 1-A over a concentration range from 2 to 10 μM for 24 hours. 50 μL of cell culture medium was collected and analyzed with a 36plex Procarta multiplex kit (ebioscience EPX360-26092-901, eBioscience), which measured the levels of 15 cytokine analytes, following the manufacturer's instruction.

Figure 2:
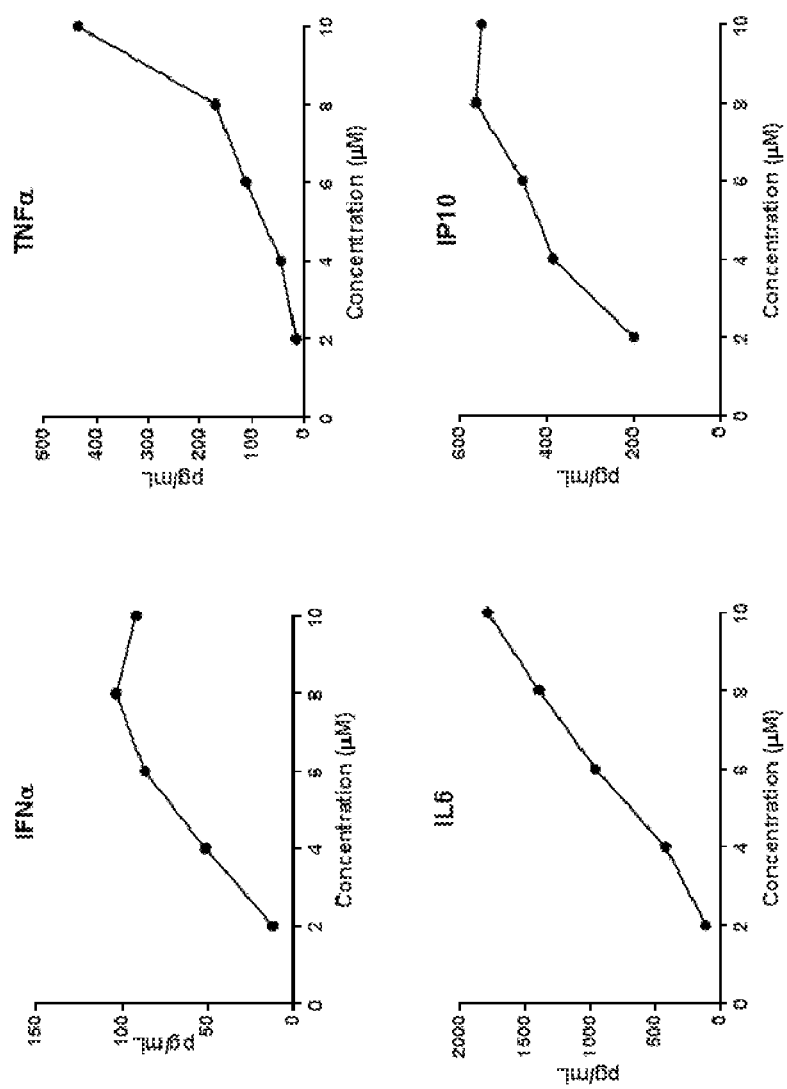
FIG. 2: In vitro cytokine induction by Example 1-A in murine PBMC. Murine PBMC were stimulated with Example 1-A at indicated concentrations. Supernatants were collected at 24 hour post treatment and cytokine levels in supernatants were assessed by a multiplex assay.

As shown in FIG. 2, high levels of IFNα, IP10, TNFα, and IL-6 were found induced by Example 1-A in a dose-dependent manner. The increased levels of these cytokines in the stimulated PBMC demonstrate that TLR7 agonist Example 1-A induces immune activation and has the potential to treat infectious diseases.

Example 47

Example 4-A Reduces HBV DNA and HBsAg in AAV-HBV Model

Example 4-A was evaluated for its in vivo antiviral efficacy using an AAV-HBV mouse model. This mouse model for HBV infection was generated by injecting C57BL/6 mice with a recombinant adeno-associated virus (AAV) carrying a replicable HBV (hepatitis B virus) genome (AAV-HBV). In 2-3 weeks post infection, high levels of HBV viral markers, such as HBV genomic DNA and HBsAg (HBV surface antigen), was detected in the sera of infected mice. With persistent HBV viremia and fully competent immune system, the AAV-HBV model is suitable for investigating the in vivo efficacy of Example 4-A.

Two independent in vivo studies were conducted to assess the antiviral potency of Example 4-A at 100 mg/kg and 300 mg/kg respectively. For each study, ten 4-5 week old male C57BL/6 mice, specific pathogen free, were available from Shanghai Laboratory Animal Center of Chinese Academy of Sciences (SLAC) and housed in an animal care facility in individually ventilated cages under controlled temperature and light conditions following the Institutional Animal Care guidelines. AAV-HBV virus stock was purchased from Beijing FivePlus Molecular Medicine Institute (Beijing, China). C57BL/6 mice were injected with 200 μL of recombinant virus in saline buffer through tail vein injection. The mice were bled on day 14 post injection to monitor the levels of HBsAg, HBeAg, and HBV genomic DNA in serum, and randomly grouped based on these HBV biomarker levels. The grouped mice were then treated following the study design as shown in Table 3.

TABLE 3

In vivo study in AAV-HBV mouse model

| Study # | Group # | Mice # | Treatment Compound | Dose (mg/kg) | Drug delivery |
|---|---|---|---|---|---|
| 1 | 1 | 5 | Vehicle | 0 | PO, QOD, 42D |
|   | 2 | 5 | Example 4-A | 100 |   |
| 2 | 3 | 5 | Vehicle | 0 |   |
|   | 4 | 5 | Example 4-A | 300 |   |

Mice in groups 1 and 3 were treated with vehicle placebo (2% Klucel LF, 0.1% Polysorbate 80, and 0.1% Parabens in water); Mice in groups 2 and 4 were orally dosed with Example 4-A at 100 mg/kg and 300 mg/kg respectively, every other day (QOD). All the mice were treated for a total of 6 weeks. Serum samples were collected twice a week to monitor the levels of HBV biomarkers. Serum HBsAg was measured using CLIA kits (Autobio Diagnostics Co., Ltd, Zhengzhou, China) according to the manufacturer's instructions. The lower limit of quantification (LLQ) for HBsAg was 0.1 ng/mL. Serum dilution of 500-fold (for HBsAg) was used to obtain values within the linear range of the standard curve. Serum HBV DNA was extracted using a MagNA Pure 96 DNA and Viral NA Small Volume Kit (Roche) following the manufacturer's instructions. The DNA samples were analyzed by real-time quantitative PCR (qPCR) using a HBV-specific primer and probe set for specific amplification and detection of a 128 bp HBV genome region from the nucleotide 2969 to 3096. The LLQ for HBV DNA was 20 copies/μL.

Figure 3:
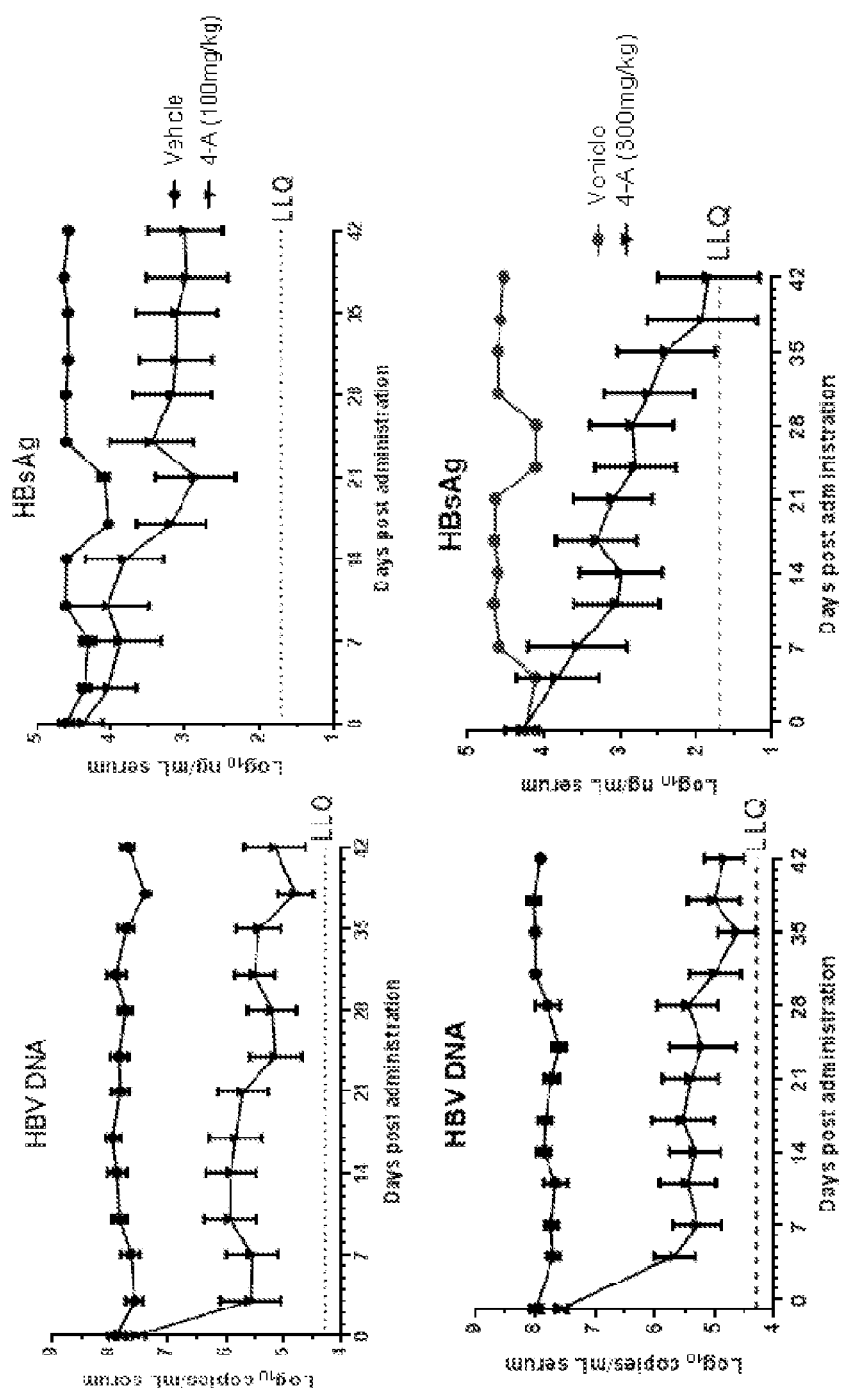
FIG. 3: HBV DNA and HBsAg in the AAV-HBV infected mice treated with Vehicle, a low dose of Example 6-A at 30 mg/kg, and a high dose of Example 6-A at 100 mg/kg. The treatment started after the mice were infected with AAV-HBV for 29 days. They were given the treatment for 42 days, and HBV DNA and HBsAg in mouse serum were measured on the indicated time points by RT-qPCR and HBsAg CLIA respectively. The results were presented as mean±SEM. LLQ: lower limit of quantification.

As shown in FIG. 3, after the 6-week treatment, Example 4-A at 100 mg/kg induced more than 2-log reduction in HBV DNA and 1.5-log reduction in HBsAg. At a higher dose as 300 mg/kg, Example 4-A reduced HBV DNA by more than 3-log and HBsAg by 2.7-log at the end of the treatment. The results of this study clearly demonstrate the in vivo antiviral efficacy of Example 4-A and underscore the potential of compounds of this invention to develop novel therapy for infectious diseases.

We claim:
1. A compound of formula (I),

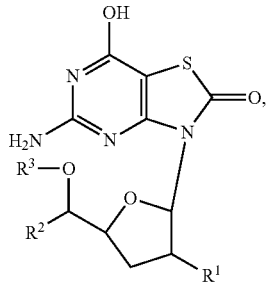

wherein
$R^1$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}$alkyl$)_2$N—, $C_{1-6}$alkylcarbonyl-NH— or heterocyclic amino;
$R^2$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^3$ is hydrogen or $C_{1-6}$alkylcarbonyl;
or pharmaceutically acceptable salt, enantiomer or diastereomer thereof;
with the proviso that 5-amino-7-hydroxy-3-[3-hydroxy-5-(hydroxymethyl)tetrahydrofuran-2-yl]thiazolo[4,5-d]pyrimidin-2-one; [2-(5-amino-7-hydroxy-2-oxo-thiazolo[4,5-d]pyrimidin-3-yl)-5-(hydroxymethyl)tetrahydrofuran-3-yl]acetate; [4-acetoxy-5-(5-amino-7-hydroxy-2-oxo-thiazolo[4,5-d]pyrimidin-3-yl)tetrahydrofuran-2-yl]methyl acetate and their diastereomers are excluded.

2. A compound according to claim 1, wherein
$R^1$ is hydroxy, methyl, propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;
$R^2$ is hydrogen, methyl, ethyl, propyl, butyl, cyclopropyl, cyclopentyl, vinyl, allyl, benzyl, ethynyl, 1-propynyl, methoxymethyl or thiophenyl;
$R^3$ is hydrogen, acetyl or isobutyryl;
or pharmaceutically acceptable salt, enantiomer or diastereomer thereof.

3. A compound of formula (Ia) according to claim 1,

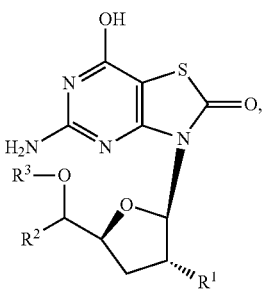

wherein
$R^1$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}$alkyl$)_2$N—, $C_{1-6}$alkylcarbonyl-NH— or heterocyclic amino;
$R^2$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl or thiophenyl;
$R^3$ is hydrogen or $C_{1-6}$alkylcarbonyl;
or pharmaceutically acceptable salt, enantiomer or diastereomer thereof;
with the proviso that 5-amino-7-hydroxy-3-[3-hydroxy-5-(hydroxymethyl)tetrahydrofuran-2-yl]thiazolo[4,5-d]pyrimidin-2-one; [2-(5-amino-7-hydroxy-2-oxo-thiazolo[4,5-d]pyrimidin-3-yl)-5-(hydroxymethyl)tetrahydrofuran-3-yl]acetate; [4-acetoxy-5-(5-amino-7-hydroxy-2-oxo-thiazolo[4,5-d]pyrimidin-3-yl)tetrahydrofuran-2-yl]methyl acetate and their diastereomers are excluded.

4. A compound according to claim 3, wherein
$R^1$ is hydroxy, methyl, propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;
$R^2$ is hydrogen, methyl, ethyl, propyl, butyl, cyclopropyl, cyclopentyl, vinyl, allyl, benzyl, ethynyl, 1-propynyl, methoxymethyl or thiophenyl;
$R^3$ is hydrogen, acetyl or isobutyryl;
or pharmaceutically acceptable salt, enantiomer or diastereomer thereof.

5. A compound according to claim 1, wherein
$R^1$ is hydroxy, $C_{1-6}$alkyl, $C_{1-6}$alkylcarbonyl-O—, $C_{1-6}$alkyl-S—, azido or $C_{2-6}$alkenyl;
$R^2$ is $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;
$R^3$ is hydrogen or $C_{1-6}$alkylcarbonyl;
or pharmaceutically acceptable salt, enantiomer or diastereomer thereof.

6. A compound according to claim 5, wherein
$R^1$ is hydroxy, methyl, propyl, acetyloxy, methylsulfanyl, azido or allyl;
$R^2$ is methyl, ethyl, propyl, butyl, cyclopropyl, cyclopentyl, vinyl, allyl, benzyl, ethynyl, 1-propynyl, methoxymethyl or thiophenyl;
$R^3$ is hydrogen, acetyl or isobutyryl;
or pharmaceutically acceptable salt, enantiomer or diastereomer thereof.

7. A compound according to claim 5 wherein $R^1$ is hydroxy, $C_{1-6}$alkyl, $C_{1-6}$alkyl-S—, azido or $C_{2-6}$alkenyl.

8. A compound according to claim 7, wherein $R^1$ is hydroxy, methyl, n-propyl, methylsulfanyl, azido or allyl.

9. A compound according to claim 5, wherein $R^2$ is $C_{1-6}$alkyl, $C_{3-7}$cycloalkyl, $C_{2-6}$alkynyl or $C_{2-6}$alkenyl.

10. A compound according to claim 9, wherein $R^2$ is methyl, ethyl, n-propyl, cyclopropyl, vinyl, ethynyl or 1-propynyl.

11. A compound according to claim 5, wherein $R^3$ is hydrogen or isobutyryl.

12. A compound according to claim 5, wherein
$R^1$ is hydroxy, $C_{1-6}$alkyl, $C_{1-6}$alkyl-S—, azido or $C_{2-6}$alkenyl;
$R^2$ is $C_{1-6}$alkyl, $C_{3-7}$cycloalkyl, $C_{2-6}$alkynyl or $C_{2-6}$alkenyl;
$R^3$ is hydrogen or $C_{1-6}$alkylcarbonyl;
or pharmaceutically acceptable salt, enantiomer or diastereomer thereof.

13. A compound according to claim 12, wherein
$R^1$ is hydroxy, methyl, propyl, methylsulfanyl, azido or allyl;

R² is methyl, ethyl, propyl, cyclopropyl, vinyl, ethynyl or 1-propynyl;

R³ is hydrogen or isobutyryl;

or pharmaceutically acceptable salt, enantiomer or diastereomer thereof.

14. A compound according to claim 1, wherein

R¹ is haloC$_{1-6}$alkyl, C$_{1-6}$alkyl-S—, cyano, C$_{2-6}$alkenyl, C$_{1-6}$alkylsulfonyl-NH—, (C$_{1-6}$alkyl)$_2$N—, C$_{1-6}$alkylcarbonyl-NH— or heterocyclic amino;

R² is hydrogen;

R³ is hydrogen;

or pharmaceutically acceptable salt, enantiomer or diastereomer thereof.

15. A compound according to claim 14, wherein

R¹ is fluoroisopropyl, methylsulfanyl, cyano, 2-methylallyl, methylsulfonylamino, dimethylamino, acetylamino, pyrrolidinyl, morpholinyl or piperidinyl;

R² is hydrogen;

R³ is hydrogen;

or pharmaceutically acceptable salt, enantiomer or diastereomer thereof.

16. A compound according to claim 14, wherein R¹ is C$_{1-6}$alkyl-S— or heterocyclic amino.

17. A compound according to claim 16, wherein R¹ is methylsulfanyl or pyrrolidinyl.

18. A compound according to claim 1 selected from the group consisting of:

5-Amino-3-[(2R,3R,5S)-3-hydroxy-5-(1-hydroxypropyl)tetrahydrofuran-2-yl]-6H-thiazolo[4,5-c]pyrimidine-2,7-dione;

[(2R,3R,5S)-2-(5-amino-2,7-dioxo-6H-thiazolo[4,5-c]pyrimidin-3-yl)-5-(1-hydroxypropyl)tetrahydrofuran-3-yl]acetate;

[(1S)-1-[(2S,4R,5R)-5-(5-amino-2,7-dioxo-6H-thiazolo[4,5-d]pyrimidin-3-yl)-4-hydroxy-tetrahydrofuran-2-yl]propyl]acetate;

5-Amino-3-[(2R,3R,5S)-3-hydroxy-5-(1-hydroxyethyl)tetrahydrofuran-2-yl]-6H-thiazolo[4,5-c]pyrimidine-2,7-dione;

5-Amino-3-[(2R,3R,5S)-3-hydroxy-5-(1-hydroxybut-3-enyl)tetrahydrofuran-2-yl]-6H-thiazolo[4,5-d]pyrimidine-2,7-dione;

5-Amino-3-[(2R,3R,5S)-3-hydroxy-5-(1-hydroxypentyl)tetrahydrofuran-2-yl]-6H-thiazolo[4,5-c]pyrimidine-2,7-dione;

5-Amino-3-[(2R,3R,5S)-3-hydroxy-5-(1-hydroxybutyl)tetrahydrofuran-2-yl]-6H-thiazolo[4,5-c]pyrimidine-2,7-dione;

5-Amino-3-[(2R,3R,5S)-5-[cyclopentyl(hydroxy)methyl]-3-hydroxy-tetrahydrofuran-2-yl]-6H-thiazolo[4,5-c]pyrimidine-2,7-dione;

5-Amino-3-[(2R,3R,5S)-3-hydroxy-5-(1-hydroxy-2-phenyl-ethyl)tetrahydrofuran-2-yl]-6H-thiazolo[4,5-c]pyrimidine-2,7-dione;

5-Amino-3-[(2R,3R,5S)-3-hydroxy-5-(1-hydroxy-3-methyl-butyl)tetrahydrofuran-2-yl]-6H-thiazolo[4,5-c]pyrimidine-2,7-dione;

5-Amino-3-[(2R,3R,5S)-5-[cyclopropyl(hydroxy)methyl]-3-hydroxy-tetrahydrofuran-2-yl]-6H-thiazolo[4,5-c]pyrimidine-2,7-dione;

[[(2S,4R,5R)-5-(5-amino-2,7-dioxo-6H-thiazolo[4,5-c]pyrimidin-3-yl)-4-hydroxy-tetrahydrofuran-2-yl]-cyclopropyl-methyl]acetate;

5-Amino-3-[(2R,3R,5S)-3-hydroxy-5-(1-hydroxyprop-2-ynyl)tetrahydrofuran-2-yl]-6H-thiazolo[4,5-c]pyrimidine-2,7-dione;

5-Amino-3-[(2R,3R,5S)-3-hydroxy-5-(1-hydroxybut-2-ynyl)tetrahydrofuran-2-yl]-6H-thiazolo[4,5-c]pyrimidine-2,7-dione;

5-Amino-3-[(2R,3R,5S)-3-hydroxy-5-[hydroxy(2-thienyl)methyl]tetrahydrofuran-2-yl]-6H-thiazolo[4,5-c]pyrimidine-2,7-dione;

5-Amino-3-[(2R,3R,5S)-3-hydroxy-5-(1-hydroxy-2-methoxy-ethyl)tetrahydrofuran-2-yl]-6H-thiazolo[4,5-d]pyrimidine-2,7-dione;

5-Amino-3-[(2R,3R,5S)-5-(1-hydroxypropyl)-3-methylsulfanyl-tetrahydrofuran-2-yl]-6H-thiazolo[4,5-d]pyrimidine-2,7-dione;

5-Amino-3-[(2R,3R,5S)-3-azido-5-(1-hydroxypropyl)tetrahydrofuran-2-yl]-6H-thiazolo[4,5-d]pyrimidine-2,7-dione;

5-Amino-3-[(2R,3R,5S)-3-hydroxy-5-(1-hydroxyallyl)tetrahydrofuran-2-yl]-6H-thiazolo[4,5-d]pyrimidine-2,7-dione;

5-Amino-3-((2R,3R,5S)-3-azido-5-((S)-1-hydroxyethyl)tetrahydrofuran-2-yl)thiazolo[4,5-d]pyrimidine-2,7(3H,6H)-dione;

3-[(2R,3R,5S)-3-allyl-5-(1-hydroxypropyl)tetrahydrofuran-2-yl]-5-amino-6H-thiazolo[4,5-d]pyrimidine-2,7-dione;

5-amino-3-[(2R,3R,5S)-5-[(1S)-1-hydroxypropyl]-3-propyl-tetrahydrofuran-2-yl]-6H-thiazolo[4,5-d]pyrimidine-2,7-dione;

5-amino-3-[(2R,3R,5S)-5-[(1R)-1-hydroxypropyl]-3-propyl-tetrahydrofuran-2-yl]-6H-thiazolo[4,5-d]pyrimidine-2,7-dione;

5-amino-3-[(2R,3R,5S)-5-[(1S)-1-hydroxypropyl]-3-methyl-tetrahydrofuran-2-yl]-6H-thiazolo[4,5-d]pyrimidine-2,7-dione;

5-Amino-3-[(2R,3R,5S)-5-[(1S)-1-hydroxybut-2-yl]-3-methyl-tetrahydrofuran-2-yl]-6H-thiazolo[4,5-d]pyrimidine-2,7-dione;

5-Amino-3-[(2R,3R,5S)-5-[(S)-cyclopropyl(hydroxy)methyl]-3-methyl-tetrahydrofuran-2-yl]-6H-thiazolo[4,5-d]pyrimidine-2,7-dione;

5-Amino-3-[(2R,3R,5S)-5-[(1S)-1-hydroxyethyl]-3-methyl-tetrahydrofuran-2-yl]-6H-thiazolo[4,5-d]pyrimidine-2,7-dione;

5-Amino-3-[(2R,3R,5S)-5-(hydroxymethyl)-3-pyrrolidin-1-yl-tetrahydrofuran-2-yl]-6H-thiazolo[4,5-d]pyrimidine-2,7-dione;

N-[(2R,3R,5S)-2-(5-amino-2,7-dioxo-6H-thiazolo[4,5-d]pyrimidin-3-yl)-5-(hydroxymethyl)tetrahydrofuran-3-yl]methanesulfonamide;

N-[(2R,3R,5S)-2-(5-amino-2,7-dioxo-6H-thiazolo[4,5-d]pyrimidin-3-yl)-5-(hydroxymethyl)tetrahydrofuran-3-yl]acetamide;

5-Amino-3-[(2R,3R,5S)-5-(hydroxymethyl)-3-morpholino-tetrahydrofuran-2-yl]-6H-thiazolo[4,5-d]pyrimidine-2,7-dione;

5-Amino-3-[(2R,3R,5S)-5-(hydroxymethyl)-3-(1-piperidyl)tetrahydrofuran-2-yl]-6H-thiazolo[4,5-d]pyrimidine-2,7-dione;

5-Amino-3-[(2R,3R,5S)-3-(dimethylamino)-5-(hydroxymethyl)tetrahydrofuran-2-yl]-6H-thiazolo[4,5-d]pyrimidine-2,7-dione;

(2R,3S,5S)-2-(5-amino-2,7-dioxo-6H-thiazolo[4,5-d]pyrimidin-3-yl)-5-(hydroxymethyl)tetrahydrofuran-3-carbonitrile;

5-Amino-3-[(2R,3R,5S)-5-(hydroxymethyl)-3-methylsulfanyl-tetrahydrofuran-2-yl]-6H-thiazolo[4,5-d]pyrimidine-2,7-dione;

5-Amino-3-[(2R,3R,5S)-3-(1-fluoro-1-methyl-ethyl)-5-(hydroxymethyl)tetrahydrofuran-2-yl]-6H-thiazolo[4,5-d]pyrimidine-2,7-dione;

5-Amino-3-[(2R,3R,5S)-5-(hydroxymethyl)-3-(2-methylallyl)tetrahydrofuran-2-yl]-6H-thiazolo[4,5-d]pyrimidine-2,7-dione; and,

[(1S)-1-[(2S,4R,5R)-5-(5-Amino-2,7-dioxo-6H-thiazolo[4,5-d]pyrimidin-3-yl)-4-hydroxy-tetrahydrofuran-2-yl]propyl] 2-methylpropanoate;

or pharmaceutically acceptable salt, enantiomer or diastereomer thereof.

19. A compound according claim 18 selected from the group consisting of:

5-Amino-3-[(2R,3R,5S)-3-hydroxy-5-(1-hydroxypropyl)tetrahydrofuran-2-yl]-6H-thiazolo[4,5-d]pyrimidine-2,7-dione;

5-Amino-3-[(2R,3R,5S)-3-hydroxy-5-(1-hydroxybutyl)tetrahydrofuran-2-yl]-6H-thiazolo[4,5-d]pyrimidine-2,7-dione;

5-Amino-3-[(2R,3R,5S)-5-[cyclopropyl(hydroxy)methyl]-3-hydroxy-tetrahydrofuran-2-yl]-6H-thiazolo[4,5-d]pyrimidine-2,7-dione;

5-Amino-3-[(2R,3R,5S)-3-hydroxy-5-(1-hydroxyprop-2-ynyl)tetrahydrofuran-2-yl]-6H-thiazolo[4,5-d]pyrimidine-2,7-dione;

5-Amino-3-[(2R,3R,5S)-3-hydroxy-5-(1-hydroxybut-2-ynyl)tetrahydrofuran-2-yl]-6H-thiazolo[4,5-d]pyrimidine-2,7-dione;

5-Amino-3-[(2R,3R,5S)-5-(1-hydroxypropyl)-3-methylsulfanyl-tetrahydrofuran-2-yl]-6H-thiazolo[4,5-d]pyrimidine-2,7-dione;

5-Amino-3-[(2R,3R,5S)-3-azido-5-(1-hydroxypropyl)tetrahydrofuran-2-yl]-6H-thiazolo[4,5-d]pyrimidine-2,7-dione;

5-Amino-3-[(2R,3R,5S)-3-hydroxy-5-(1-hydroxyallyl)tetrahydrofuran-2-yl]-6H-thiazolo[4,5-d]pyrimidine-2,7-dione;

3-[(2R,3R,5S)-3-allyl-5-(1-hydroxypropyl)tetrahydrofuran-2-yl]-5-amino-6H-thiazolo[4,5-d]pyrimidine-2,7-dione;

5-amino-3-[(2R,3R,5S)-5-[(1S)-1-hydroxypropyl]-3-propyl-tetrahydrofuran-2-yl]-6H-thiazolo[4,5-d]pyrimidine-2,7-dione;

5-amino-3-[(2R,3R,5S)-5-[(1R)-1-hydroxypropyl]-3-propyl-tetrahydrofuran-2-yl]-6H-thiazolo[4,5-d]pyrimidine-2,7-dione;

5-amino-3-[(2R,3R,5S)-5-[(1S)-1-hydroxypropyl]-3-methyl-tetrahydrofuran-2-yl]-6H-thiazolo[4,5-d]pyrimidine-2,7-dione;

5-Amino-3-[(2R,3R,5S)-5-[(1S)-1-hydroxybut-2-yl]-3-methyl-tetrahydrofuran-2-yl]-6H-thiazolo[4,5-d]pyrimidine-2,7-dione;

5-Amino-3-[(2R,3R,5S)-5-[(S)-cyclopropyl(hydroxy)methyl]-3-methyl-tetrahydrofuran-2-yl]-6H-thiazolo[4,5-d]pyrimidine-2,7-dione;

5-Amino-3-[(2R,3R,5S)-5-[(1S)-1-hydroxyethyl]-3-methyl-tetrahydrofuran-2-yl]-6H-thiazolo[4,5-d]pyrimidine-2,7-dione;

5-Amino-3-[(2R,3R,5S)-5-(hydroxymethyl)-3-pyrrolidin-1-yl-tetrahydrofuran-2-yl]-6H-thiazolo[4,5-d]pyrimidine-2,7-dione;

5-Amino-3-[(2R,3R,5S)-5-(hydroxymethyl)-3-methylsulfanyl-tetrahydrofuran-2-yl]-6H-thiazolo[4,5-d]pyrimidine-2,7-dione; and,

[(1S)-1-[(2S,4R,5R)-5-(5-Amino-2,7-dioxo-6H-thiazolo[4,5-d]pyrimidin-3-yl)-4-hydroxy-tetrahydrofuran-2-yl]propyl] 2-methylpropanoate;

or pharmaceutically acceptable salt, enantiomer or diastereomer thereof.

20. A compound of formula (II),

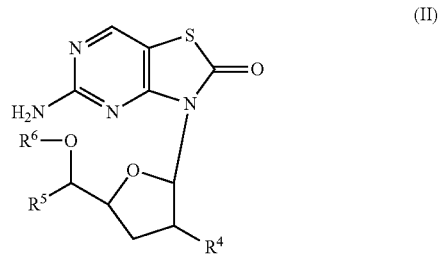

(II)

wherein $R^4$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}$alkyl$)_2$N—, $C_{1-6}$alkylcarbonyl-NH— or heterocyclic amino;

$R^5$ is hydrogen, $C_{1-6}$alkyl, $C_{1-6}$alkoxy$C_{1-6}$alkyl, $C_{3-7}$cycloalkyl, $C_{2-6}$alkynyl, $C_{2-6}$alkenyl, benzyl and thiophenyl;

$R^6$ is hydrogen or $C_{1-6}$alkylcarbonyl;

or pharmaceutically acceptable salt, enantiomer or diastereomer thereof;

with the proviso that 5-amino-3-[3-hydroxy-5-(hydroxymethyl)tetrahydrofuran-2-yl]thiazolo[4,5-d]pyrimidin-2-one; [2-(5-amino-2-oxo-thiazolo[4,5-d]pyrimidin-3-yl)-5-(hydroxymethyl)tetrahydrofuran-3-yl] acetate; [4-acetoxy-5-(5-amino-2-oxo-thiazolo[4,5-d]pyrimidin-3-yl)tetrahydrofuran-2-yl]methyl acetate and their diastereomers are excluded.

21. A compound according to claim 20 wherein $R^4$ is hydroxy, methyl, n-propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;

$R^5$ is hydrogen, methyl, ethyl, propyl, butyl, cyclopropyl, cyclopentyl, vinyl, allyl, benzyl, ethynyl, 1-propynyl, methoxymethyl or thiophenyl;

$R^6$ is hydrogen, acetyl or isobutyryl;

or pharmaceutically acceptable salt, enantiomer or diastereomer thereof.

22. A compound of formula (IIa) according to claim 20,

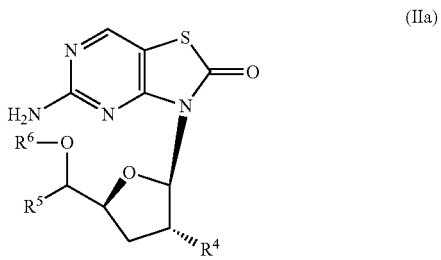

(IIa)

wherein $R^4$ is hydroxy, $C_{1-6}$alkyl, halo$C_{1-6}$alkyl, $C_{1-6}$alkylcarbonyl-O—, $C_{1-6}$alkyl-S—, azido, cyano, $C_{2-6}$alkenyl, $C_{1-6}$alkylsulfonyl-NH—, $(C_{1-6}$alkyl$)_2$N—, $C_{1-6}$alkylcarbonyl-NH— or heterocyclic amino;

R⁵ is hydrogen, C₁₋₆alkyl, C₁₋₆alkoxyC₁₋₆alkyl, C₃₋₇cycloalkyl, C₂₋₆alkynyl, C₂₋₆alkenyl, benzyl and thiophenyl;

R⁶ is hydrogen or C₁₋₆alkylcarbonyl;

or pharmaceutically acceptable salt, enantiomer or diastereomer thereof;

with the proviso that 5-amino-3-[3-hydroxy-5-(hydroxymethyl)tetrahydrofuran-2-yl]thiazolo[4,5-d]pyrimidin-2-one; [2-(5-amino-2-oxo-thiazolo[4,5-d]pyrimidin-3-yl)-5-(hydroxymethyl)tetrahydrofuran-3-yl] acetate; [4-acetoxy-5-(5-amino-2-oxo-thiazolo[4,5-d]pyrimidin-3-yl)tetrahydrofuran-2-yl]methyl acetate and their diastereomers are excluded.

23. A compound according to claim 22 wherein
R⁴ is hydroxy, methyl, n-propyl, fluoroisopropyl, acetyloxy, methylsulfanyl, azido, cyano, allyl, 2-methylallyl, methylsulfonylamino, dimethylamino, acetylamino, pyrrolidinyl, morpholinyl or piperidinyl;
R⁵ is hydrogen, methyl, ethyl, propyl, butyl, cyclopropyl, cyclopentyl, vinyl, allyl, benzyl, ethynyl, 1-propynyl, methoxymethyl or thiophenyl;
R⁶ is hydrogen, acetyl or isobutyryl;
or pharmaceutically acceptable salt, enantiomer or diastereomer thereof.

24. A compound according to claim 20 wherein
R⁴ is hydroxy, C₁₋₆alkyl, C₁₋₆alkyl-S—, azido or C₂₋₆alkenyl;
R⁵ is C₁₋₆alkyl, C₃₋₇cycloalkyl, C₂₋₆alkynyl or C₂₋₆alkenyl;
R⁶ is hydrogen or C₁₋₆alkylcarbonyl;
or pharmaceutically acceptable salt, enantiomer or diastereomer thereof.

25. A compound according to claim 20 wherein
R⁴ is hydroxy, methyl, propyl, methylsulfanyl, azido or allyl;
R⁵ is methyl, ethyl, propyl, cyclopropyl, vinyl, ethynyl or 1-propynyl;
R⁶ is hydrogen or isobutyryl;
or pharmaceutically acceptable salt, enantiomer or diastereomer thereof.

26. A compound according to claim 20 wherein
R⁴ is hydroxy or C₁₋₆alkylcarbonyl-O—;
R⁵ is C₁₋₆alkyl or C₃₋₇cycloalkyl;
R⁶ is hydrogen or C₁₋₆alkylcarbonyl;
or pharmaceutically acceptable salt, enantiomer or diastereomer thereof.

27. A compound according to claim 20 wherein
R⁴ is hydroxy or acetyloxy;
R⁵ is ethyl or cyclopropyl;
R⁶ is hydrogen or acetyl;
or pharmaceutically acceptable salt, enantiomer or diastereomer thereof.

28. A compound according to claim 20 selected from the group consisting of:
5-Amino-3-[(2R,3R,5S)-3-hydroxy-5-(1-hydroxypropyl)tetrahydrofuran-2-yl]thiazolo[4,5-d]pyrimidin-2-one;
[(2R,3R,5S)-2-(5-amino-2-oxo-thiazolo[4,5-d]pyrimidin-3-yl)-5-(1-hydroxypropyl)tetrahydrofuran-3-yl]acetate;
1-[(2S,4R,5R)-5-(5-amino-2-oxo-thiazolo[4,5-d]pyrimidin-3-yl)-4-hydroxy-tetrahydrofuran-2-yl]propyl acetate;
[(S)-[(2S,4R,5R)-5-(5-amino-2-oxo-thiazolo[4,5-d]pyrimidin-3-yl)-4-hydroxy-tetrahydrofuran-2-yl]-cyclopropyl-methyl]acetate; and,
5-Amino-3-[(2R,3R,5S)-5-[cyclopropyl(hydroxy)methyl]-3-hydroxy-tetrahydrofuran-2-yl]thiazolo[4,5-d]pyrimidin-2-one;
or pharmaceutically acceptable salt, enantiomer or diastereomer thereof.

29. A pharmaceutical composition comprising a compound in accordance claim 1 and a therapeutically inert carrier.

30. A pharmaceutical composition comprising a compound in accordance claim 3 and a therapeutically inert carrier.

31. A method for treating a Hepatitis B virus infection comprising administering to a patient in need thereof a therapeutically effective amount of a compound according to claim 1.

32. A method for treating a Hepatitis B virus infection comprising administering to a patient in need thereof a therapeutically effective amount of a compound according to claim 3.

33. A method of activating the TLR7 receptor in a patient in need thereof comprising administering an effective amount of a compound according to claim 1.

34. A method of activating the TLR7 receptor in a patient in need thereof comprising administering an effective amount of a compound according to claim 3.

35. A method of stimulating production of interferon-α comprising administering to a patient in need thereof a therapeutically effective amount of a compound according to claim 1.

36. A method of stimulating production of interferon-α comprising administering to a patient in need thereof a therapeutically effective amount of a compound according to claim 3.

37. A pharmaceutical composition comprising a compound in accordance with claim 20 and a therapeutically inert carrier.

38. A pharmaceutical composition comprising a compound in accordance with claim 22 and a therapeutically inert carrier.

39. A method for treating a Hepatitis B virus infection comprising administering to a patient in need thereof a therapeutically effective amount of a compound according to claim 20.

40. A method for treating a Hepatitis B virus infection comprising administering to a patient in need thereof a therapeutically effective amount of a compound according to claim 22.

41. A method of activating the TLR7 receptor in a patient in need thereof comprising administering an effective amount of a compound according to claim 20.

42. A method of activating the TLR7 receptor in a patient in need thereof comprising administering an effective amount of a compound according to claim 22.

43. A method of stimulating production of interferon-α comprising administering to a patient in need thereof a therapeutically effective amount of a compound according to claim 20.

44. A method of stimulating production of interferon-α comprising administering to a patient in need thereof a therapeutically effective amount of a compound according to claim 22.

45. A compound which is 5-amino-3-[(2R,3R,5S)-3-hydroxy-5-(1-hydroxypropyl)tetrahydrofuran-2-yl]-6H-thiazolo[4,5-d]pyrimidine- 2,7-dione or pharmaceutically acceptable salt, enantiomer or diastereomer thereof.

46. A compound which is [(2R,3R,5S)-2-(5-amino-2,7-dioxo-6H-thiazolo[4,5-d]pyrimidin-3-yl)-5-(1-hydroxypropyl)tetrahydrofuran-3-yl]acetate or pharmaceutically acceptable salt, enantiomer or diastereomer thereof.

47. A compound which is [(1S)-1-[(2S,4R,5R)-5-(5-amino-2,7-dioxo-6H-thiazolo[4,5-d]pyrimidin-3-yl)-4-hydroxytetrahydrofuran-2-yl]propyl]acetate or pharmaceutically acceptable salt, enantiomer or diastereomer thereof.

48. A compound which is [[(2S,4R,5R)-5-(5-amino-2,7-dioxo-6H-thiazolo[4,5-d]pyrimidin- 3-yl)-4-hydroxytetrahydrofuran-2-yl]-cyclopropyl-methyl]acetate or pharmaceutically acceptable salt, enantiomer or diastereomer thereof.

49. A compound which is 5-amino-3-[(2R,3R,5S)-5-[cyclopropyl(hydroxy)methyl]-3-hydroxy-tetrahydrofuran-2-yl]-6H-thiazolo[4,5-d]pyrimidine-2,7-dione or pharmaceutically acceptable salt, enantiomer or diastereomer thereof.

50. A compound which is 5-amino-3-[(2R,3R,5S)-3-hydroxy-5-(1-hydroxypropyl)tetrahydrofuran-2-yl]thiazolo[4,5-d]pyrimidin-2-one or pharmaceutically acceptable salt, enantiomer or diastereomer thereof.

51. A compound which is [(2R,3R,5S)-2-(5-amino-2-oxo-thiazolo[4,5-d]pyrimidin-3-yl)-5-(1-hydroxypropyl)tetrahydrofuran-3-yl]acetate or pharmaceutically acceptable salt, enantiomer or diastereomer thereof.

52. A compound which is 1-[(2S,4R,5R)-5-(5-amino-2-oxo-thiazolo[4,5-d]pyrimidin-3-yl)-4-hydroxy-tetrahydrofuran-2-yl]propyl acetate or pharmaceutically acceptable salt, enantiomer or diastereomer thereof.

53. A compound which is [(S)-[(2S,4R,5R)-5-(5-amino-2-oxo-thiazolo[4,5-d]pyrimidin-3-yl)-4-hydroxy-tetrahydrofuran-2-yl]- cyclopropyl-methyl]acetate or pharmaceutically acceptable salt, enantiomer or diastereomer thereof.

54. A compound which is 5-amino-3-[(2R,3R,5S)-5-[cyclopropyl(hydroxy)methyl]-3-hydroxy-tetrahydrofuran-2-yl]thiazolo[4,5-d]pyrimidin-2-one or pharmaceutically acceptable salt, enantiomer or diastereomer thereof.

* * * * *